(12) United States Patent
Srivastava et al.

(10) Patent No.: US 9,186,362 B2
(45) Date of Patent: Nov. 17, 2015

(54) METHODS INVOLVING ALDOSE REDUCTASE INHIBITORS

(75) Inventors: Satish K. Srivastava, Galveston, TX (US); Kota V. Ramana, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 151 days.

(21) Appl. No.: 13/546,009

(22) Filed: Jul. 11, 2012

(65) Prior Publication Data

US 2013/0023529 A1 Jan. 24, 2013

Related U.S. Application Data

(62) Division of application No. 12/532,553, filed as application No. PCT/US2008/057998 on Mar. 24, 2008, now Pat. No. 8,273,746.

(60) Provisional application No. 60/896,752, filed on Mar. 23, 2007.

(51) Int. Cl.
| | |
|---|---|
| A61K 31/50 | (2006.01) |
| A61K 31/538 | (2006.01) |
| A61K 31/4188 | (2006.01) |
| A61K 31/502 | (2006.01) |
| A61K 31/535 | (2006.01) |
| A61K 31/4164 | (2006.01) |
| A61K 31/4166 | (2006.01) |
| A61K 31/499 | (2006.01) |
| C12N 15/113 | (2010.01) |

(52) U.S. Cl.
CPC .......... *A61K 31/538* (2013.01); *A61K 31/4164* (2013.01); *A61K 31/4166* (2013.01); *A61K 31/4188* (2013.01); *A61K 31/499* (2013.01); *A61K 31/50* (2013.01); *A61K 31/502* (2013.01); *A61K 31/535* (2013.01); *C12N 15/1137* (2013.01); *C12N 2310/14* (2013.01); *C12Y 101/01021* (2013.01)

(58) Field of Classification Search
None
See application file for complete search history.

(56) References Cited

U.S. PATENT DOCUMENTS

| | | | |
|---|---|---|---|
| 4,130,714 A | 12/1978 | Sarges | |
| 4,251,528 A | 2/1981 | Brittain et al. | |
| 4,436,745 A | 3/1984 | York, Jr. | |
| 4,438,272 A | 3/1984 | York, Jr. | |
| 4,464,382 A | 8/1984 | Tanouchi et al. | |
| 4,540,704 A | 9/1985 | Ueda et al. | |
| 4,600,724 A | 7/1986 | Sestanj et al. | |
| 4,734,419 A | 3/1988 | Hashimoto et al. | |
| 4,771,050 A | 9/1988 | Meguro et al. | |
| 4,780,469 A | 10/1988 | Toda et al. | |
| 4,791,126 A | 12/1988 | Tanouchi et al. | |
| 4,831,045 A | 5/1989 | Tanouchi et al. | |
| 4,883,410 A | 11/1989 | Goddard et al. | |
| 4,883,800 A | 11/1989 | Hashimoto et al. | |
| 4,980,357 A | 12/1990 | Goldstein et al. | |
| 5,037,831 A | 8/1991 | Malamas | |
| 5,066,659 A | 11/1991 | Lipinski | |
| 5,068,332 A * | 11/1991 | Malamas | 546/18 |
| 5,246,971 A | 9/1993 | Williamson et al. | |
| 5,252,572 A | 10/1993 | Hermez et al. | |
| 5,270,342 A | 12/1993 | Brittain et al. | |
| 5,430,060 A | 7/1995 | Brittain et al. | |
| 5,447,946 A | 9/1995 | Kurono et al. | |
| 5,990,111 A | 11/1999 | Johnson | |
| 5,990,177 A | 11/1999 | Brown | |
| 6,127,367 A | 10/2000 | Beyer et al. | |
| 6,339,088 B1 | 1/2002 | Ueno et al. | |
| 6,380,200 B1 | 4/2002 | Mylari | |
| 6,489,308 B1 | 12/2002 | Shapiro | |
| 6,581,599 B1 | 6/2003 | Stenzler | |
| 6,583,180 B2 | 6/2003 | Link et al. | |
| 6,696,407 B1 | 2/2004 | Longo et al. | |
| 6,720,348 B2 | 4/2004 | Mylari | |
| 6,774,128 B2 | 8/2004 | Watkins et al. | |
| 7,702,430 B2 | 4/2010 | Srivastava et al. | |
| 2001/0002405 A1 | 5/2001 | Fossel | |
| 2002/0198201 A1 | 12/2002 | Privette et al. | |
| 2003/0195252 A1 | 10/2003 | Sattur et al. | |
| 2003/0236254 A1 | 12/2003 | Lohray et al. | |
| 2004/0259816 A1 | 12/2004 | Pandol et al. | |
| 2005/0026882 A1 | 2/2005 | Robinson et al. | |
| 2006/0293265 A1 | 12/2006 | Srivastava et al. | |
| 2007/0021366 A1 | 1/2007 | Srivastava et al. | |
| 2010/0016404 A1 | 1/2010 | Srivastava et al. | |
| 2010/0022625 A1 | 1/2010 | Srivastava et al. | |
| 2011/0092566 A1 | 4/2011 | Srivastava et al. | |

FOREIGN PATENT DOCUMENTS

| | | |
|---|---|---|
| EP | 0 296 695 | 12/1988 |
| EP | 0 437 025 | 7/1991 |
| EP | 0473308 | 3/1992 |
| EP | 1026149 | 8/2000 |

(Continued)

OTHER PUBLICATIONS

Hotta et al (Diabetes Care 24:1776-1782, 2001).*
Karin, "The beginning of the end:IKB kinase (IKK) and NF-KB activation," J. Bioi. Chern. 274(39):27339-27342, 1999.
Kassab et al., "Vascular complications in diabetes and their prevention," Vase. Med. 6:249-255, 2001.
King et al., "Biochemical and molecular mechanisms in the development of diabetic vascular complications," Diabetes 45:S 1 05-S 108, 1996.

(Continued)

*Primary Examiner* — Craig Ricci
(74) *Attorney, Agent, or Firm* — Norton Rose Fulbright US LLP

(57) ABSTRACT

Embodiments of the invention include methods and compositions involving aldose reductase inhibitors for the treatment of inflammation, including uveitis and asthma.

7 Claims, 34 Drawing Sheets

(56) References Cited

FOREIGN PATENT DOCUMENTS

| EP | 1167357 | 1/2002 |
|---|---|---|
| EP | 2110141 | 10/2009 |
| JP | H0789857 | 4/1995 |
| JP | 2003252794 | 9/2003 |
| WO | WO/92/06974 | 4/1992 |
| WO | WO/02/98510 | 12/2002 |
| WO | WO/2005/011595 | 2/2005 |
| WO | WO/2005/044260 | 5/2005 |
| WO | WO/2005/112960 | 12/2005 |
| WO | WO 2006/019851 | 2/2006 |

OTHER PUBLICATIONS

Kinoshita, "A thirty year journey in the polyol pathway," Exp Eye Res 50:567-573, 1990.
Kirpichnikov and Sowers, "Diabetes mellitus and diabetes-associated vascular disease," Trends Endocrinol. Metab. 12(5):225-230, 2001.
Kloek et al., "Modulation of airway hyperresponsiveness by thiols in a murine in vivo model of allergic asthma," Jnflamm. Res., 52:126-131,2003.
Ko et al., "Purification, identification, and characterization of an osmotic response element binding protein," Biochem. Biophys. Res. Comm. 270:52-61,2000.
Koya and King "Protein kinase C activation and the development of diabetic complications," Diabetes 47:859-866, 1998.
Lee and Chung, "Contributions ofpolyol pathway to oxidative stress in diabetic cataract," FASEB J, 13:23-30, 1999.
Lee et al., "Activation of c-jun N-terminal kinase and activator protein 1 by receptor activatior ofnuclear factor KB," Mol. Pharmacal. 58(6):1536-1545, 2000.
Lee et al., "Demonstration that polyol accumulation is responsible for diabetic cataract by the use of transgenic mice expressing the aldose reductase gene in the lens," Proc. Nat/. Acad. Sci. USA. 92:2780-2784, 1995.
Lin et al., "Family history of inflammatory bowel disease in patients with idiopathic ocular inflammation," Am. J Ophthalmol., 141:1097-104,2006.
Litherland et al., "Intracellular signalling mechanisms regulating glucose transport in insulinsensitive tissues," Mol. Membr. Bioi. 18:195-204, 2001.
Liu et al., "Identification of the reactive cysteine residue in human placenta aldose reductase," . Biochim Biophys Acta. 1164:268-272, 1993.
Liu et al., "Induction of cataract-like changes in rat lens epithelial explants by transforming growth factor beta," Invest. Ophthalmol. Vis. Sci., 35:388-401, 1994.
Lovicu and McAvoy, "FGF-induced lens cell proliferation and differentiation is dependent on MAPK (ERK.I/2) signalling," Development, 128:5075-5084, 2001.
Mackenzie and Wilson, "The management of sepsis," Practical Procedures, 13(article 8):1-5, 2001.
Mansfield et al., "Effects of dexamethasone on posterior capsule opacification-like changes in a rat lens explant model," Mol. Vis., 10:728-737, 2004.
Meacock et al., "Role of cytokines in the pathogenesis of posterior capsule opacification," Br. J. Ophthalmol., 84:332-336, 2000.
Mitchell et al., "The pathophysiology ofatherosclerosis," Semin. Vase. Surg. 11:134-141, 1998.
Miwa et al., "The role ofpolyol pathway in glucose-induced apoptosis of cultured retinal pericytes," Diabetes Res. Clin. Pract., 60: 1-9, 2003.
Miyakawa et al., "Tonicity-responsive enhancer binding protein, a Rei-like protein that stimulates transcription in response to hypertonicity," Proc. Nat!. A cad. Sci. USA. 96:2538-42, 1999.
Murata et al. , "The role of aldose reductase in sugar cataract formation: aldose reductase plays a key role in lens epithelial cell death (apoptosis)," Chem. Bioi. Interact., 130-131:617-625, 2001.
Nakajima and Takatsu, "Role of cytokines in allergic airway inflammation," Int. Arch. Allergy Immunol., 142:265-273, 2006.

Nakamura et al., "Effectiveness of aldose reductase inhibitors for diabetic gastroenteropathy with constipation," Internal. Medicine, 36:479-83, 1997.
Nakamura et al., "Induction of aldose reductase in cultured human microvascular endothelial cells by advanced glycation end products," Free Radic. Bioi. Med., 29:17-25, 2000.
Niemann-Jonsson et al., "Increased rate ofapoptosis in intimal arterial smooth muscle cells through endogenous activation ofTNF receptors," Arterioscle. Thromb. Vase. Bioi. 21:1909-14, 2001.
Nishi, "Posterior capsule opacification. Part 1: Experimental investigations," J. Cataract. Refract. Sur g., 25: 106-117, 1999.
Nishikawa et al., "Normalizing mitochondrial superoxide production blocks three pathways of hyperglycaemic damage," Nature, 404:787-90, 2000.
Nishikawa et al., "The missing link: A single unifying mechanism for diabetic complications," Kidney Internt Suppl., 58:S26-S30, 2000.
O'Connor et al., "Major differences exist in the function and tissue-specific expression of human aflatoxin B I aldehyde reductase and the principal human a! do-keto reductase AKR I family members," Biochem. J., 343 (Pt. 2):487-504, 1999.
Office Action, issued in related Application No. I 0/462,223, mailed Aug. 18, 2004.
Office Action, issued in related U.S. Appl. No. 11/364,823, mailed Feb. 27, 2007.
Office Action, issued in related Application No. 111210,283, mailed Jul. 10, 2007.
Office Action, issued in related Application No. 111210,283, mailed Feb. 7, 2008.
Office Action, issued in related U.S. Appl. No. 11/210,283, mailed Jul. 22, 2008.
Office Action, issued in related U.S. Appl. No. 11/210,283, mailed Dec. 23, 2008.
Office Action, issued in related U.S. Appl. No. 11/210,283, mailed Jul. 17, 2009.
Office Action, issued in related Application No. 111210,283, mailed Jan. 12, 2010.s.
Opalinska and Gewirtz, "Nucleic-acid therapeutics: basic principles and recent applications," Nature Reviews, 1:503-14,2002.
Orchard et al., "Uveitis and erythema nodosum in inflammatory bowel disease: clinical features and the role ofHLA genes," Gastroenterology, 123:714-718,2002.
Pladzyk et al., "Inhibition of aldose reductase prevents lipopolysaccharide-induced inflammatory response in human lens epithelial cells," Invest. Opthamol. Vis. Sci., 47:5395-403,2006.
Prieto et al., "Effect of challenge method on sensitivity, reactivity, and maximal response to methacholine," Ann. Allergy Asthma. Immunol., 97:175-181, 2006.
Purves et al., "A role for mitogen-activated protein kinases in the etiology of diabetic neuropathy," FASEB J. 15:2508-2514,2001.
Rabinovitch, "An update on cytokines in the patogenesis of insulin-dependant diabetes mellitus," Diabetes Metab. Rev. 14:129-151, 1998.
Rahman et al., "4-Hydroxy-2-nonenal, a specific lipid peroxidation product, is elevated in lungs of patients with chronic obstructive pulmonary disease," Am. J Respir. Crit. Care Med., 166:490-495, 2002.
Ramana et al., "Activation of nuclear factor-kappaB by hyperglycemia in vascular smooth muscle cells is regulated by aldose reductase," Diabetes, 53:2910-2920, 2004.
Ramana et al., "Aldose reductase mediates cytotoxic signals of hyperglycemia and TNF-alpha in human lens epithelial cells," FASEB J, 17:315-17, 2003.
Ramana et al., "Aldose reductase mediates mitogenic signaling in vascular smooth muscle cells," J Bioi. Chem., 277:32063-32070, 2002.
Ramana et al., "Aldose reductase mediates the lipopolysaccharide-induced release of inflammatory mediators in RA W264. 7 murine macrophages," J Bioi. Chem., 281 :33019-33029, 2006.
Wang et al., "NF-KB is required for TFN-a-directed smooth muscle cell migration," FEES Lett. 508:360-364,2001.
Wang et al., "Role of calcium-dependant protease(s) in globalization of isolated rat lens cortical fiber cells," Invest. Ophthalmol. Vis. Sci. 42:194-199, 2001.

(56) References Cited

OTHER PUBLICATIONS

West et al., "Regulation of striatal dopamine neuro transmission by nitric oxide: effector pathways and signaling mechanisms," Synapse, 44:227-245, 2002.
Wisnewski et al., "Glutathione protects human airway proteins and epithelial cells from isocyanates," Clin. Exp. Allergy, 35:352-357, 2005.
Wood et al., "Biomarkers oflipid peroxidation, airway inflammation and asthma," Eur. Respir. J, 21:177-186,2003.
Wormstone et al., "Hepatocyte growth factor function and c-Met expression in human lens epithelial cells," Invest. Ophthalmol. Vis. Sci., 41:4216-4222, 2000.
Wu, "Review of diabetes:identification of markers for early detection, glycemic control, and monitoring clinical complications," J Clin. Lab. Anal., 7:293-300, 1993.
Yabe-Nishimura, "Aldose reductase in glucose toxicity: a potential target for the prevention of diabetic complications," Pharmacal. Rev., 50:21-22, 1998.
Yadav et al., "Aldose reductase inhibition prevents endotoxin-induced uveitis in rats," Invest. Ophthalmol. Vis. Sci., 48:4634-4642, 2007.
Yamamoto et al., "Nitric oxide synthase inhibitor blocks spinal sensitization induced by formalin injection into the rat paw," Anesthesia & Analgesia, 77:886-890, 1995 (Abstract).
Yang et al., "Decreased SLIM1 expression and increased gelsolin expression in failing human hearts measured by high-density oligonucleotide arrays," Circulation, 102:3046-52,2000.
Zenon et al., "Potential use of aldose reductase inhibitors to prevent diabetic complications," Clin. Pharm., 9:446-457, 1990.
National Heart Lung and Blood Institute website (NHLBI, available online at http://www.nhlbi.nih.gov/health/dci/Diseases/Asthma/Asthma_Prevention.html) accessed Dec. 14, 2010.
Medical News Today (available online at http://www.medicalnewstoday.com/articles/55165.php) accessed Dec. 14, 2010.
Douek et al. Children with type-1 diabetes and their unaffected siblings have fewer symptoms of asthma, The Lancet, May 29, 1999, 1850, 353.
Aggarwal, B. Tumor necrosis factors receptor associated with signaling molecules and their role in activation of aptosis, JNK and NF-kB. Ann Reum Dis 2000; 59 (suppl1): i6-i16.
Apple et al., "Posterior capsule opacification," Surv. Ophthalmol., 37:73-116, 1992.
Bacsi et al., "Effect of pollen-mediated oxidative stress on immediate hypersensitivity reactions and late-phase inflammation in allergic conjunctivitis," J Allergy Clin. Immunol., 116:836-843, 2005.
Barisani et al., "Iron overload and gene expression in HepG2 cells: analysis by differential display," FEES Lett., 469:208-12,2000.
Berrazueta et al., "Local trans dermal glyceryl trinitrate has an antiinflammatory action on thrombonphlebitis induced by sclerosis ofleg varicose veins," Angiology, 45:347-351, 1994 (Abstract).
Bhatnagar and Srivastava, "Aldose reductase: congenial and injurious profiles of an enigmatic enzyme," Biochem. Med Metab. Bioi., 48:91-121, 1992.
Bhatnagar et al., "Inhibition kinetics of human kidney aldose and aldehyde reductases by aldose reductase inhibitors," Biochem. Pharmacal. 39:1115-1124, 1990.
Bianchi et al., "An inhibitor of macrophage arginine transport and nitric oxide production (CNI-1493) prevents acute inflammation and endotoxin lethality," Molecular Medicine, 1:254-266, 1995.
Biswas et al., "Animal study on the effects of catalin on aftercataract and posterior capsule opacification," Ophthalmic Res., 31:140-142, 1999.
Boldogh etal., "ROS generated by pollen NADPH oxidase provide a signal that augments antigen-induced allergic airway inflammation," J Clin. Invest., 115:2169-2179, 2005.
Bours et al., "NF-KB activation in response to toxical and therapeutical agents: role in inflammation and cancer treatment," Toxicology, 153:27-38,2000.
Brownlee, "Biochemistry and molecular cell biology of diabetic complications," Nature 414:813-820,2001.
Bucala, "Lipid and lipoprotein modification by advanced glycosylation end-products: role in atherosclerosis," Exp. Phsyiol: Physiololgical society syposium: Impaired endothelial and smooth muscle eel/function in oxidative stress, 82:327-337, 1997.
Burg et al., "Regulation of gene expression by hypertonicity,"Ann. Rev. Physiol. 59:437-55, 1997.
Burg, "Molecular basis of osmotic regulation," Am. J Physiol. 268:F983-F996, 1995.
Cai et al., "Endothelial dysfunction in cardiovascular diseases," Circ. Res., 87:840-844, 2000.
Chandra et al., "Modification of aldose reductase by S-Nirosoglutathione," Biochemistry 36:1580 I-I5809, I997.
Chang and Crapo, "Inhibition of airway inflammation and hyperreactivity by an antioxidant mimetic," Free Radic. Biol. Med., 33:379-386, 2002.
Chen et al., "Control ofPDGF-induced reactive oxygen species (ROS) generation and signal transduction in human lens epithelial cells," Mol. Vis., 13:374-387, 2007.
Chirila et al., "The use of synthetic polymers for delivery of therapeutic antisense oligodeoxynucleotides," Biomaterials, 23:32I-42, 2002.
Choi et al., "Hepatocyte growth factor induces proliferation of lens epithelial cells through activation ofERK.I/2 and JNK/SAPK," Invest. Ophthalmol. Vis. Sci., 45:2696-2704,2004.
Corradi et al., "Comparison between exhaled and sputum oxidative stress biomarkers in chronic airway inflammation," Eur. Respir. J, 24: I 0 II-I 0 I7, 2004.
Cortina et al., "Diclofenac sodium and cyclosporin A inhibit human lens epithelial cell proliferation in culture," Graefes. Arch. Clin. Exp. Ophthalmol., 235:I80-I85, I997.
Czech and Corvera, "Signaling mechanisms that regulate glucose transport," J Biol. Chern. 274:I865-I868, I999.
De longh et al., "Transforming growth factor-beta-induced epithelial-mesenchymal transition in the lens: a model for cataract formation," Cells, Tissues, Organs, I79:43-55, 2005.
Delamaire et al., "Impaired leucocyte functions in diabetic patients," Diabetic Medicine, I4:29-34,I997.
Dick et al., "The role of tumour necrosis factor (TNF-alpha) in experimental autoimmune uveoretinitis (EAU)," Prog. Reti. Eye Res., 23:6I7-637, 2004.
Dixit et al., "Kinetic and structural characterization of the glutathione-binding site of aldose reductase," J Bioi. Chern., 275:2I587-21595, 2000.
Doganay et al., "Use of caffeic acid phenethyl ester to prevent sodium-selenite-induced cataract in rat eyes," J. Cataract. Refract. Surg., 28:1457-1462,2002.
Donohue et al., "A delayed-early gene activated by fibroblast growth factor-! encodes a protein related to aldose reductase," J. Biol. Chem. 269(11):8604-8609, 1994.
Earnshaw et al., "Mammilian caspases: structure, activation, substates, and functions during apoptosis," Ann. Rev. Biochem. 68:3 83-424, 1999.
El-Shabrawi and Hermann, "Anti-tumor necrosis factor-alpha therapy with infliximab as an alternative to corticosteroids in the treatment of human leukocyte antigen B27-associated acute anterior uveitis," Ophthalmology, 109:2342-2346, 2002.
Frode-Saleh et at., "Synergistic antiinflammatory effect ofNF-kappaB inhibitors and steroidal or non steroidal antiinflammatory drugs in the pleural inflammation induced by carrageenan in mice," Injlamm. Res., 49:330-337, 2000.
Gagliardo et al., "Persistent activation of nuclear factor-kappaB signaling pathway in severe uncontrolled asthma," Am. J. Respir. Crit. Care Med., 168:1190-1198, 2003.
Griendling et al., "Angiotensin II stimulates NADH and NADPH oxidase activity in cultured vascular smooth muscle cells," Circ. Res., 74:1141-1148, 1994.
Hale and Lightman, "Anti-TNF therapies in the management of acute and chronic uveitis," Cytokine, 33:231-237,2006.
Hamilton et al., "4-Hydroxynonenal mimics ozone-induced modulation of macrophage function ex vivo," Am. J. Respir Cell. Mol. Biol., 15:275-282, 1996.

(56) References Cited

OTHER PUBLICATIONS

Hepsen et al., "Caffeic acid phenethyl ester to inhibit posterior capsule opacification in rabbits," J. Cataract. Refract. Surg., 23:1572-1576, 1997.
Hoshi et al., "Regulation of vascular smooth muscle cell proliferation by nuclear factor-KB and its inhibitor, ts nhibitor, 1-KB," J. Biol. Chern. 275(2):883-889, 2000.
Hotta, "New concepts and insights on pathogenesis and treatment of diabetic complications: polyol pathway and its inhibition," NagoyaJ. Med. Sci. 60:89-100, 1997.
Hsu et al., "Differential cotrol of murine aldose reductase and fibroblast growth factor (FGF)-regulated-I gene expression in NIH 3T3 cells by FGF-1 treatment and hyperosmotic stress," Biochem. J. 328:593-598, 1997.
Inan et al., "Prevention of posterior capsule opacification by retinoic acid and mitomycin," Graefes. Arch. Clin. Exp. Ophthalmol., 239:693-697, 2001.
Iyengar et al., "Duration ofERKI/2 phosphorylation induced by FGF or ocular media determines lens cell fate," Differentiation, 75:662-668, 2007.
Jacquin-Beeker et al., "Regulation of aldose reductase expression in rat astrocytes in culture," GLIA. 20:135-44, 1997.
Jen and Gewirtz, "Suppression of gene expression by targeted disruption of messenger RNA: available options and current strategies," Stem Cells, 18:307-19,2000.
Jez et al., "Comparative anatomy of the aldo-keto reductase superfamily," Biochem. J. 326:625-636, 1997.
Jiang et al., "EGF-induced cell migration is med_iated by ERK and PI3K/AKT pathways in cultured human lens epithelial cells," J. Ocul. Pharmacal. Ther., 22:93-102, 2006.
Joseph et al., "Infliximab in the treatment of refractory posterior uveitis," Ophthalmology, 110:1449-1453,2003.
Jourd'heuil et al., "Oxidants, transcription factors, and intestinal inflammation," J. Clin. Gastroenterol. 25 :S61-S72, 1997.
Kador et al., "The pharmacology of aldose reductase inhibitors," Annu. Rev. Pharmacal. Toxicol. 25:691-714, 1985.
Ramana et al., "Aldose reductase mediates the mitogenic signals of cytokines," Chern. Bioi. Interact., 143-144:587-596,2003.
Ramana et al., "Aldose reductase regulates TNF-alpha-induced cell signaling and apoptosis in vascular endothelial cells," FEES Lett., 570:189-194, 2004.
Ramana et al., "Endotoxin-induced cardiomyopathy and systemic inflammation in mice is prevented by aldose reductase inhibition," Circulation, 114:1838-1846, 2006.
Raman A et al., "Inhibition of aldose reductase attenuates TNF-alpha-induced expression of adhesion molecules in endothelial cells," FASEB J, 18:1209-1218, 2004.
Ramana et al., "Mitogenic responses of vascular smooth muscle cells to lipid peroxidationderived aldehyde 4-hydroxy-trans-2-nonenal (HNE): role of aldose reductase-catalyzed reduction of the HNE-glutathione conjugates in regulating cell growth," J Bioi. Chern., 281:17652-17660, 2006.
Ramana et al., "Requirement of aldose reductase for the hyperglycemic activation of protein kinase C and formation of diacylglycerol in vascular smooth muscle cells," Diabetes, 54:818-829,2005.
Ramana et al., "Selective recognition of glutathiolated aldehydes by aldose reductase," Biochemistry, 39:12172-12180,2000.
Rath et al., "TNF-induced signaling in apoptosis," J. Clin. Immunol,. 19:350-364, 1999.
Recchia, "Role of nitric oxide in the regulation of substrate metabolism in heart faliure," Heart. Fail. Rev., 7:141-148,2002.
Rectenwald et al., "Direct evidence for cytokine involvement in neointimal hyperplasia," Circulation 102:1697-1702,2000.
Riffo-Vasquez and Spina, "Role of cytokines and chemokines in bronchial hyperresponsiveness and airway inflammation," Pharmacal.. Ther, 94:185-211, 2002.
Rittner et al., "Aldose reductase functions as a detoxification system for lipid peroxidation products in vasculitis," J. Clin. Invest, 103:1007-13, 1999.
Rosi et al., "Perception of airway obstruction and airway inflammation in asthma: a review." Lung., 184:251-8, 2006.
Ruderman et al., "Glucose and diabetic vascular disease," FASEB J., 6:2905-2914, 1992.
Ruef et al., "Involvement of aldose reductase in vascular smooth muscle cell growth and lesion formation after arterial injury," Arterioscler. Thromb. Vase. Biol., 20:1745-52, 2000.
Ryden et al., "Mapping of early signaling events in tumor necrosis factor-a-mediated lipolysis in human fat cells," J. Bioi. Chern. 277(2): 1085-1091, 2002.
Saraste and Pullki, "Morphologic and biochemical hallmarks of apoptosis," Cardiovas. Res., 45:528-537, 2000.
Schiavone et al., "Antisense oligonucleotide drug design," Curr. Pharma. Des., 1004:769-84, 2004.
Selzman et al., "Liposomal delivery of purified inhibitory-KBa inhibits tumor necrosis factor-ainduced human cascular smooth muscle proliferation," Circ. Res., 84:867-875, 1999.
Seo et al., "Lipoprotein lipase-mediated selective uptake from low density lipoprotein requires cell surface proteoglycans and is independent of scavenger receptor class B type 1 ," J. Bioi. Chern., 275:30355-62, 2000.
Seo et al., "Nitric oxide up-regulates aldose reductase expression in rat vascular smooth muscle cells: a potential role for aldose reductase in vascular remodeling," Mol. Pharmacal., 57:709-717,2000.
Sheetz and King, "Molecular understanding of hyperglycemia's adverse effects for diabetic complications," JAMA, 288:2579-2588, 2002.
Shinmura et al., "Aldose reductase is an obligatory mediator ofthe late phase of ischemic preconditions," Circulation Research, 91 :240-6, 2002.
Shinmura et al., "Cyclooxygenase-2 mediates the cardioprotective effects of the late phase of ischemic preconditioning in conscious rabbits," Proc. Nat!. A cad Sci. USA, 97: I 0197-202, 2000.
Singh et al., "Structure of a glutathione conjugate bound to the active site of aldose reductase," Proteins, 64:101-10, 2006.
Smith et al., "An aldose reductase inhibitor inhibits inflammation," Clin. Res., 34:507A, 1986.
Spycher et al., "Aldose reductase induction: a novel response to oxidative stress of smooth muscle cells," FASEBJ, 11:181-8,1997.
Srivastava et al., "Activated and unactivated forms of human erythrocyte aldose reductase," Proc. Nat!. Acad.Sci. USA., 82:7222-7226, 1985.
Srivastava et al., "Contribution of aldose reductase to diabetic hyperproliferation of vascular smooth muscle cells," Diabetes, 55:901-910, 2006.
Srivastava et al., "Identification of biochemical pathways for the metabolism of oxidized lowdensity lipoprotein derived aldehyde-4-hydroxy trans-2-nonenal in vascular smooth muscle cells," Atherosclerosis, 18:339-350,2001.
Srivastava et al., "Involvement of aldose reductase in the metabolism of atherogenic aldehydes," Chemica-Biological Interactions, 130-132:563-571, 2001.
Srivastava et al., "Kinetic studies of FR-1, a growth factor-inducible aldo-keto reductase," Biochemistry, 37:12909-17, 1998.
Srivastava et al., "Lipid peroxidation product, 4-hydroxynonenal and its conjugate with GSH are excellent substrates of bovine lens aldose reductase," Biochem. Biophys. Res. Commun., 217:741-46, 1995.
Srivastava et al., "Metabolism of the lipid peroxidation product, 4-hydroxy-trans-2-nonenal, in isolated perfused rat heart," J Biol. Chern., 273:10893-10900, 1998.
Srivastava et al., "Regulation of aldose reductase by aldehydes and nitric oxide," A dv. Exp. Med. Biol., 463:501-7, 1999.
Srivastava et al., "Role of aldose reductase and oxidative damage in diabetes and the consequent potential for therapeutic options," Endocr. Rev., 26:380-392, 2005.
Srivastava et al., "Structural and kinetic determinants of aldehyde reduction by aldose reductase," Biochemistry, 38:42-54, 1999.
Srivastava et al., "Structural and kinetic modifications of aldose reductase by S-nitrosothiols," Biochem J., 358:111-118, 2001.
Symonds et al., "Posterior capsule opacification-like changes in rat lens explants cultured with TGFbeta and FGF: effects of cell coverage and regional differences," Exp. Eye Res., 82:693-699,2006.

(56) References Cited

OTHER PUBLICATIONS

Taketa!., "NF-KB: a key role in inflammatory diseases," J Clin. Invest., 107:7-11, 2001.

Tammali et al., "Aldose reductase regulates growth factor-induced cyclooxygenase-2 expression and prostaglandin E2 production in human colon cancer cells," Cancer Res., 66:9705-9713, 2006.

Terry et al., "TNF-a and IL-I a induce heme oxygenase- I via protein kinase C, Ca2+, and phospholipase A2 in endothelial cells," Am. J Physiol. 276:HI493-HI501, 1999.

Tesfamariam et al., "Aldose reductase inhibition restores endothelial cell function in diabetic rabbit aorta," J Cardiovasc. Pharmacal., 21:205-11, 1993.

Torreilles, "Nitric oxide:one of the more conserved and widespread signaling molecules,"Front. Biosci. 6:DII61-DII72, 2001.

Traverse et al., "Inhibition of NO production increases myocardial blood flow and oxygen consumption in congestive heart faliure," Am. J Physiol. Heart. Circ. Physiol. 282:H2278-H2283, 2002.

Trouillet et al., "Ventilator-associated Pneumonia caused by potentiaiJy drug-resistant bacteria," Am. J Respir. Crit. Care Med., 157:531-9, 1998.

U.S. Appl. No. I 0/462,223, "Methods and Compostions Involving Aldose Reductase Inhibitors," by Satish K. Srivastava etal., filed Jun. 13, 2003.

U.S. Appl. No. 11/210,283, "Methods Involving Aldose Reductase Inhibitors," by Satish K. Srivastava eta!., filed Aug. 23, 2005. CI49 van Goor eta!., Nitric oxide inhibition enhances platelet aggregation in experimental.

van Goor et al., "Nitric oxide inhibition enhances platelet aggregation in experimental anti-thy-1 nephritis," Nitric Oxide 5:525-33, 2001.

Vander Jagt et al., "Substrate specificity of human aldose reductase: identification of 4-hydroxynonenal as an endogenous substrate," Biochim. Biophys. Acta., 1249:117-26, 1995.

Beers & Berkow, "The Merck Manual of Diagnosis and Therapy" $17^{th}$ ed. Merck Res Lab, pp. 725-9, 1999.

Fernyhough, et al., "Stimulation of nerve growth factor and substance P expression in the iris-trigeminal axis of diabetic rats-involvement of oxidative stress and effects of aldose reductase inhibition," Brain Res. 802(1-2):247-53, 1998.

Kisanuki, et al., "Jutoku na Kosaien o Tomonatta Tonyobyo Kakumakusho No 2 Rei./Two Cases of Diabetic Ketatophathy with Severe Iritis" Folio Ophthalmologica Japonica. 46(1):268-271, 1995. English Abstract only.

Romero, et al., "Pharmacologic Modulation of Acute Ocular Inflammation with Quercetin" Ophthalmic Res. 21(2):112-117, 1989.

Yadav, et al., "Amelioration of Experimental Autoimmune Uveoretinitis by Aldose Reductase Inhibition in Lewis Rats," Investigative Ophthalmology & Visual Science. 52(11):8033-8041, 2011.

Extended European Search Report in European Application No. 14185108.9 dated May 20, 2015.

Office Action in Canadian Application No. 2,685,202 dated Jan. 7, 2015.

Office Action in Indian Application No. 6803/DELNP/2009 dated Apr. 23, 2015.

\* cited by examiner

METHODS INVOLVING ALDOSE REDUCTASE INHIBITORS

This application is a divisional of U.S. patent application Ser. No. 12/532,553 filed Sep. 22, 2009; which is a 371 national stage filing of international Application PCT/US2008/057998 filed Mar. 24, 2008; which claims priority to U.S. Provisional Application No. 60/896,752 filed Mar. 23, 2007. Priority is claimed to each of the above referenced applications and the entire contents of each of the above-referenced applications is incorporated herein by reference in its entirety.

This invention was made with government support under grants R01 GM071036 and R34 DK036118 awarded by the National Institutes of Health. The government has certain rights in the invention.

BACKGROUND OF THE INVENTION

I. Field of the Invention

Embodiments of this invention are related generally to physiology and medicine. More specifically, this invention is related to aldose reductase inhibitors (ARIs) and their use in treating and ameliorating inflammation.

II. Background

Aldose reductase (AR) catalyzes the reduction of a wide range of aldehydes (Bhatnager and Srivastava, 1992). The substrates of the enzyme range from aromatic and aliphatic aldehydes to aldoses such as glucose, galactose, and ribose. The reduction of glucose by AR is particularly significant during hyperglycemia and increased flux of glucose via AR has been etiologically linked to the development of secondary diabetic complications (Bhatnager and Srivastava, 1992; Yabe-Nishimura, 1998). However, recent studies showing that AR is an excellent catalyst for the reduction of lipid peroxidation-derived aldehydes and their glutathione conjugates (Srivastava et al., 1995; Vander Jagt et al., 1995; Srivastava et al., 1998; Srivastava et al., 1999; Dixit et al., 2000; Ramana et al., 2000) suggest that in contrast to its injurious role during diabetes, under normal glucose concentration, AR may be involved in protection against oxidative and electrophilic stress. The antioxidant role of AR is consistent with the observations that in a variety of cell types AR is upregulated by oxidants such as hydrogen peroxide (Spycher et al., 1997), lipid peroxidation-derived aldehydes (Ruef et al., 2000; Rittner et al., 1999), advanced glycosylation end products (Nakamura et al., 2000) and nitric oxide (Seo et al., 2000). The expression of the enzyme is also increased under several pathological conditions associated with increased oxidative or electrophilic stress such as iron overload (Barisani et al., 2000), alcoholic liver disease (O'Connor et al., 1999), heart failure (Yang et al., 2000), myocardial ischemia (Shinmura et al., 2000), vascular inflammation (Rittner et al., 1999) and restenosis (Ruef et al., 2000), and various forms of cancer.

Inhibitors of aldose reductase have been indicated for some conditions and diseases, such as diabetes complications, ischemic damage to non-cardiac tissue, Huntington's disease. See U.S. Pat. Nos. 6,696,407, 6,127,367, 6,380,200, which are all hereby incorporated by reference. In some cases, the role in which aldose reductase plays in mechanisms involved in the condition or disease are known. For example, in U.S. Pat. No. 6,696,407 indicates that an aldose reductase inhibitors increase striatal ciliary neurotrophic factor (CNTF), which has ramifications for the treatment of Huntington's Disease. In other cases, however, the way in which aldose reductase or aldose reductase inhibitors work with respect to a particular disease or condition are not known.

Therefore, the role of aldose reductase in a number of diseases and conditions requires elucidation, as patients with these diseases and conditions continue to require new treatments. Thus, there is a need for preventative and therapeutic methods involving aldose reductase and aldose reductase inhibitors.

SUMMARY OF THE INVENTION

Embodiments of the invention are directed to methods of preventing or reducing uveitis or conjuctivitis in a subject comprising administering to a subject diagnosed with or at risk of developing uveitis or conjunctivitis an amount of a pharmaceutically acceptable composition comprising an aldose reductase inhibitor (ARI) sufficient to prevent, ameliorate, or attenuate uveitis or conjunctivitis. The composition may be administered 1, 2, 3, 4, 5, 6, or more times and may be administered over 1, 2, 3, 4, 5, 6, 7, or more minutes, hours, days or weeks. In certain aspects, the aldose reductase inhibitor is administered to the patient as a prodrug. Typically, prodrug is an inactive or less active form of a drug that is metabolized or converted in vivo to an active or more active form. ARI compositions can be administered directly, locally, topically, orally, ocularly, endoscopically, intratracheally, intravitreously, intrabronchially, intratumorally, intravenously, intralesionally, intramuscularly, intraperitoneally, regionally, percutaneously, or subcutaneously. In a particular aspect the ARI is administered orally or by inhalation or instillation, e.g., by inhaler or other aersol delivery devices.

Other embodiments of the invention are directed to methods of preventing or reducing asthma associated inflammation in a subject comprising administering to a subject diagnosed with or at risk of developing an inflammatory condition associated with asthma an amount of a pharmaceutically acceptable composition comprising an aldose reductase inhibitor sufficient to prevent, ameliorate, or attenuate inflammation.

In certain embodiments the aldose reductase inhibitor is a peptide, a peptide mimetic, a small molecule, or an inhibitory RNA. The aldose reductase inhibitor can be a siRNA or other inhibitory nucleic acid, a carboxylic acid, a hydantoins, a pyridazinone, or a pharmaceutically acceptable derivative thereof. In particular aspects the aldose reductase inhibitor is sorbinil, epalrestat, ponalrestat, methosorbinil, risarestat, imirestat, ALO-1567, quercetin, zopolrestat, AD-5467, NZ-314, M-16209, minalrestat, AS-3201, WP-921, luteolin, tolrestat, EBPC, fidarestat, siRNA, or a pharmaceutically acceptable derivatives thereof. In certain embodiments the aldose reductase inhibitor is sorbinil or zopolrestat. The aldose reductase inhibitor can be administered at a dose of 0.1, 1, 5, 10, 20, 40, 50, 100, 200, 400, 800, 1200 to 1500 ng/day, mg/day, ng/kg/day, or mg/kg/day, including all ranges and values there between.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Histo-pathological changes in the anterior chamber of EIU rat eyes in the absence and presence of Sorbinil or zopolrestat. Serial sections of para-formaldehyde-fixed rat eyes were stained with Hematoxylin and Eosin (H&E) and observed under light microscope (Magnification 200×). (FIG. 1B I) The inflammatory cells and (FIG. 1B II) total protein concentration in the AqH were measured using trypan-blue exclusion cell counting and Bradford methods, respectively as described in the Methods. Results are given as mean±SD (n=6); #p<0.001 and ##p<0.05 Vs Control group; *p<0.01 and **p<0.001 Vs EIU-group. AqH, Aqueous humor; CB, ciliary body; I, Iris; C, cornea; R, Retina; V, Vitrious.

(FIG. 2A) TNF-α levels in the AqH collected after 6 and 24 h after LPS injection were measured by using ELISA kit as described in the Methods. Each value represents mean±SD (n=4); #p<0.001 vs control group and *p<0.001 vs EIU-group. (FIG. 2B) Serial sections of para-formaldehyde-fixed rat eyes were immuno-stained with antibodies against TNF-α and observed under EPI-800 microscope (A represen- tative picture is shown (n=4); Magnification 200×). AqH, Aqueous humor; CB, Ciliary body; I, Iris; C, Cornea; V, Vitreous; R, Retina.

(FIG. 4A) Serial sections of para-formaldehyde-fixed rat eyes, enucleated 24 h after EIU-induction, were immuno-stained with antibodies against AR (FIG. 4A) and serial sections of para-formaldehyde-fixed rat eyes, enucleated 3 h after EIU-induction, were immuno-stained with antibodies against active NF-κB (phospho-p65) antibodies (FIG. 4B) as described in the Methods. The antibody staining intensity was observed under EPI-800 microscope (A representative picture is shown (n=4); Magnification 200× (FIG. 4A) and 400× (FIG. 4B)). AqH, Aqueous humor; CB, ciliary body; C, Cornea; R, Retina.

(FIG. 6A). Growth arrested U-937 cells without or with zopolrestat (10 μM each) were incubated with 1 μg/ml of LPS for 24 h. The expression of Cox-2 and iNOS proteins was determined by western blot analysis using specific antibodies as described in the Methods. (FIG. 6B). U-937 cells were transiently transfected with pNF-κB-SEAP reporter vector. The cells treated without or with sorbinil and zopolrestat (10 μM each) were incubated with 1 μg/ml of LPS. After 24 h the culture supernatants were assayed for SEAP activity using chemiluminescence kit according to supplier's instructions. Data represents mean±SD (n=6). #p<0.01 vs control group; ##p<0.01 vs LPS group.

(FIG. 8A) The lungs were lavaged with ice-cold PBS and cells were counted and (inset) differential cell counts were performed on cytocentrifuge preparations stained with hematoxylin and eosin. (FIG. 8B) Perivascular and peribronchial inflammation and cell composition in the BAL were evaluated by a pathologist blinded to treatment groups to obtain data for each lung.

(FIG. 9A) MUC5AC levels in the BAL assessed by ELISA using anti-MUC5AC monoclonal antibody and (inset in A) mucin productions in the epithelial cells was assessed by periodic acid Schiff (PAS)-staining of lung sections. (FIG. 9B) Airway responsiveness was measured in unrestrained, conscious mice 3 days after the last challenge. Mice will be placed in a barometric plethysmographic chamber, and baseline readings will be taken and averaged for 3 min. Aerosolized methacholine in increasing concentrations (from 2.5 to 50 mg/ml) were nebulized through an inlet of the main chamber for 3 min. Readings were taken and averaged for 3 min after each nebulization and enhanced pause (Penh) was determined. Penh, calculated as (expiratory time/relaxation time−1)×(peak expiratory flow/peak inspiratory flow) according to the manufacturers' protocol. Penh was used as a measure of airway responsiveness to methacholine.

(FIG. 10A) Cytokine levels in BAL fluids were measured using the Bio-Rad Bioplex system. Data are given as means±SD (n=4)*, difference from unchallenged mice, $p<0.01$; #, difference from wild type mice challenged with OVA, $p<0.01$. (FIG. 10B) Fixed lungs from the different experimental groups were sectioned, stained with hematoxylin and eosin. Arrows indicate sites of inflammatory cell infiltration.

(FIG. 11A) Growth-arrested SAEC, pretreated without or with zopolrestat (20 μM), were incubated with 150 μg/ml of RW for 18 h to induce apoptotic cell death. The cells were stained with annexin-V FITC (FL-1) and propidium iodide (PI) (FL-2). R1 denotes dead cells (PI positive) and R2 represents early apoptotic cells (annexin-V positive) and R1+R2 represents total dead cells. (FIG. 11B) The data from (A) has been plotted as bar diagram (n=4, $*P<0.01$ Control vs. RWP; $**P<0.01$ RW vs. Zop+RW).

(FIG. 17A). For EMSA, approximately $2\times10^6$ SAEC were seeded in T-150 cm$^2$ flasks and incubated until 80% confluency. The cells were starved in serum-free basal medium with or without zopolrestat for 24 h. The cells were treated with RW (50 μg/ml) for 3 h. Nuclear extract was prepared as described in the methods and EMSA was performed to determine the activation of NF-κB and AP-1. Lanes: 1, Control; 2, Ragweed; 3, Control+Zop; 4, RW+Zop. (FIG. 17B). Approximately, $1\times10^5$ SAEC were plated in 24 well plate and growth-arrested by preincubatin in serum-free basal medium with AR inhibitors or carrier for 24 h followed by transfection with NF-κB-pSEAP vector or control (pTAL) vector. After 6 h, transfected cells were incubated with RW (50 μg/ml) for 48 hours. Medium was collected and NF-κB-dependent reporter SEAP activity was measured by chemiluminescence method essentially as described by the manufacturer. Bars represent Mean±SD (n=4). #$p<0.001$ Vs. Control; *$p<0.01$ vs RW.

(FIG. 18A) The BALB/c mice were sensitized and challenged with RW, subsequently lungs were lavaged with ice-cold PBS and cells were counted and differential cell counts were performed on cytocentrifuge preparations stained with hematoxylin and eosin (inset in FIG. 18A). (FIG. 18B) Perivascular and peribronchial inflammation and cell composition in the BAL fluid were evaluated. A representative picture is shown (n=4-6).

(FIG. 19A) MUC5AC levels in the BAL were assessed by ELISA using anti-MUC5AC monoclonal antibody and mucin productions in the epithelial cells was assessed by periodic acid Schiff (PAS)-staining of lung sections (inset in FIG. 19A). (FIG. 19B) Airway responsiveness was measured in unrestrained, conscious mice 3 days after the last challenge. Mice were placed in a barometric plethysmographic chamber, and baseline readings were taken and averaged for 3 min. Aerosolized methacholine in increasing concentrations (from 10 to 80 mg/ml) were nebulized through an inlet of the main chamber for 3 min. Readings were taken and averaged for 3 min after each nebulization and enhanced pause (Penh) was determined and plotted against the increasing concentration of methacholine as a measure of airway responsiveness to methacholine. Penh, calculated as (expiratory time/relaxation time$^{-1}$)×(peak expiratory flow/peak inspiratory flow) according to the manufacturers' protocol.

Figure 20:
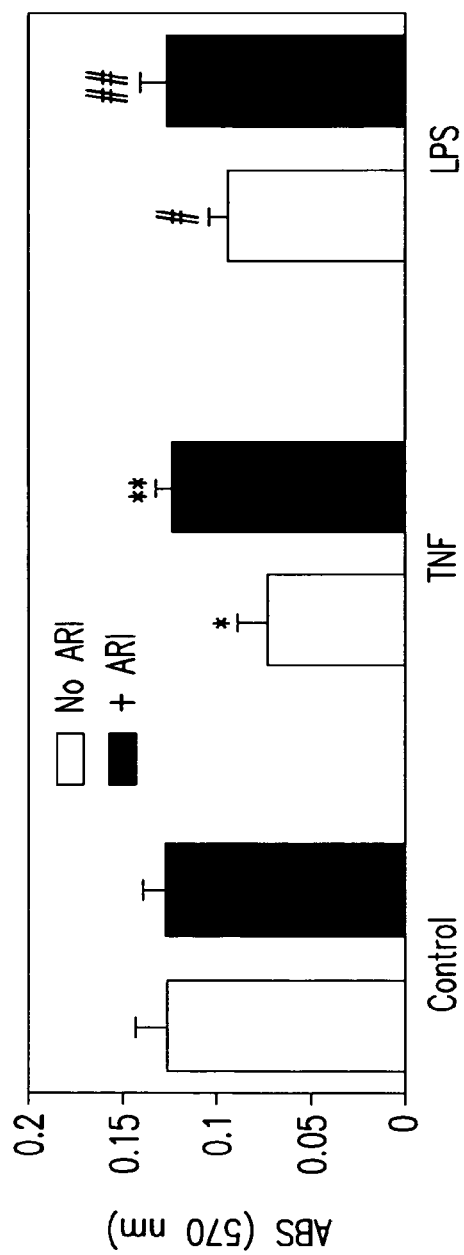

FIG. 20 Inhibition of AR prevents TNF-α- and LPS-induced cell death in SAEC. Approximately 5000 cells were seeded in 96-well plate and incubated until 80% confluence. Medium was replaced with basal medium with sorbinil (20 μM) or carrier (DMSO) for 24 h. The cells were incubated with TNF-α (2 nM) and LPS (1 μg/ml) for further 24 h. At the end of incubation 10 μl MTT (5 mg/ml) was added and incubated for 2 h. Medium was removed and 100 μl DMSO was added to each well and absorbance was read at 570 nm. Bars represent mean±SD (n=4); *P<0.01Vs Control; **P<0.01 Vs TNF-α; #P<0.05 Vs Control; ##P<0.05 Vs LPS.

Figure 21A:
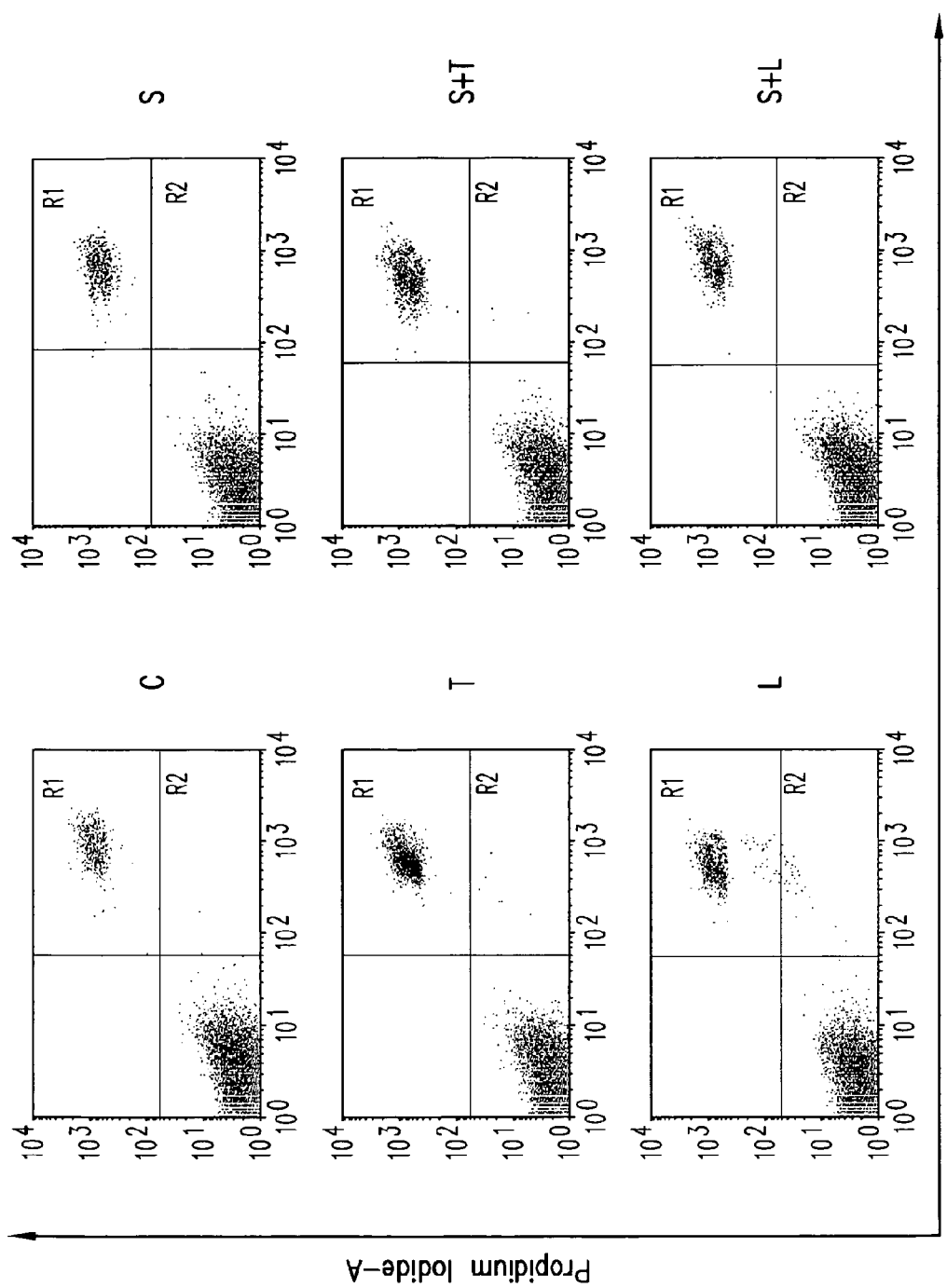
Figure 21B:
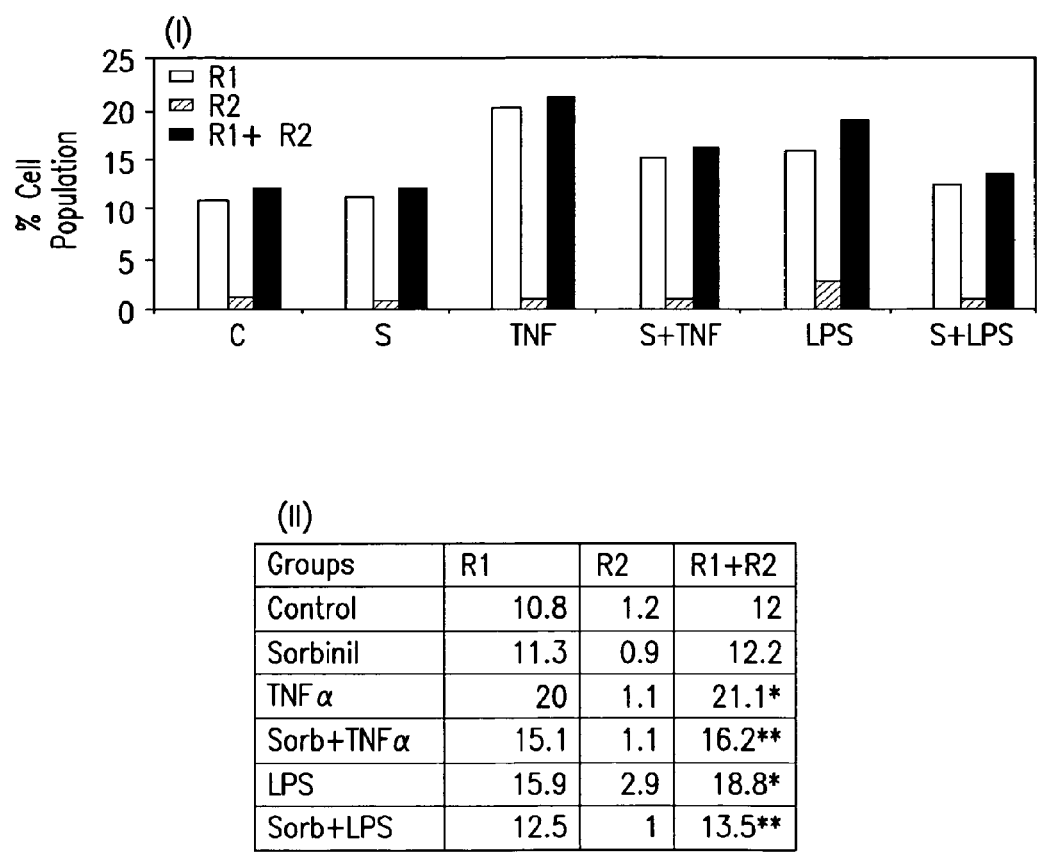

FIGS. 21A-21B Inhibition of AR prevents TNF-α- and LPS-induced apoptosis and cell death in SAEC. (FIG. 21A) Approximately 2×10$^5$ SAEC were seeded on 6 well plates (4 well per group) and growth arrested with sorbinil (20 μM) or carrier (DMSO). Subsequently, the cells were incubated with TNF-α or LPS for 18 h. The cells were harvested, pooled together and stained with annexin V-FITC (FL-1) and propidium iodide (PI) (FL-2). R1 represents dead cells (PI positive) and R2 denotes early apoptotic cells (annexin-V positive) and R1+R2 represents total dead cells. (FIG. 21B) The data in A was plotted as bar diagram (FIG. 21B(I)) and also tabulated (FIG. 21B(II)). The bars represent mean±SD (n=4); (*P<0.05 vs. Control; **P<0.05 vs. TNF-α/LPS).

Figure 22:
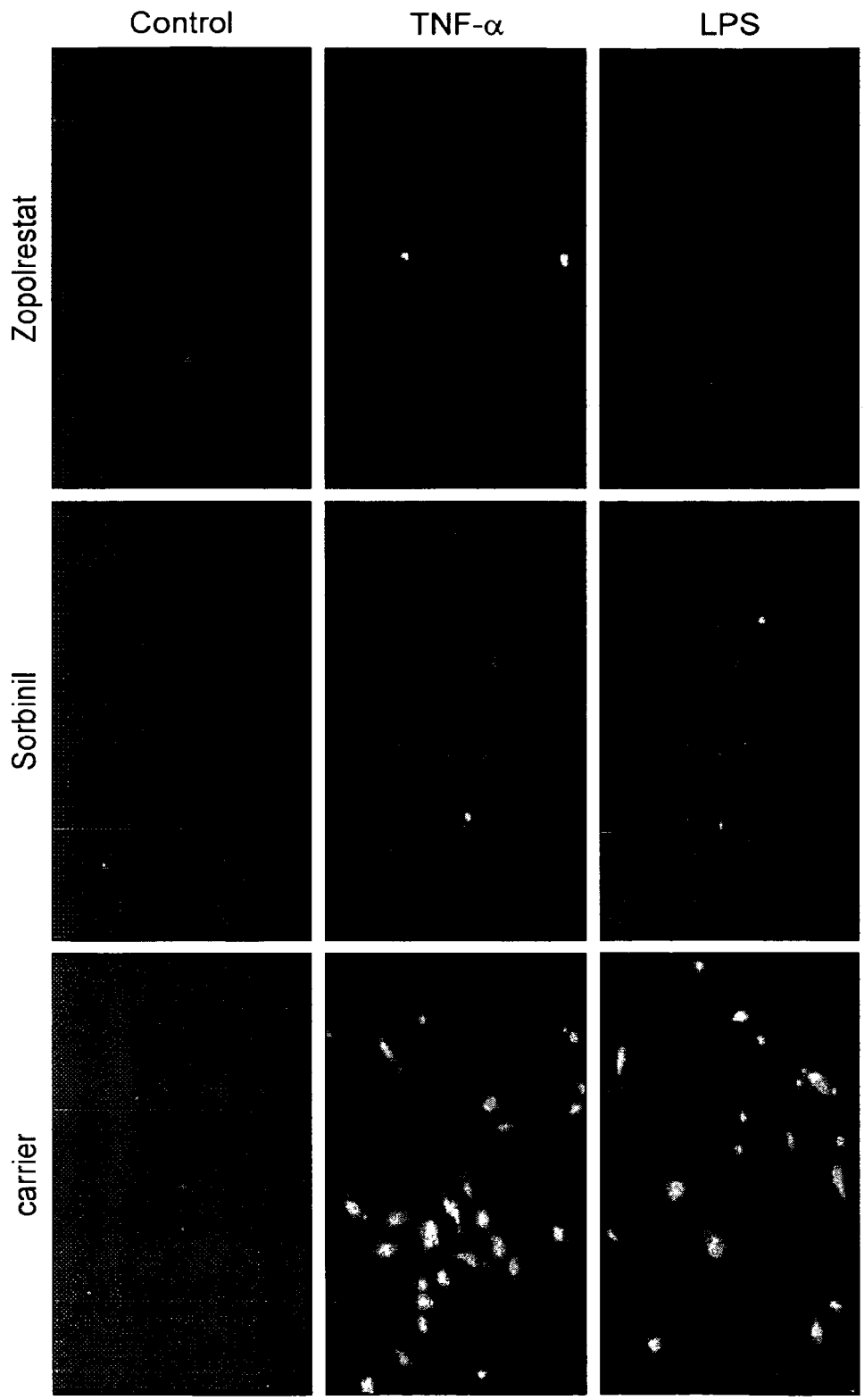

FIG. 22 Inhibition of AR prevents TNF-α- and LPS-induced ROS generation in SAEC. Approximately 1×10$^5$ cells were seeded on chambered slides and after the cells attached they were starved in serum free basal medium with AR inhibitor or carrier (DMSO) for overnight. The cells were treated with TNF and LPS or carrier (PBS) for 16 h. The cells were washed with cold PBS (pH 7.2) and stained with ROS-sensitive dye dihydroethidium (DHE) for 15 min at 37° C. The cells were washed again and mounted with floursave (with DAPI) mounting medium. For the acquisition of images a fluorescence microscope (Nikon) was used. A representative picture is shown (n=4); Magnification 200×.

Figure 23:
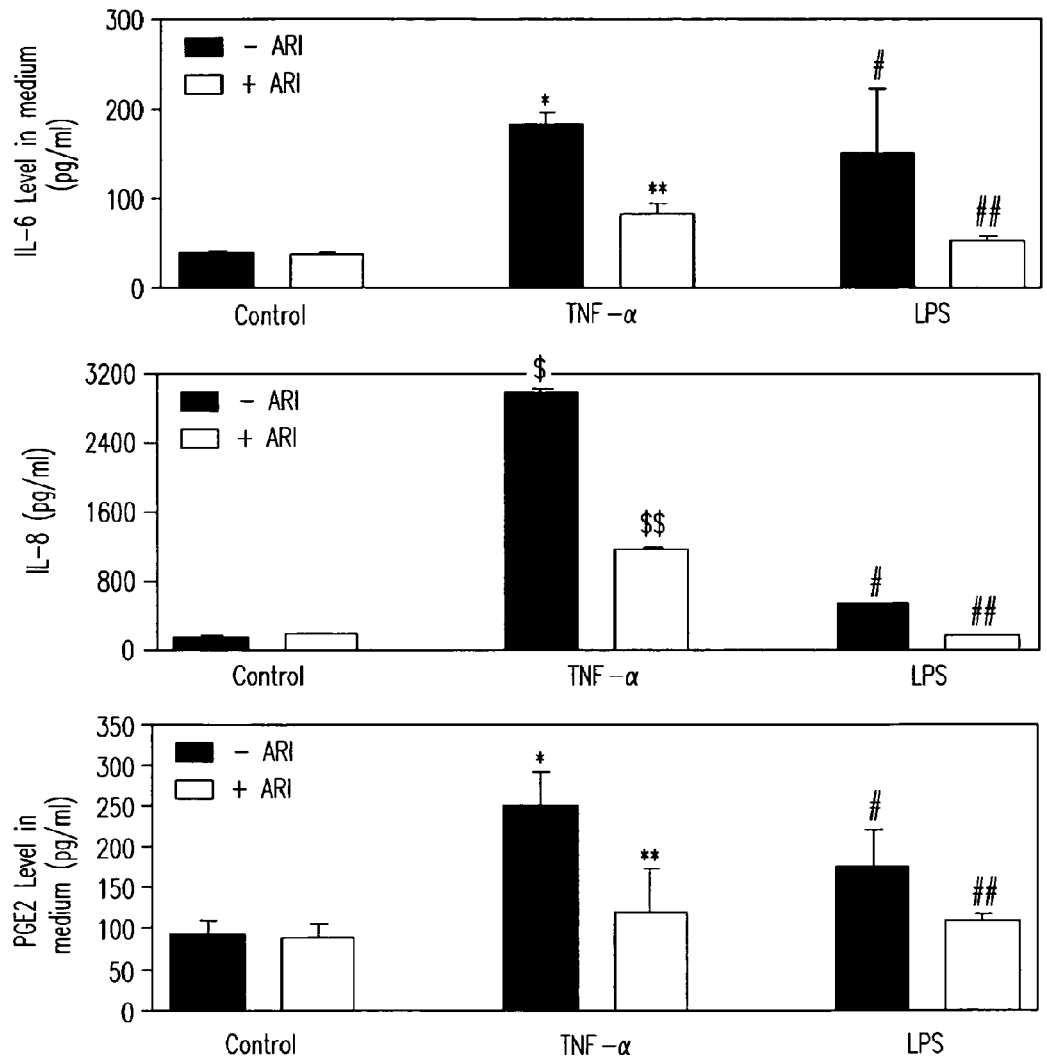

FIG. 23 AR inhibition prevents TNF-α- and LPS-induced secretion of inflammatory markers IL-6, IL-8 and PGE2. Approximately 2×10$^5$ cells were seed in 6-well plates and incubated until 80% confluence. Medium was replaced with basal medium with AR inhibitor or carrier for overnight. The cells were treated with TNF-α (2 nM) and LPS (1 μg/ml) and incubated for 24 h. Medium was harvested, centrifuged and supernatant was used for determination of IL-6, IL-8 and PGE2 with respective ELISA kits following supplier's protocol. Bars represent Mean±SD (n=4); *p<0.01 Vs Control; **p<0.01 Vs TNF-α alone; #p<0.05 Vs Control; ##p<0.05 Vs LPS alone $p<0.001 Vs Control; $$p<0.01 Vs TNF alone.

Figure 24A:
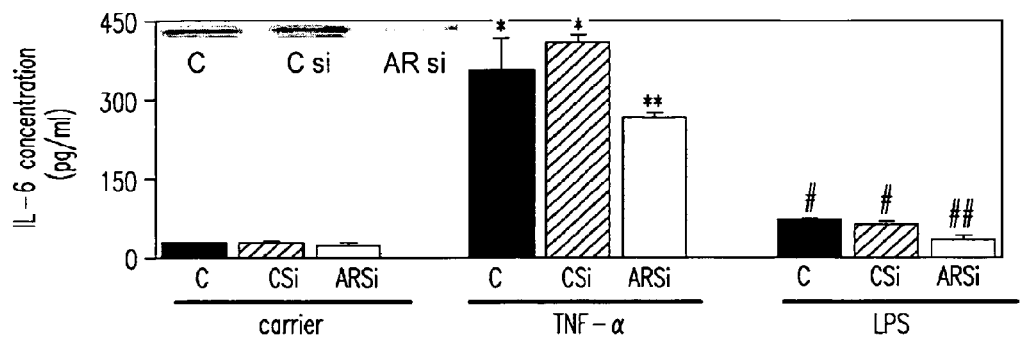
Figure 24B:
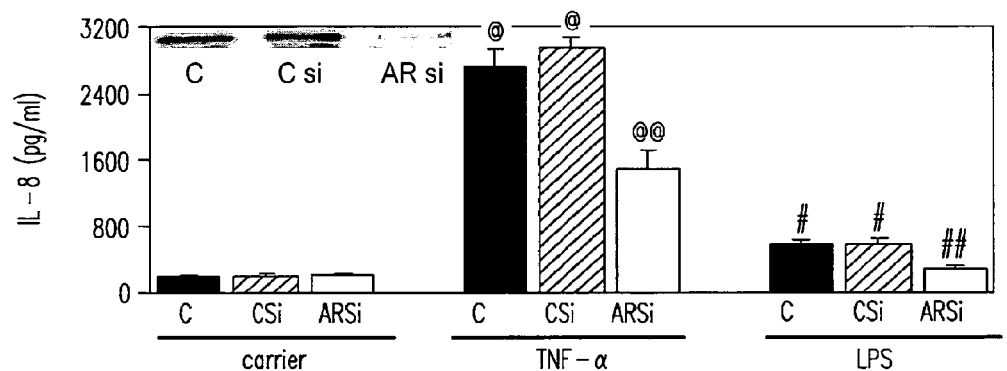
Figure 24C:
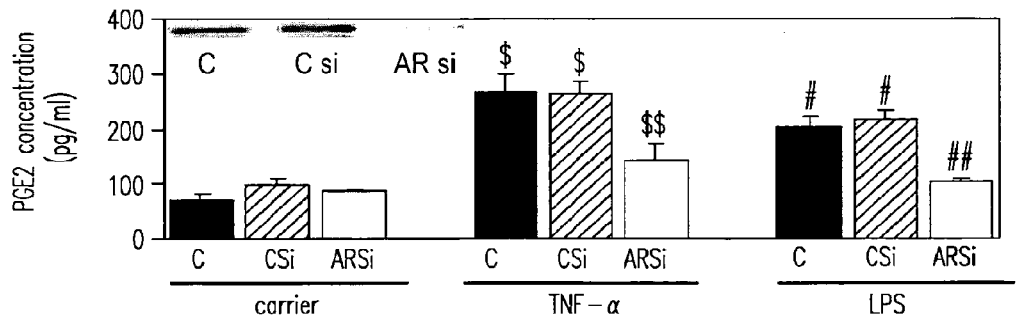

FIGS. 24A-24C AR ablation by siRNA prevents TNF-α- and LPS-induced secretion of inflammatory markers IL-6, IL-8 and PGE2. The SAEC (~2×10$^5$) were seeded in 6-well plates and incubated until 80% confluence. Medium was replaced with basal medium and cells were transfected with either AR-siRNA or scrambled-siRNA. After 48 h cells were incubated with TNF-α (2 nM) or LPS (1 μg/ml) for additional 24 h. At the end of incubation medium was harvested, centrifuged and supernatant was used for determination of IL-6, IL-8 and PGE2 with respective ELISA kits following supplier's protocol. Inset shows expression of AR in control and siRNA transfected cell as determined by Western blotting. Bars represent Mean±SD (n=4 *p<0.001 Vs Control; **p<0.01 Vs TNF-α alone; @p<0.0005 Vs Control; @@p<0.001 Vs TNF-α alone; $p<0.001 Vs Control; $$p<0.01 Vs TNF-α alone; #p<0.005 Vs Control; ##p<0.01 Vs LPS alone.

Figure 25:
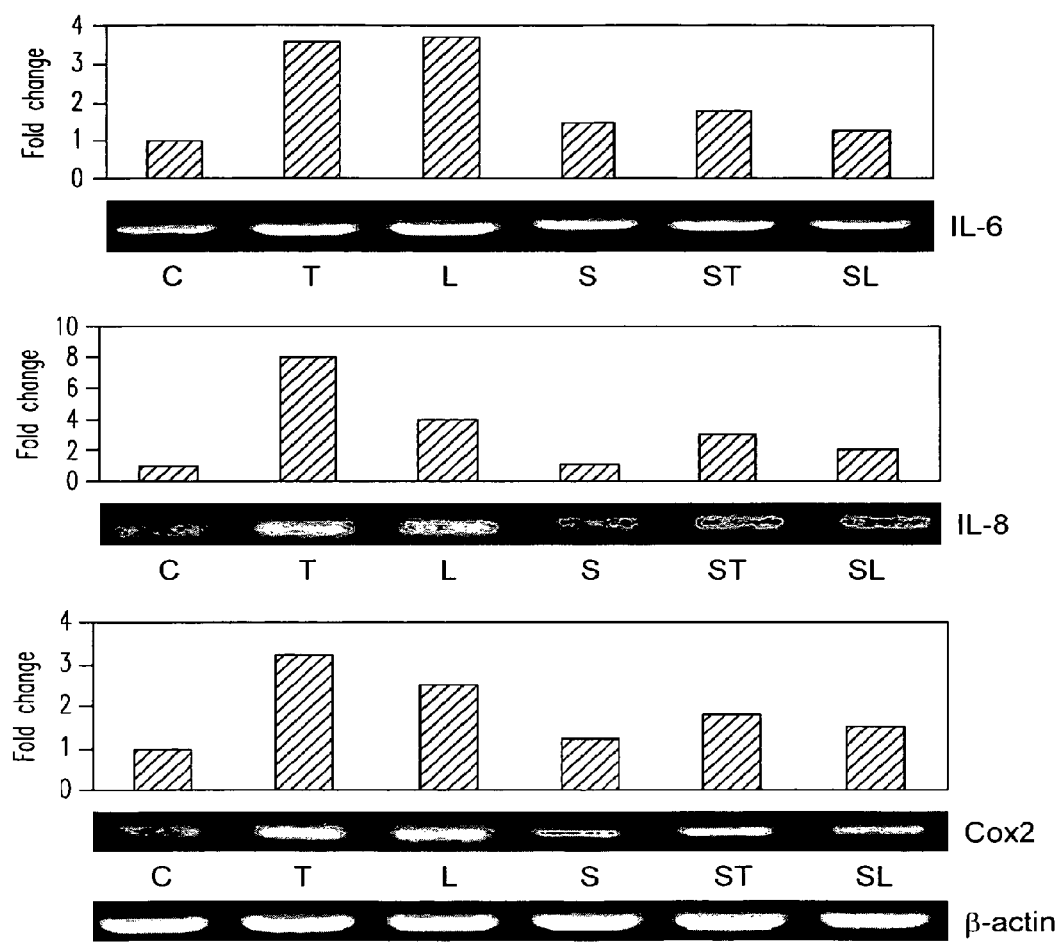

FIG. 25 AR inhibition prevents TNF-α- and LPS-induced expression of inflammatory markers IL-6 and IL-8 and COX-2. Approximately 2×10$^5$ SAEC were seeded in 6-well plates and incubated until 80% confluence. Medium was replaced with basal (serum-free) medium with AR inhibitor or carrier and incubated for 24 h. The cells were treated with TNF-α (2 nM) and LPS (1 μg/ml) for an additional 6 h. Total RNA was extracted as described in the methods and levels of expression of IL-6, IL-8 and Cox-2 mRNA was determined using Qiagen RT-PCR kit. β-Actin was used as loading control. The bar diagram above each blot represents relative fold change in band intensity. C, Control; T, TNF-α; L, LPS; S, sorbinil.

Figure 26:
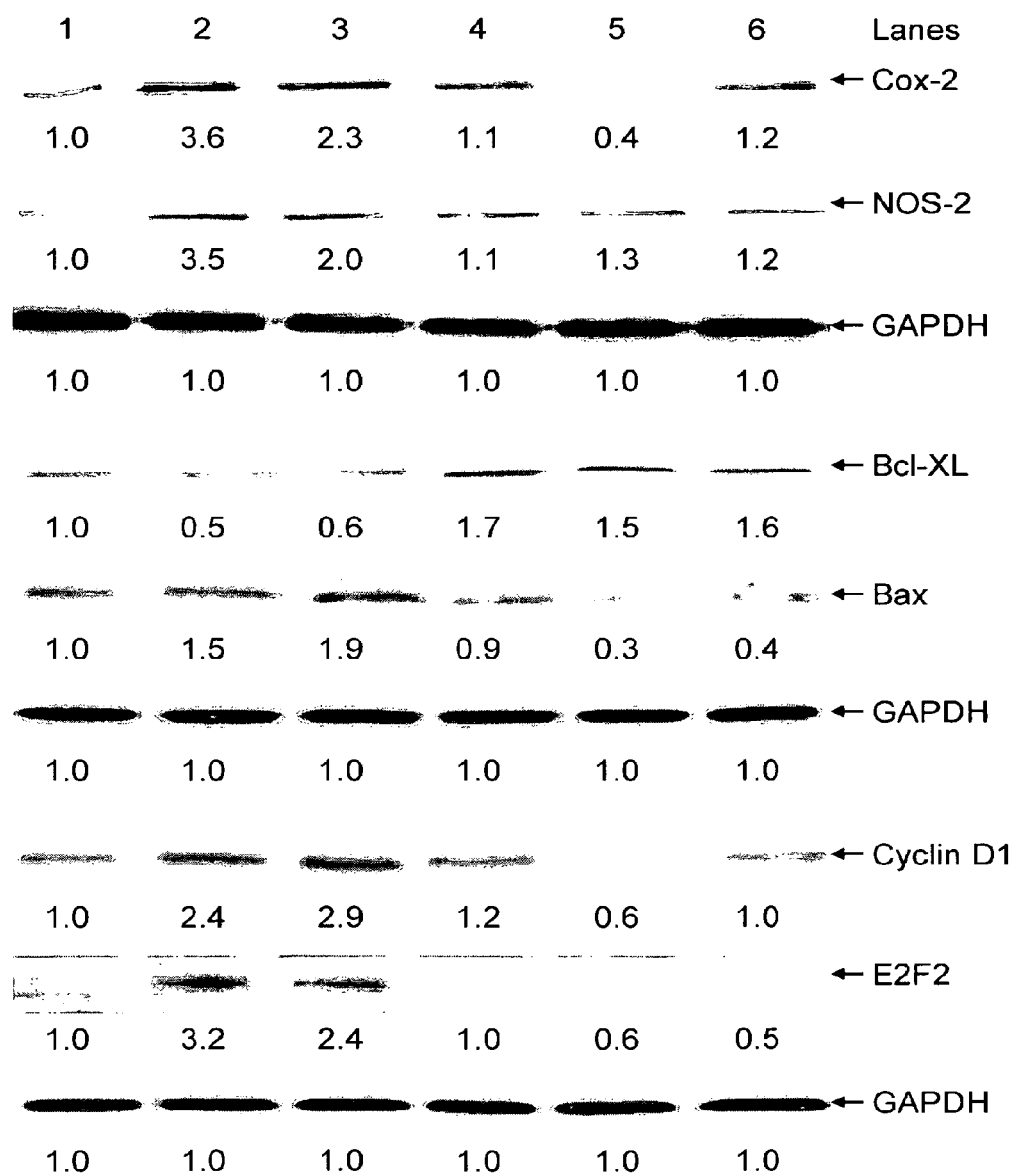

FIG. 26 AR inhibition prevents TNF-α- and LPS-induced expression of inflammatory, apoptosis and cell cycle proteins in SAEC. Approximately 2×10$^5$ SAEC were seeded in 6-well plates and incubated until 80% confluence. Medium was replaced with basal (serum-free) medium with AR inhibitor or carrier for 24 h. The cells were treated with TNF-α (2 nM) and LPS (1 μg/ml) for further 24 h. The cells were washed and cell lysate was prepared and Western blotting was performed to determine the expression of various proteins as described in the methods. GAPDH was used as loading control. Representative blots are shown (n=3) Lanes: 1, Control; 2, TNF-α; 3, LPS; 4, Sorbinil+Control; 5, Sorbinil+TNFα; 6, Sorbinil+LPS.

Figure 27A:
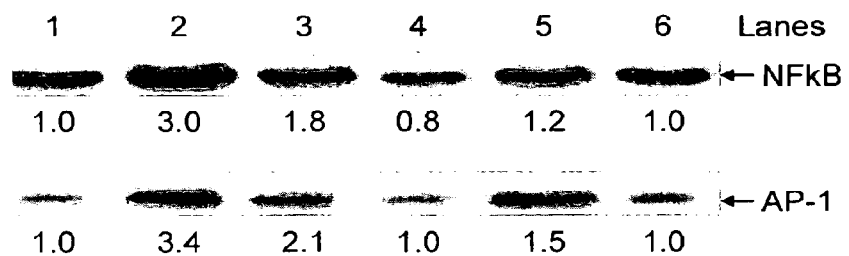
Figure 27B:
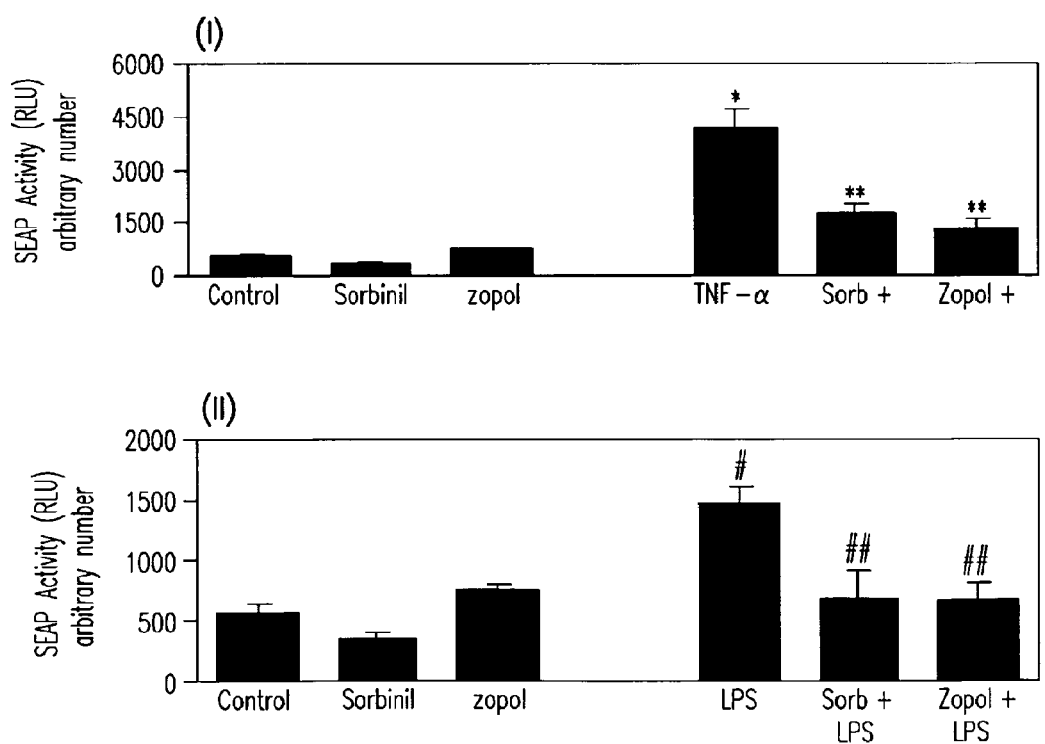

FIGS. 27A-27B AR inhibition attenuates TNF-α- and LPS-induced activation of redox-sensitive transcription factors NF-kB and AP-1 in SAEC. (FIG. 27A) Approximately 2×10$^6$ SAEC were seeded in T-150 cm$^2$ flasks and incubated till >90% confluence. Medium was replaced with basal (serum-free) medium with AR inhibitors or carrier for 24 h. The cells were treated with TNF-α (2 nM) for 1 h and LPS (1 μg/ml) for 3 h. Nuclear extracts were prepared as described in the methods and EMSA was performed to determine the activation and translocation of NF-κB and AP-1 to nucleus. Lanes: 1, Control; 2, Ragweed; 3, C+Zop; 4, RW+Zop. (FIG. 27B). For SAEP assay, SAEC were Growth-arrested by pre-incubating with basal medium with AR inhibitors sorbinil or zopolrestat or carrier for 24 hours followed by transfection with NF-κB-pSEAP vector or control (pTAL) vector and after 6 h stimulated with (FIG. 27B(I)) TNF-α (2 nM) and (FIG. 27B(II)) LPS (1 μg/ml) and incubated for 48 h. Media were collected and NF-κB-dependent SEAP activity was determined by chemiluminescence's method essentially as described by the manufacturer. Bars represent Mean±SD (n=6). *p<0.001 Vs. Control; **p<0.001 Vs. TNF-α; #p<0.01 Vs Control; ##p<0.01 Vs. LPS.

Figure 28A:
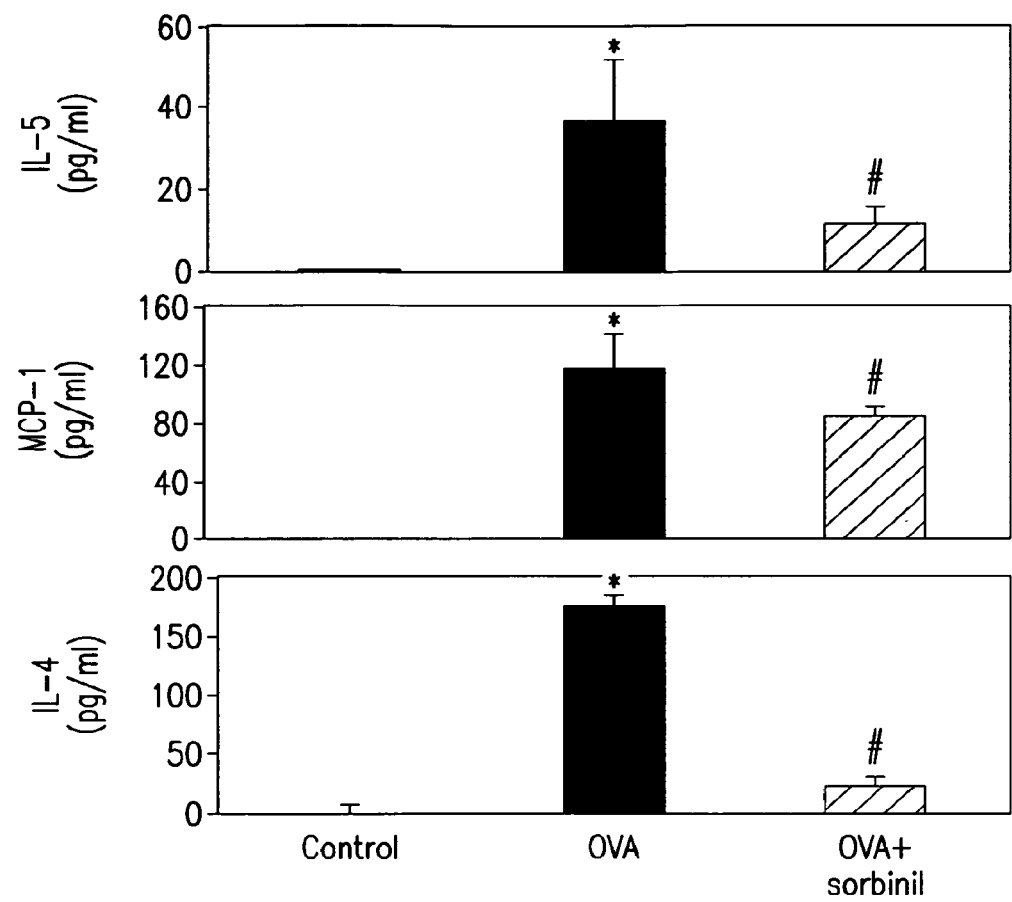
Figure 28B:
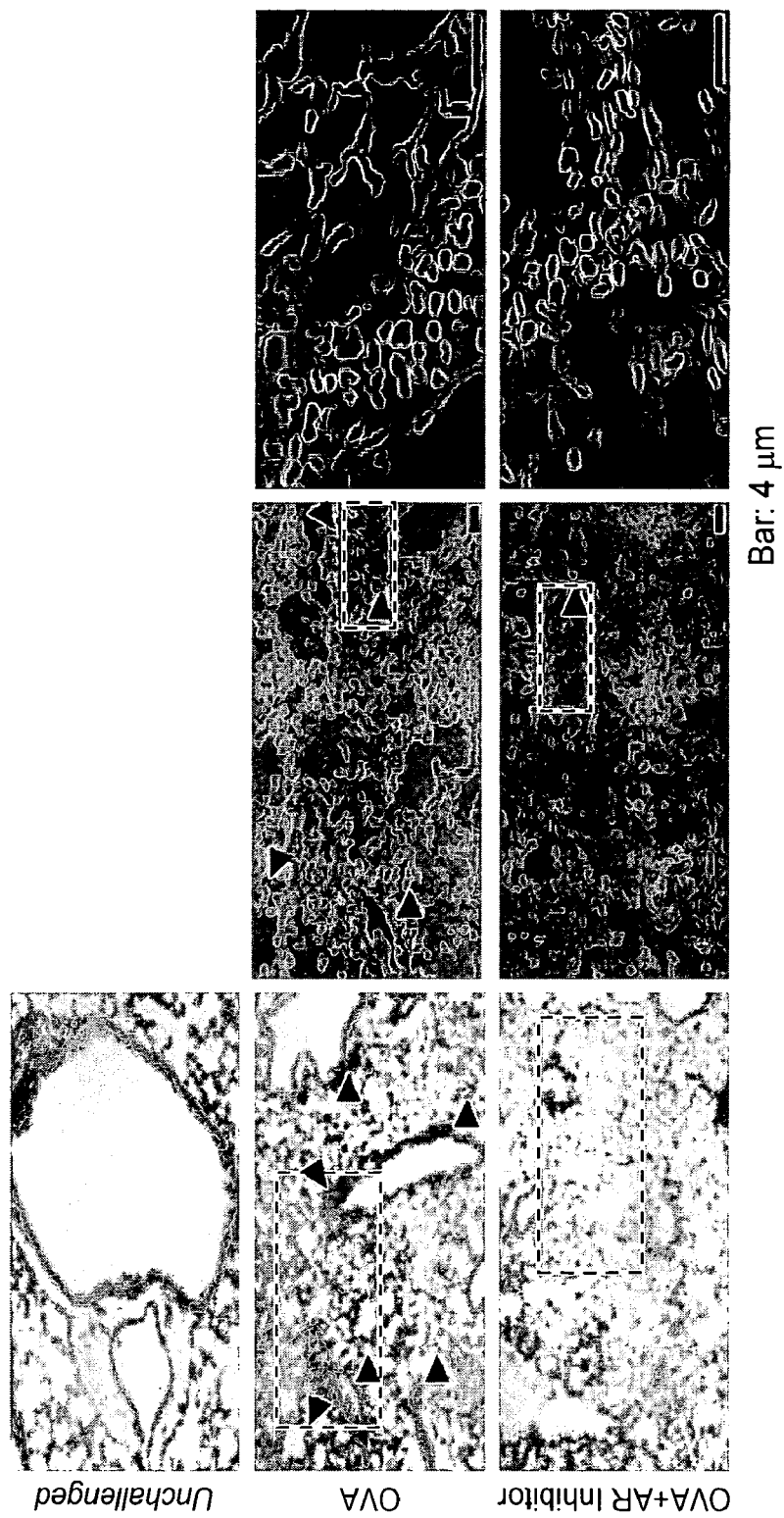

FIGS. 28A-28B Effect of AR inhibition on (FIG. 28A) Th2 cytokine production and (FIG. 28B) inflammatory cell (eosinophils) infiltration in lungs of ovalbumin (OVA)-induced murine model of asthma. (FIG. 28A) Cytokine levels in BAL fluids were measured using the Bio-Rad Bioplex system. Data are given as means±SD (n=4). *p<0.01 compared to unchallenged mice; #p<0.01 compared with OVA-challenged mice. (FIG. 28B) Fixed lungs from the different experimental groups were sectioned, stained with hematoxylin and eosin. Arrows indicate sites of inflammatory cells infiltration induced by OVA-challenge.

DETAILED DESCRIPTION OF THE INVENTION

The inventors have demonstrated that Aldose Reductase (AR) is important for the detoxification of lipid aldehydes. In addition to the detoxification role, AR activity is necessary for cell signaling of cytokines, chemokines, endotoxins, high glucose, and growth factors that cause cell apoptosis and proliferation which cause tissue dysfunction leading to inflammation and various diseases, i.e., AR is an obligatory mediator of cytokine, chemokine, growth factors, and bacterial endotoxin-induced by activation of transcription factors NF-κB and AP1 through a cascade of kinases. The activation of transcription factors is responsible for the synthesis and release of a number of cytokines, chemokines, and growth factors which cause cytotoxicity. They are responsible for causing inflammation in general (see U.S. patent application Ser. No. 11/210,283, filed Aug. 23, 2005; U.S. patent application Ser. No. 10/462,223, filed on Jun. 13, 2004; U.S. Provisional Application 60/603,725 filed on Aug. 23, 2004; U.S. Provisional Application 60/388,213, filed on Jun. 13, 2003, all of which are hereby incorporated by reference).

Since ocular inflammation is one of the major cause of uveitis, the effect of AR inhibition by Sorbinil or zopolrestat (an ARI) was systematically assessed using two different models of uveitis: (a) Endotoxin-induced uveitis (EIU) and (b) autoimmune-induced uveitis. The inventors demonstrate that aldose reductase inhibitors prevents, ameliorates, or attenuates uveitis and conjuctivitis. In addition AR inhibitors also prevent allergic conjuctivitis.

Furthermore, since inflammation is one of the major cause of asthma pathogenesis, the inventors systematically investigated the effect of AR inhibition by Sorbinil in two asthma models: (a) asthma induced by ragweed, and (b) asthma induced by ovalbumin. The inventors demonstrate aldose reductase inhibitors (ARI) significantly prevents eosinophil infiltration in the lungs and reduce levels of cytokines such as IL-4 (~90%). In the ragweed model mucosal secretion and airway obstruction was significantly prevented by ARI.

I. Aldose Reductase and Uveitis and Conjuctivitis

Uveitis is the major cause of severe visual impairment and has been estimated to account for 5-15% of all cases of total blindness in the U.S. (Read, 2006; Curi et al., 2005). It's even more prevalent in developing nations with limited access to health care (Rathinam and Cunningham, 2000). The uvea has good vasculature that nourishes the eye and inflammation in uvea can affect ocular functions. Although the cause of uveitis can include autoimmune disorders, infection, or exposure to toxins, in a number of cases the etiology remains unknown (Gupta and Murray, 2006). However, the ocular inflammation due to autoimmune diseases and infections is considered the major source (Nussenblatt, 1990). Steroids, and other drugs that suppress immune responses, are currently used to control the inflammation have many serious side effects including severely diminishing patient's quality of life (Dukes MNG. Corticotrophins and corticosteroids. In: Dukes MNG, ed, Meyler's Side Effects of Drugs, Amsterdam: Elsevier; 1996: 1189-1209; Samudre et al., 2004).

In uveitis, cytokine levels significantly increase in ocular tissues and initiate distinct intracellular signaling cascades that lead to both acute physiological effects and long-term changes in inflammatory gene expression (Read, 2006; Curi et al. 2005; Curnow and Murray, 2006). Therefore, elucidation of cytokine signaling is beneficial for understanding uveitis. Endotoxin-induced uveitis (EIU) is an acute anterior segment intraocular inflammation that can be induced by lipopolysaccharide (LPS) in rodents (Rosenbaum et al., 1980). Although EIU was originally used as a model of anterior uveitis, increasing evidences suggest that it also involves inflammation in the posterior segment of the eye with recruitment of leukocytes that adhere to the retinal vasculature and infiltrate the vitreous cavity (Read, 2006; Rosenbaum et al., 1980; Altan-Yaycioglu et al., 2006). This phenomenon serves as a model for certain types of human uveitis such as those associated with seronegative arthritis, where gram-negative bacteria may play a role in the pathogenesis (Rosenbaum et al., 1980). LPS enhances the expression of various inflammatory cytokines and chemokines such as TNF-α, IL-6, MIF, IFN-γ, MCP-1 as well as the production of $PGE_2$ and nitric oxide resulting in the breakdown of the blood-ocular barrier and in the infiltration of leukocytes and monocytes in ocular tissues which contribute to the development of EIU (Rosenbaum et al., 1980).

Various reports show that reactive oxygen species (ROS) are obligatory mediators of inflammation induced by cytokines and chemokines (Nagata, 2005; Chatterjee and Fisher, 2004) which in turn induce intracellular ROS generation by (a) mitochondrial respiratory chain reaction, (b) the arachidonic metabolic reactions of Cox-2, and (c) the membrane-bound superoxide-generating enzyme NADPH oxidase. Further, ROS activate redox-sensitive transcription factors such as NF-κB and AP-1 which play a central and crucial role in inflammation (Wang et al., 2002; Kitamei et al., 2006; Fang et al., 2005). This is probably due to the over-expression of inflammatory cytokines and iNOS and Cox-2 enzymes resulting in increased NO and $PGE_2$ (Lo and Cruz, 1995; Fraser, 2006). These local messenger molecules act further in autocrine and paracrinc fashion and elevate ROS effects. The ROS in turn activate various genes which are involved in the cytotoxicity. For example the pro-inflammatory cytokines TNF-α, IL-1, IL-6 play important role at initial stages of cell growth or apoptosis. Among the proinflammatory cytokines, TNF-α is known to be recognized as a central mediator in the pathophysiology of chronic inflammatory bowel diseases such as Crohn's and ulcerative colitis which cause increased risk of uveitis (Lin et al., 2006; Orchard et al., 2002). Recent studies have shown the use of anti-TNF-α therapy to treat uveitis (Dick et al., 2004; Hale and Lightman, 2006; El-Shabrawi and Hermann, 2002; Joseph et al., 2003). However, it is not clear how inflammation-associated increase in free radicals could cause activation of NF-κB.

The inventors' recent studies suggest that the polyol pathway enzyme-aldose reductase (AR; AKR1B1) reduces various lipid aldehydes and their glutathione conjugates in addition to aldo-sugars, and that AR is an obligatory mediator of ROS signals (Srivastava et al., 2005). Further, it has been shown that inhibition or ablation of AR prevents the cytokines-, growth factors- and hyperglycemia-induced cytotoxic signals in vascular smooth muscle cells (VSMC), vascular endothelial cells (VEC) and macrophages (Ramana et al., 2002; Ramana et al., 2005; Ramana et al., 2004; Ramana et al., 2006). The inventors have also demonstrated that TNF-α- and high glucose-induced activation of NF-κB and apoptosis of human lens epithelial cells (HLEC) were significantly prevented by AR inhibition (Ramana et al., 2003). Further, AR inhibition prevents LPS-induced expression of TNF-α, MMP2, MMP9 and Cox-2 in HLEC which indicates the role of AR in mediating inflammatory signals in lens epithelial cells (Pladzyk et al., 2006). However, the role of AR in mediating ocular inflammation leading to uveitis is not known. The inventors have investigated the effect of AR inhibition on the ocular inflammation caused by LPS during EIU in Lewis rats. The results show that inhibition of AR prevents EIU-induced activation of NF-κB and production of inflammatory markers such as NO, $PGE_2$, Cox-2, and TNF-α, and accumulation of infiltrating cells in various ocular tissues indicating therapeutic applications of AR inhibitors in ocular inflammation.

II. Aldose Reductase and Asthma

Asthma is one of the most common chronic respiratory diseases, with more than 100 million sufferers worldwide. This inflammatory disorder is caused by a hypersensitive immune system that results from a number of triggers, such as dust, pollen, viruses and changes in the weather. While it is not clear how asthma is initiated in the setting of chronic inflammation, accumulating evidences strongly support the association of airway inflammation to asthma (Rosi et al., 2006). Furthermore, the increase in inflammation in bronchial epithelium leads to eosinophils infiltration, an increase in mucus production, and most importantly upregulation of cytokines such as TNF-α, TL-4, TL-5, TL-6, TL-13, chemokines such as MCP-1, MIP-1, adhesion molecules such as ICAM-1, and E and P-Selectins (Nakajima and Takatsu, 2006; Riffo-Vasquez and Spina, 2002). Thus, exposure of nearby cells to inflammatory cytokines and chemokines can trigger various autocrine/paracrine effects leading to Th2 immune response and inflammatory cell accumulation. Hence elucidating the mechanisms that regulate inflammatory signals is profoundly important for understanding and managing a very large array of disease processes, including asthma. Since transcription factors such as NF-κB and AP1 are known to regulate the expression of multiple proinflammatory genes associated with the pathogenesis of asthma, drugs and antioxidants that inhibit NF-κB and AP1 activation are being used to treat asthma pathogenesis (Gagliardo et al., 2003; Frode-Saleh and Calixto, 2000; Chang and Crapo, 2002). However, it is not clear how an inflammation-associated increase in oxygen free radicals (Reactive Oxygen Species, ROS) could cause activation of NF-κB. Recent studies suggest that the polyol pathway enzyme-AR is a regulator of oxidative stress signals induced by cytokines, chemokines and growth factors (GF), leading to cytotoxicity, such as apoptosis of epithelial cells and vascular endothelial cells (VEC) (Srivastava et al., 2005; Ramana et al., 2003; Ramana et al., 2004). The inventors have identified the involvement of AR in the airway inflammatory signals induced by various oxidants, and AR in the pathways that contribute to asthma.

Significance of AR in inflammation: Recent reports suggest that growth factors and cytokines play an important role in modifying as well as accelerating inflammation (Nakajima and Takatsu, 2006; Riffo-Vasquez and Spina, 2002). Cytokines such as IL-5, IL-4 and TNF-α, and growth factors such as EGFR, FGF and VEGF, play key roles in inflammation by increasing ROS. The ROS generated during inflammation readily result in the formation of lipid derived aldehydes (LDAs), which are the major contributors to the pathophysiology of asthma and its complications (Corradi et al., 2004; Wood et al., 2003). The inventors have shown that LDAs, such as the most abundant and toxic, 4-hydroxynonenal (HNE), are readily reduced by AR in the presence of NADPH ($K_m$ 10-30 μM). Further, kinetic studies have demonstrated that AR catalyzes the reduction of glutathione (GSH)-aldehydes with 10 to 100-fold higher catalytic efficiency than their parent aldehydes, because the active site of AR shows high affinity for GSH-conjugates (Srivastava et al., 1995). Indeed, the inventors have demonstrated by computer modeling and site-directed mutagenesis that besides carbonyl binding, the AR active site also shows specific binding for GSH (Ramana et al., 2000; Dixit et al., 2000). The inventors have recently crystallized AR conjugated with a GS-analog and solved its crystal structure, which shows a specific binding site for GSH (Singh et al., 2006). This has opened up an entirely novel approach of synthesizing structure-based AR inhibitors, which could decrease or abolish GSH binding without affecting the binding and reduction of aldehydes. Such compounds should be able to attenuate signaling that causes cellular cytotoxicity including transcription of inflammatory markers, without affecting the detoxification of unconjugated LDAs generated by oxidants that could otherwise be toxic. The novel AR inhibitors could be excellent anti-inflammatory drugs with less or minimum side effects upon long term use in respiratory disorders such as asthma.

In one example, the inventors contemplate that AR regulates the cellular redox state via AR/NADPH-catalyzed reduction of lipid aldehydes and their conjugates with GSH which mediate ROS-induced NF-κB and AP1 activation. This is based upon earlier studies demonstrating that AR catalyzed GS-LDAs mediate cytotoxic signals (Srivastava et al., 2005). AR is a significant component of redox cell signaling and is induced by cytokines such as TNF-α which is known to induce the generation of ROS (Srivastava et al., 2005). Expression of AR is enhanced during inflammation and under high oxidative stress that results in increased HNE formation, suggesting redox regulation of the AR gene in several tissues (Srivastava et al., 2005). Given the extensive evidence implicating ROS as mediators of cell growth, differentiation, and inflammation, it is likely that oxidant-induced up-regulation of AR could be the mediator of signals that activate NF-κB and AP1 and cause inflammation.

The association of ROS and AR is supported by the observations that inhibitors of AR attenuate glucose-induced oxidative stress and superoxide production in retinal pericytes, lens epithelial cells and rabbit aorta (Miwa et al., 2003; Murata et al., 2001; Tesfamariam et al., 1993). The strongest evidence that AR is involved in mediating growth comes from studies showing that inhibition of AR prevents proliferation of cultured vascular smooth muscle cells (VSMCs) in response to TNF-α and high glucose (Ramana et al., 2002; Srivastava et al., 2006). The inventor's recent studies demonstrate that AR plays a pivotal role in the proliferation of VSMCs, apoptosis of vascular endothelial cells (VECs) and restenosis of rat carotid arteries. The inventors have also shown that AR inhibition significantly decreases neointima formation in balloon-injured rat carotid arteries, and also diminishes the in situ activation of NF-κB during restenosis (Ramana et al., 2004). Inhibition or ablation of AR attenuated TNF-α and GF-induced activation of PKC and NF-κB leading to proliferation of VSMCs, and apoptosis of VECs and macrophages (Ramana et al., 2002; Srivastava et al., 2006; Ramana et al., 2004; Ramana et al., 2006). Thus, modulation of NF-κB could explain the regulation of a large number of genes involved in inflammation mediated/induced by AR, including cytokines (TNF, IL-1, IL-8, IL-6), cell adhesion proteins such as ICAM-1 and VCAM and enzymes such as NOS, Cox and Mn-SOD. Furthermore, the inventors have shown that ROS-mediated inflammation, a major cause of colorectal cancer and bacterial endotoxin-induced sepsis that causes cardiomyopathy, can be significantly prevented by AR inhibition or ablation.

Elucidation of the role of ROS-induced lipid aldehydes in inflammation is a daunting task as it involves tight regulation and interaction of many cell types and signaling cascades and overwhelming inflammation. The inventors contemplate that AR-catalyzed reaction products should play an important role in eliciting LPS-induced cytotoxicity and inflammation (Ramana et al., 2006a; Ramana et al., 2006b; Ramana et al., 2006c). Based on recent observations, ongoing studies will further elucidate: (1) the role of lipid peroxidation, lipid aldehydes formation, and their conjugation with GSH and reduction of the conjugates by AR in the initiation of inflammatory signals; and (2) how AR could mediate inflammatory signaling that promote asthma. Although the precise mechanism(s)

of cytotoxicity is not known, based upon results using macrophages, the inventors contemplate that AR-dependent PKC activation is a key event in the process that activates downstream signals leading to activation of NF-κB. Preliminary results show that asthma induced by RW or OVA in mice can be prevented by AR inhibition. Further studies, investigate the mechanism and vigorously test the feasibility of the use of AR inhibitors in the prevention of asthma.

III. Aldose Reductase Inhibitors

The inhibitors of aldose reductase can be any compound that inhibits the enzyme aldose reductase. The aldose reductase inhibitor compounds of this invention are readily available or can be easily synthesized by those skilled in the art using conventional methods of organic synthesis, particularly in view of the pertinent patent specifications.

Many of these are well known to those of skill in the art, and a number of pharmaceutical grade AR inhibitors are commercially available, such as Tolrestat, N—[[6-methoxy-5-(trifluoromethyl)-1-naphthalenyl]thioxomethyl]-N-methylglycine, [Wyeth-Ayerst, Princeton, N.J.; other designations are Tolrestatin, CAS Registry Number 82964-04-3, Drug Code AY-27,773, and brand names ALREDASE (Am. Home) and LORESTAT (Recordati)]; Ponalrestat, 3-(4-bromo-2-fluorobenzyl)-4-oxo-3H-phthalazin-1-ylacetic acid [ICI, Macclesfield, U.K.; other designations are CAS Registry Number 72702-95-5, ICI-128,436, and STATIL (ICI)]; Sorbinil, (S)-6-fluoro-2,3-dihydrospiro[4H-1-benzopyran-4,4'-imidazolidine]-2',5'-di one (Pfizer, Groton, Conn.; CAS Registry Number 68367-52-2, Drug Code CP-45,634); EPALRESTAT (ONO, Japan); METHOSORBINIL (Eisal); ALCONIL (Alcon); AL-1576 (Alcon); CT-112 (Takeda); and AND-138 (Kyorin).

Other ARIs have been described. For a review of ARIs used in the diabetes context, see Humber, Leslie "Aldose Reductase Inhibition: An Approach to the Prevention of Diabetes Complications", Porte, ed., Ch. 5, pp. 325-353; Tomlinson et al., 1992), such as spirohydantoins and related structures, spiro-imidazolidine-2',5'-diones; and heterocycloic alkanoic acids. Other aldose reductase inhibitors are ONO-2235; zopolrestat; SNK-860; 5-3-thienyltetrazol-1-yl (TAT); WAY-121,509; ZENECA ZD5522; M16209; (5-(3'-indolal)-2-thiohydantoin; zenarestat; zenarestat 1-O-acylglucuronide; SPR-210; (2S,4S)-6-fluoro-2',5'-dioxospiro-[chroman-4,4'-imidazolidine]-2-carboxamide (SNK-880); arylsulfonylamino acids; 2,7-difluorospirofluorene-9,5'-imidazolidine-2',4'-dione (imiriestat, Al11576, HOE 843); and isoliquiritigenin.

In some embodiments, the aldose reductase inhibitor is an compound that directly inhibits the bioconversion of glucose to sorbitol catalyzed by the enzyme aldose reductase. Such aldose reductase inhibitors are direct inhibitors, which are contemplated as part of the invention. Direct inhibition is readily determined by those skilled in the art according to standard assays (Malone, 1980). The following patents and patent applications, each of which is hereby wholly incorporated herein by reference, exemplify aldose reductase inhibitors which can be used in the compositions, methods and kits of this invention, and refer to methods of preparing those aldose reductase inhibitors: U.S. Pat. Nos. 4,251,528; 4,600,724; 4,464,382, 4,791,126, 4,831,045; 4,734,419; 4,883,800; 4,883,410; 4,883,410; 4,771,050; 5,252,572; 5,270,342; 5,430,060; 4,130,714; 4,540,704; 4,438,272; 4,436,745, 4,438,272; 4,436,745, 4,438,272; 4,436,745, 4,438,272; 4,980,357; 5,066,659; 5,447,946; and 5,037,831.

A variety of aldose reductase inhibitors are specifically described and referenced below, however, other aldose reductase inhibitors will be known to those skilled in the art. Also, common chemical names or other designations are in parentheses where applicable, together with reference to appropriate patent literature disclosing the compound. Accordingly, examples of aldose reductase inhibitors useful in the compositions, methods and kits of this invention include, but are not limited to: 3-(4-bromo-2-fluorobenzyl)-3,4-dihydro-4-oxo-1-phthalazineacetic acid (ponalrestat, U.S. Pat. No. 4,251,528); N[[(5-trifluoromethyl)-6-methoxy-1-naphthalenyl]thioxomethyl}-N-methylglycine (tolrestat, U.S. Pat. No. 4,600,724); 5-[(Z,E)-β-methylcinnamylidene]-4-oxo-2-thioxo-3-thiazolideneacetic acid (epalrestat, U.S. Pat. No. 4,464,382, U.S. Pat. No. 4,791,126, U.S. Pat. No. 4,831,045); 3-(4-bromo-2-fluorobenzyl)-7-chloro-3,4-dihydro-2,4-dioxo-1(2H)-quinazolineacetic acid (zenarestat, U.S. Pat. No. 4,734,419, and U.S. Pat. No. 4,883,800); 2R,4R-6,7-dichloro-4-hydroxy-2-methylchroman-4-acetic acid (U.S. Pat. No. 4,883,410); 2R,4R-6,7-dichloro-6-fluoro-4-hydroxy-2-methylchroman-4-acetic acid (U.S. Pat. No. 4,883,410); 3,4-dihydro-2,8-diisopropyl-3-oxo-2H-1,4-benzoxazine-4-acetic acid (U.S. Pat. No. 4,771,050); 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252,572); N-[3,5-dimethyl-4-[(nitromethyl)sulfonyl]phenyl]-2-methyl-benzeneacetamide (ZD5522, U.S. Pat. No. 5,270,342 and U.S. Pat. No. 5,430,060); (S)-6-fluorospiro[chroman-4,4'-imidazolidine]-2,5'-dione (sorbinil, U.S. Pat. No. 4,130,714); d-2-methyl-6-fluoro-spiro(chroman-4',4'-imidazolidine)-2',5'-dione (U.S. Pat. No. 4,540,704); 2-fluoro-spiro (9H-fluorene-9,4'-imidazolidine)-2',5'-dione (U.S. Pat. No. 4,438,272); 2,7-di-fluoro-spiro(9H-fluorene-9,4'-imidazolidine)-2',5'-dione (U.S. Pat. No. 4,436,745, U.S. Pat. No. 4,438,272); 2,7-di-fluoro-5-methoxy-spiro(9H-fluorene-9,4'-imidazolidine)-2',5'-dione (U.S. Pat. No. 4,436,745, U.S. Pat. No. 4,438,272); 7-fluoro-spiro(5H-indenol[1,2-b]pyridine-5,3'-pyrrolidine)-2,5'-dione (U.S. Pat. No. 4,436,745, U.S. Pat. No. 4,438,272); d-cis-6'-chloro-2',3'-dihydro-2'-methyl-spiro-(imidazolidine-4,4'-4'H-pyrano(2,3-b)pyridine)-2,5-dione (U.S. Pat. No. 4,980,357); spiro[imidazolidine-4,5'(6H)-quinoline]-2,5-dione-3'-chloro-7',8'-dihydro-7'-methyl-(5'-cis) (U.S. Pat. No. 5,066,659); (2S,4S)-6-fluoro-2',5'-dioxospiro(chroman-4,4'-imidazolidine)-2-carboxamide (fidarestat, U.S. Pat. No. 5,447,946) and 2-[(4-bromo-2-fluorophenyl)methyl]-6-fluorospiro[isoquinoline-4(1H), 3'-pyrrolidine]-1,2',3,5'(2H)-tetrone (minalrestat, U.S. Pat. No. 5,037,831). Other compounds include those described in U.S. Pat. Nos. 6,720,348, 6,380,200, and 5,990,111, which are hereby incorporated by reference. Moreover, in other embodiments it is specifically contemplated that any of these may be excluded as part of the invention.

Embodiments of the invention contemplate inhibitors of aldose reductase that are peptides or proteins that form a proteinaceous composition. It is contemplated that any teaching with respect to one particular proteinaceous composition may apply generally to other proteinaceous compositions described herein.

As used herein, a "proteinaceous molecule," "proteinaceous composition," "proteinaceous compound," or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

In certain embodiments of the invention, the proteinaceous composition may include such molecules that may comprise, but is not limited to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 383, 385 or greater amino molecule residues, and any range derivable therein. Such lengths are applicable to all polypeptides and peptides mentioned herein. It is contemplated that an aldose reductase inhibitor may specifically bind or recognize a particular region of AR, including 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 383, 385 or greater contiguous amino acids of aldose reductase or any range of numbers of contiguous amino acids derivable therein. Aldose reductase may be from any organism, including mammals, such as a human, monkey, mouse, rat, hamster, cow, pig, rabbit, and may be from other cultured cells readily available. AR inhibitors may also affect polypeptides in pathways involving AR but found further upstream or downstream from AR in the pathway.

It will also be understood that amino acid sequences or nucleic acid sequences of AR, AR polypeptide inhibitors, or screening proteins may include additional residues, such as additional N- or C-terminal amino acids or 5' or 3' sequences, or various combinations thereof, and yet still be essentially as set forth in one of the sequences disclosed herein, so long as the sequence meets the criteria set forth above, including the maintenance of biological protein, polypeptide or peptide activity where expression of a proteinaceous composition is concerned. The addition of terminal sequences particularly applies to nucleic acid sequences that may, for example, include various non-coding sequences flanking either of the 5' and/or 3' portions of the coding region or may include various internal sequences, i.e., introns, which are known to occur within genes.

Another embodiment for the preparation of polypeptides according to the invention is the use of peptide mimetics. Peptide mimetics may be screened as a candidate substance. Mimetics are peptide-containing compounds, that mimic elements of protein secondary structure. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outlined above, to engineer second generation molecules having many of the natural properties of AR inhibitors, but with altered and even improved characteristics.

The present invention also contemplates the synthesis of peptides that can directly or indirectly inhibit AR. Because of their relatively small size, the peptides of the invention can also be synthesized in solution or on a solid support in accordance with conventional techniques. Various automatic synthesizers are commercially available and can be used in accordance with known protocols. See, for example, Tam et al., (1983); Merrifield, (1986); and Barany and Merrifield (1979). Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

In one embodiment, nucleic acid sequences complementary to at least a portion of the nucleic acid encoding AR will find utility as AR inhibitors. The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. In certain embodiments, these probes consist of oligonucleotide fragments. Such fragments should be of sufficient length to provide specific hybridization to a RNA or DNA tissue sample. The sequences typically will be 10-20 nucleotides, but may be longer. Longer sequences, e.g., 40, 50, 100, 500 and even up to full length, are preferred for certain embodiments.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs may include regions complementary to intron/exon splice junctions. Thus, antisense constructs with complementarity to regions within 50-200 bases of an intron-exon splice junction may be used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme) could be designed. These molecules, though having less than 50% homology, would bind to target sequences under appropriate conditions.

The use of AR-specific ribozymes is claimed in the present application. The following information is provided in order to compliment the earlier section and to assist those of skill in the art in this endeavor. Ribozymes are RNA-protein complexes that cleave nucleic acids in a site-specific fashion. Ribozymes have specific catalytic domains that possess endonuclease activity (Kim and Cech, 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990; Sioud et al., 1992). In light of the information included herein and the knowledge of one of ordinary skill in the art, the preparation and use of additional ribozymes that are specifically targeted to a given gene, e.g., AR gene, will now be straightforward.

Several different ribozyme motifs have been described with RNA cleavage activity (reviewed in Symons, 1992). Examples that would be expected to function equivalently for the down regulation of AR include sequences from the Group I self splicing introns including tobacco ringspot virus (Prody et al., 1986), avocado sunblotch viroid (Symons, 1981), and Lucerne transient streak virus (Forster and Symons, 1987). Sequences from these and related viruses are referred to as hammerhead ribozymes based on a predicted folded secondary structure. Other suitable ribozymes include sequences from RNase P with RNA cleavage activity (Yuan et al., 1992, Yuan and Altman, 1994), hairpin ribozyme structures (Berzal-Herranz et al., 1992; Chowrira et al., 1993) and hepatitis 6 virus based ribozymes (Perrotta and Been, 1992). The general design and optimization of ribozyme directed RNA cleavage activity has been discussed in detail (Haseloff and Gerlach, 1988, Symons, 1992, Chowrira, et al., 1994; Thompson, et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozymes, the cleavage site is a dinucleotide sequence on the target RNA, uracil (U) followed by either an adenine, cytosine or uracil (A,C or U; Perriman, et al., 1992; Thompson, et al., 1995). The frequency of this dinucleotide occurring in any given RNA is statistically 3 out of 16. Therefore, for a given target messenger RNA of 1000 bases, 187 dinucleotide cleavage sites are statistically possible.

Designing and testing ribozymes for efficient cleavage of a target RNA is a process well known to those skilled in the art. Examples of scientific methods for designing and testing ribozymes are described by Chowrira et al., (1994) and Lieber and Strauss (1995), each incorporated by reference. The identification of operative and preferred sequences for use in AR-targeted ribozymes is simply a matter of preparing and testing a given sequence, and is a routinely practiced "screening" method known to those of skill in the art.

An RNA molecule capable of mediating RNA interference in a cell is referred to as "siRNA." Elbashir et al. (2001) discovered a clever method to bypass the anti viral response and induce gene specific silencing in mammalian cells. Several 21-nucleotide dsRNAs with 2 nucleotide 3' overhangs were transfected into mammalian cells without inducing the antiviral response. The small dsRNA molecules (also referred to as "siRNA") were capable of inducing the specific suppression of target genes.

In the context of the present invention, siRNA directed against AR, NF-κB, and TNF-α are specifically contemplated. The siRNA can target a particular sequence because of a region of complementarity between the siRNA and the RNA transcript encoding the polypeptide whose expression will be decreased, inhibited, or eliminated.

An siRNA may be a double-stranded compound comprising two separate, but complementary strands of RNA or it may be a single RNA strand that has a region that self-hybridizes such that there is a double-stranded intramolecular region of 7 basepairs or longer (see Sui et al., 2002 and Brummelkamp et al., 2002 in which a single strand with a hairpin loop is used as a dsRNA for RNAi). In some cases, a double-stranded RNA molecule may be processed in the cell into different and separate siRNA molecules.

In some embodiments, the strand or strands of dsRNA are 100 bases (or basepairs) or less, in which case they may also be referred to as "siRNA." In specific embodiments the strand or strands of the dsRNA are less than 70 bases in length. With respect to those embodiments, the dsRNA strand or strands may be from 5-70, 10-65, 20-60, 30-55, 40-50 bases or basepairs in length. A dsRNA that has a complementarity region equal to or less than 30 basepairs (such as a single stranded hairpin RNA in which the stem or complementary portion is less than or equal to 30 basepairs) or one in which the strands are 30 bases or fewer in length is specifically contemplated, as such molecules evade a mammalian's cell antiviral response. Thus, a hairpin dsRNA (one strand) may be 70 or fewer bases in length with a complementary region of 30 basepairs or fewer.

Methods of using siRNA to achieve gene silencing are discussed in WO 03/012052, which is specifically incorporated by reference herein. Designing and testing siRNA for efficient inhibition of expression of a target polypeptide is a process well known to those skilled in the art. Their use has become well known to those of skill in the art. The techniques described in U.S. Patent Publication No. 20030059944 and 20030105051 are incorporated herein by reference. Furthermore, a number of kits are commercially available for generating siRNA molecules to a particular target, which in this case includes AR, NF-κB, and TNF-α. Kits such as Silencer™ Express, Silencer™ siRNA Cocktail, Silencer™ siRNA Construction, MEGAScript® RNAi are readily available from Ambion, Inc.

Other candidate AR inhibitors include aptamers and aptazymes, which are synthetic nucleic acid ligands. The methods of the present invention may involve nucleic acids that modulate AR, NF-κB, and TNF-α. Thus, in certain embodiments, a nucleic acid, may comprise or encode an aptamer. An "aptamer" as used herein refers to a nucleic acid that binds a target molecule through interactions or conformations other than those of nucleic acid annealing/hybridization described herein. Methods for making and modifying aptamers, and assaying the binding of an aptamer to a target molecule may be assayed or screened for by any mechanism known to those of skill in the art (see for example, U.S. Pat. Nos. 5,840,867, 5,792,613, 5,780,610, 5,756,291 and 5,582, 981, Burgstaller et al., 2002, which are incorporated herein by reference.

IV. Pharmaceutical Compositions and Routes of Administration

Pharmaceutical compositions of the present invention may comprise an effective amount of one or more AR inhibitors dissolved or dispersed in a pharmaceutically acceptable carrier to a subject. The phrases "pharmaceutical" or "pharmacologically acceptable" refers to molecular entities and compositions that do not produce an adverse, allergic or other untoward reaction when administered to an animal, such as, for example, a human, as appropriate. The preparation of a pharmaceutical composition that contains at least one AR inhibitor or additional active ingredient will be known to those of skill in the art in light of the present disclosure, and as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof; as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated. An AR inhibitor can be administered in the form of a pharmaceutically acceptable salt or with a pharmaceutically acceptable salt.

The expression "pharmaceutically acceptable salts" includes both pharmaceutically acceptable acid addition salts and pharmaceutically acceptable cationic salts, where appropriate. The expression "pharmaceutically-acceptable cationic salts" is intended to define, but is not limited to such salts as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) and procaine. The expression "pharmaceutically-acceptable acid addition salts" is intended to define but is not limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

Pharmaceutically acceptable salts of the aldose reductase inhibitors of this invention may be readily prepared by reacting the free acid form of the aldose reductase inhibitor with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), and employing a solvent (e.g., ethyl acetate) from which the desired cationic salt precipitates, or can be otherwise isolated by concentration and/or addition of a non-solvent.

The acid addition salts of the aldose reductase inhibitors of this invention may be readily prepared by reacting the free base form of said aldose reductase inhibitor with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate, or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

In addition, the aldose reductase inhibitors that may be used in accordance with this invention, prodrugs thereof, and pharmaceutically acceptable salts thereof or of said prodrugs, may occur as hydrates or solvates. These hydrates and solvates are also within the scope of the invention.

A pharmaceutical composition of the present invention may comprise different types of carriers depending on whether it is to be administered in solid, liquid or aerosol form, and whether it needs to be sterile for such routes of administration as injection. A pharmaceutical composition of the present invention can be administered intravenously, intradermally, intraarterially, intraperitoneally, intraarticularly, intrapleurally, intrabronchially, intrapleurally, intranasally, topically, intramuscularly, intraperitoneally, subcutaneously, subconjunctival, intravesicularlly, mucosally, intrapericardially, intraumbilically, orally, topically, locally, inhalation (e.g., aerosol inhalation), instillation, injection, infusion, continuous infusion, via a catheter, via a lavage, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. The number of doses and the period of time over which the dose may be given may vary. The practitioner responsible for administration will, in any event, determine the concentration of active ingredient(s) in a composition and appropriate dose(s), as well as the length of time for administration for the individual subject. An amount of an aldose reductase inhibitor that is effective for inhibiting aldose reductase activity is used. Typically, an effective dosage for the inhibitors is in the range of about 0.01 mg/kg/day to 100 mg/kg/day in single or divided doses, preferably 0.1 mg/kg/day to 20 mg/kg/day in single or divided doses. Doses of about, at least about, or at most about 0.01, 0.05, 0.1, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg/day, or any range derivable therein. Typically the dose will be 25 to 1200 mg per day and in certain aspects is between 100 and 800 mg per day.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

An AR inhibitor(s) of the present invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In certain aspects of the invention, the AR inhibitors are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

In order to increase the effectiveness of treatments with the compositions of the present invention, such as an AR inhibitor, it may be desirable to combine it with other therapeutic agents. This process may involve contacting the cell(s) with an AR inhibitor and a therapeutic agent at the same time or within a period of time wherein separate administration of the modulator and an agent to a cell, tissue or organism produces a desired therapeutic benefit. The terms "contacted" and "exposed," when applied to a cell, tissue or organism, are used herein to describe the process by which a AR inhibitor and/or therapeutic agent are delivered to a target cell, tissue or organism or are placed in direct juxtaposition with the target cell, tissue or organism. The cell, tissue or organism may be contacted (e.g., by administration) with a single composition or pharmacological formulation that includes both a AR inhibitor and one or more agents, or by contacting the cell with two or more distinct compositions or formulations, wherein one composition includes an AR inhibitor and the other includes one or more agents.

The AR inhibitor may precede, be concurrent with and/or follow the other agent(s) by intervals ranging from minutes to weeks. In embodiments where the AR inhibitor and other agent(s) are applied separately to a cell, tissue or organism, one would generally ensure that a significant period of time did not expire between the time of each delivery, such that the inhibitor and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the modulator. In other aspects, one or more agents may be administered within of from substantially simultaneously, about 1 minute, about 5 minutes, about 10 minutes, about 20 minutes about 30 minutes, about 45 minutes, about 60 minutes, about 2 hours, or more hours, or about 1 day or more days, or about 4 weeks or more weeks, or about 3 months or more months, or about one or more years, and any range derivable therein, prior to and/or after administering the AR inhibitor.

Various combinations of a AR inhibitor(s) and a second therapeutic may be employed in the present invention, where a AR inhibitor is "A" and the secondary agent, such as a antibiotic or other anti-inflammatory treatment, is "B":

A/B/A B/A/B B/B/A A/A/B A/B/B B/A/A B/B/B/A B/B/ A/B A/A/B/B A/B/A/B A/B/B/A B/B/A/A B/A/B/A B/A/A/B A/A/A/B B/A/A/A A/B/A/A A/A/B/A A/B/ B/B B/A/B/B

Administration of modulators to a cell, tissue or organism may follow general protocols for the administration of agents for the treatment of uveitis, conjunctivitis, or asthma. It is expected that the treatment cycles would be repeated as necessary. In particular embodiments, it is contemplated that various additional agents may be applied in any combination with the present invention. Agents include antibiotics (for gram-positive and gram negative bacteria), anti-inflammatory drugs, and immunosuppressant drugs, which are well known to those of skill in the art and frequently commerically available.

In such combinations, AR inhibitors and other active agents may be administered together or separately. In addition, the administration of one agent may be prior to, concurrent to, or subsequent to the administration of other agent(s).

V. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Aldose Reductase Inhibition Prevents Endotoxin-induced Uveitis

I. Materials and Methods:

Materials: RPMI-1640 medium, phosphate-buffered saline (PBS), gentamicin sulfate solution, trypsin/EDTA solution and fetal bovine serum (FBS) were purchased from GIBCO BRL Life Technologies (Grand Island, N.Y.). Sorbinil and zopolrestat were obtained as gift from Pfizer (New York, N.Y.). Dimethyl sulfoxide (DMSO) was obtained from Fischer scientific (Pittsburgh, Pa.). Nitrite/Nitrate and $PGE_2$ assay kits were obtained from Cayman Chemical Inc (Ann Arbor, Mich.). Rat TNF-α ELISA kit was obtained from BD Biosciences (San Diego, Calif.). LPS from *Escherichia coli* was obtained from Sigma (Sigma-Aldrich, Saint Louise, Mo.). Antibodies against TNF-α, and phospho-p65 (serine 536) were purchased from cell signaling (Danvers, Mass.), iNOS was from Cayman Chemicals (Ann Arbor, Mich.), Cox-2 and GAPDH were from Santacruz biotech inc. (Santa Cruz, Calif.), and polyclonal antibodies against human recombinant AR were made for the inventors by Alpha Diagnostic Intl. San Antonio, Tex. All other reagents used were of analytical grade.

Animal groups and EIU: Six to eight-weeks-old male Lewis rats weighing approximately 150-160 g were used in this study (n=6). All animals were kept in the UTMB's Animal Care Center. All the animal studies were conducted in compliance with the ARVO statement for the use of Animals in Ophthalmic and Vision Research. EIU was induced by a subcutaneous injection of *Escherichia coli* LPS (200 μg) dissolved in phosphate-buffered saline (PBS, pH 7.4). Rats in ART and ETU+ART groups were injected intraperitoneally with AR inhibitor zopolrestat (25 mg/kg body weight) dissolved in dimethyl-sulfoxide (DMSO) 24 h before and immediately after LPS injection. Rats of control group received carrier (PBS+20% DMSO) injection.

Infiltrating cells and proteins in aqueous humor: The rats were euthanized after 3, 6, and 24 h after LPS injection and the aqueous humor (AqH) was collected immediately from eye by an anterior chamber puncture using a 30-gauge needle under the surgical microscope. For cell counting, the AqH samples were suspended in an equal amount of Trypan-blue solution, and the cells were counted using a Hemocytometer under a light microscope (Olympus Optical Ltd). The total protein concentration in the AqH samples was measured using a Biorad protein assay kit (Biorad, CA, USA). The AqH samples were stored in ice water until testing, cell counts and total protein concentrations were measured on the day of sample collection. Rest of the AqH was stored at −80° C. until used.

TNF-α, NO and $PGE_2$ in aqueous humor: The levels of TNF-α in the AqH (stored at −80° C.) were assessed with commercially available ELISA kit, according to the manufacturer's instructions. The total level of nitrate plus nitrite in the AqH was measured by using a total nitrite colorimetric assay (LDH) kit according to the manufacturer's instructions. $PGE_2$ production was measured by enzyme immunoassay kit following the manufacturer's instructions.

Histopathological evaluation: Rats were euthanized 24 h after LPS injection and the eyes were enucleated immediately and stored in 4% para-formaldehyde solution for 48 h at 4° C. The eyes were washed in ice-cold PBS twice and kept in 70% alcohol at 4° C. until they were embedded in paraffin. Sagittal sections (5 μm) were cut and stained with hematoxylin and eosin (H&E). The iris-ciliary body complex, anterior chamber, vitreous and retina were observed under light microscope.

Immunohistochemical studies: The paraffin sections were warmed at 60° C. for 1 h and deparafinized in xylene, followed by rehydration by passing through 100%, 95%, 80% and 70% ethanol and finally washed in deionozed water. After peroxidase blocking with 3% $H_2O_2$ the sections were rinsed in PBS twice and incubated with blocking buffer (2% BSA, 0.1% Triton-X100, 2% normal rabbit IgG and 2% normal goat serum) for overnight at 4° C. Sections were incubated with antibodies against TNF-α, iNOS, Cox-2, phospho-p65 antibodies (Ser536), and AR for 1 hour at room temperature. The sections were stained using universal LSAB+System-HRP (DakoCytomation, CF, USA). The sections were examined under bright field light microscopy (EPI-800 microscope) and photographed with Nikon camera fitted to EPI-800 microscope.

Measurement of ROS: The levels of ROS in rat eye were quantified by dihydroethidium (DHE) (Molecular Probes, Eugene, Oreg., U.S.A.) which gives red fluorescence when oxidized to ethidium in the presence of ROS. Serial sections (5 μM) of para-formaldehyde fixed rat eyes were deparafenized, rehydrated and incubated with ROS-sensitive dye (5 μM) for 30 min at 37° C. followed by acquisition of images using a fluorescence microscope.

Cell Culture and LPS treatment: U-937, a human monocytic cell line, was obtained from ATCC (Manassas, Va., USA). The cells were cultured in RPMI-1640 medium supplemented with 2 mM glutamine, 1 mM sodium pyruvate, 25 mM HEPES, antibiotics (100 U/mL penicillin and 100 μg/mL streptomycin) and 10% heat-inactivated fetal bovine serum and maintained at 37° C. in a humidified incubator containing 95% $O_2$ and 5% $CO_2$. The cells were pretreated with 10 μM AR inhibitor, zopolrestat for overnight in serum-free medium and subsequently stimulated with 1 LPS from *E. coli* for 24 h, unless otherwise stated.

Western Blot Analysis: U-937 cells were washed twice with ice-cold PBS and lysed in ice-cold lysis buffer containing 50 mM HEPES [pH 7.6], 10 mM KCl, 0.5% NP-40, 1 mM DTT, 1 mM phenylmethylsulfonylfluoride (PMSF), and 1:100 dilution of protease inhibitor cocktail (Sigma, Saint Louise, Mo.) for 15 min with occasional vortexing at maximum speed at 4° C. The crude lysates were cleared by centrifugation at 12,000 g for 10 min at 4° C. Aliquots of the lysates were diluted with 2×SDS sample buffer and boiled for 5 minutes. Lysates were separated on 10% SDS-polyacrylamide gels and transferred to polyvinylidene difluoride membranes (Immobilon; Millipore, Bedford, Mass.). The membranes were then incubated in blocking solution containing 5% wt/vol dried fat-free milk and 0.1% vol/vol Tween-20 in Tris-buffered Saline. Subsequently, the membranes were incubated with anti-Cox-2, -iNOS, and -GAPDH antibodies. The membranes were then probed with horseradish peroxidase-conjugated secondary antibody (GE Healthcare, Piscataway, N.J.) and visualized by chemiluminescence (Pierce biotechnology, Rockford, Ill.).

Transient transfection and INF-κB-Dependent Secretory Alkaline Phosphatase (SEAP) Expression Assay: To examine NF-κB promoter activity in U-937 cells in response to LPS treatment, U-937 cells ($2.5 \times 10^6$ cells/well in 6-well plate) in RPMI-1640 (with 10% FBS) were transfected with pNF-κB-SEAP2-construct and pTAL-SEAP control plasmid (Clontech, USA) using Lipofectamine™ 2000 (Invitrogen, Carlsbad, Calif.) following suppliers instructions. The cells were harvested and plated in 24-well plate in serum-free medium, treated with AR inhibitor for 6 hours and then stimulated with LPS (1 μg/ml) for 48 hours. The cell culture media were centrifuged at 5000 rpm and supernatants were stored at −80° C. The media was thawed and used for chemiluminescent secretory alkaline phosphatase (SEAP) assay using Great EscAPe™ SEAP reporter assay system according to protocol essentially as described by the manufacturer, (BD Biosciences, Palo Alto, Calif.) using a 96-well chemiluminescence plate reader. All the suggested controls by manufacturers were used in the assay.

Statistical analysis: Data are expressed as the mean±SD. All the Data were analyzed by student's t-test using Microsoft Excel 2003 software. $P<0.05$ was considered as statistically significant.

II. Results

Figure 1A:
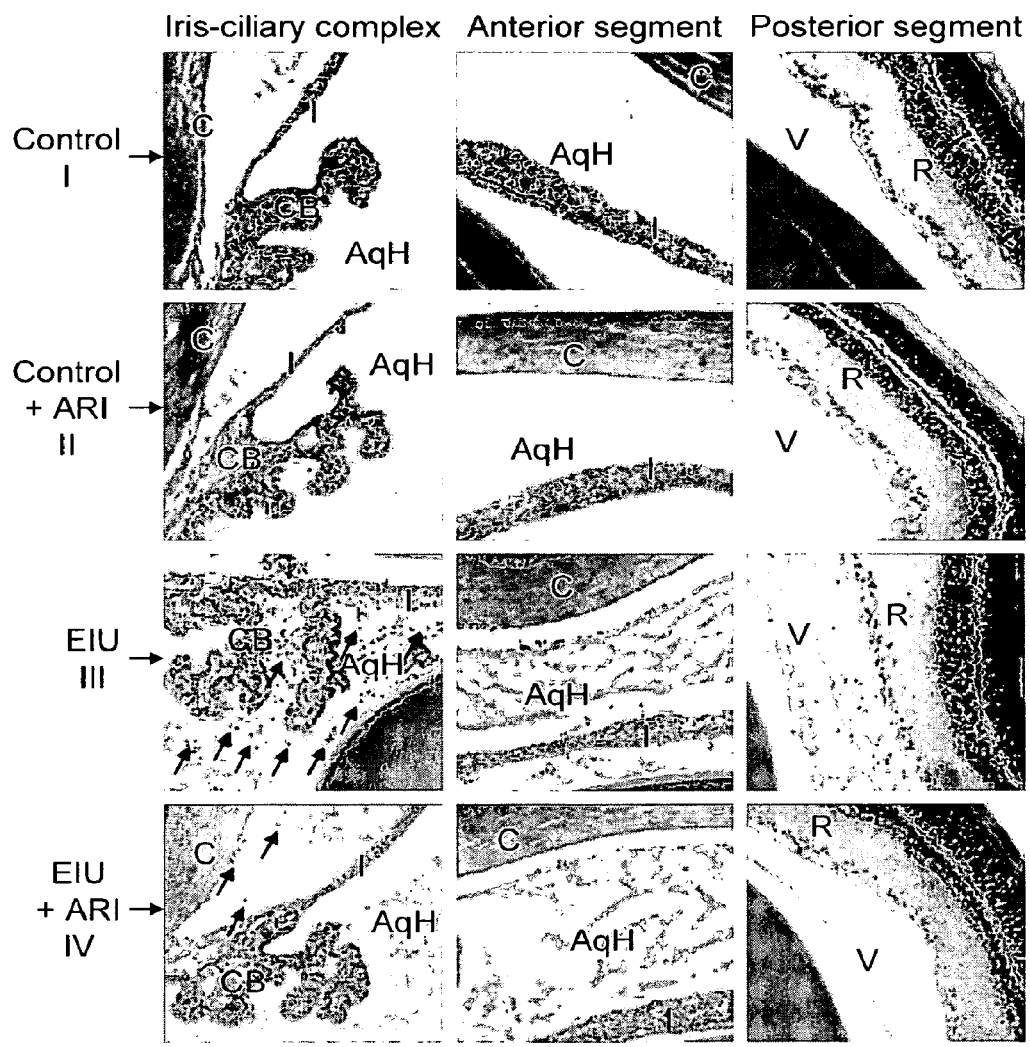
FIGS. 1A-1B Inhibition of AR prevents LPS-induced inflammatory cell infiltration and protein concentration in aqueous humour.
Figure 1B:
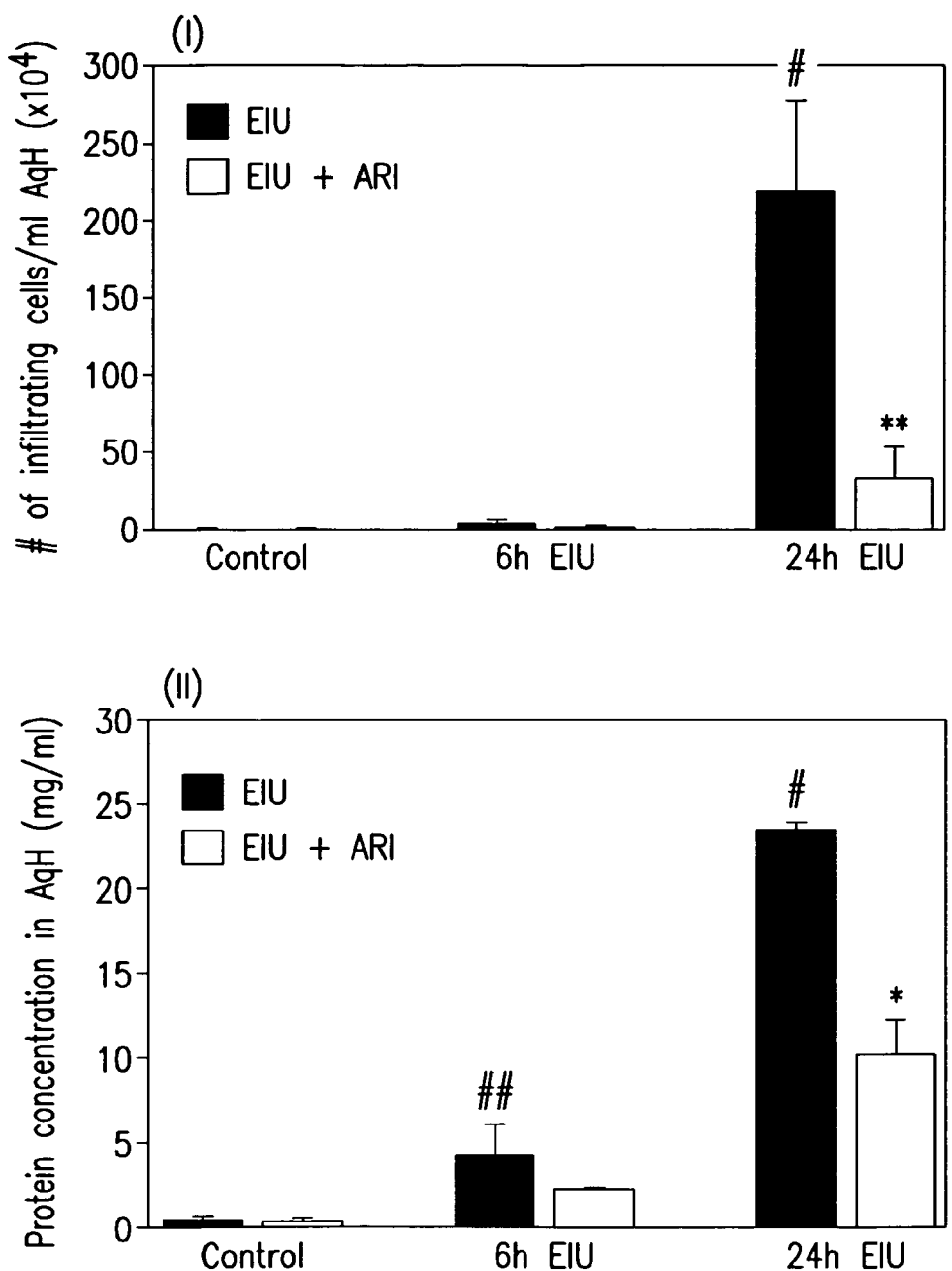

Effect of AR inhibition on Leukocyte infiltration and protein concentration induced by EIU. To investigate the effect of AR inhibitor on EIU-induced infiltration of inflammatory cells such as leukocytes and monocytes in the anterior chamber and aqueous humor (AqH) of the eye, saggital sections of rat eyes were stained with H&E (FIG. 1A) and examined under bright-field microscope. EIU caused infiltration of a large number of cells which was significantly prevented by AR inhibitor (FIG. 1A (III) and FIG. 1A (IV)). No significant infiltration of cells was observed in either carrier or zopolrestat alone-treated groups (FIG. 1A (I) and 1A (II)). In EIU-rat eyes a few infiltrating cells were also present in the vitreous chamber (VC) but none were observed in AR inhibitor+ EIU or control rats. The accumulation of infiltrating cells in AqH was also confirmed by manually counting the cells in AqH by using a hemocytometer (FIG. 1B (I)). As observed in histological examination, the manual cell counting also demonstrated a significant (>200-folds) increase in the infiltration of inflammatory cells in the aqueous humor of EIU-rat eyes which was significantly (>80%) prevented by AR inhibitor treatment of the EIU-rats (FIG. 1B (I)). In addition, the total protein concentration in the AqH of EIU-rat eyes was increased up to 23-fold as compared to control rat eyes and inhibition of AR prevented it by >60% (FIG. 1B (II)). These results suggest that AR inhibition prevents EIU-induced infiltration of inflammatory cells as well as release of inflammatory proteins in the AqH of rat eyes.

Figure 2A:
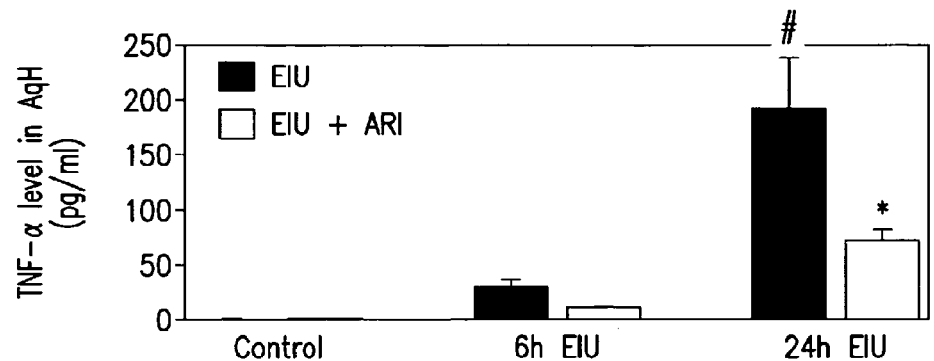
FIGS. 2A-2B Inhibition of AR prevents TNF-α secretion in LPS.
Figure 2B:
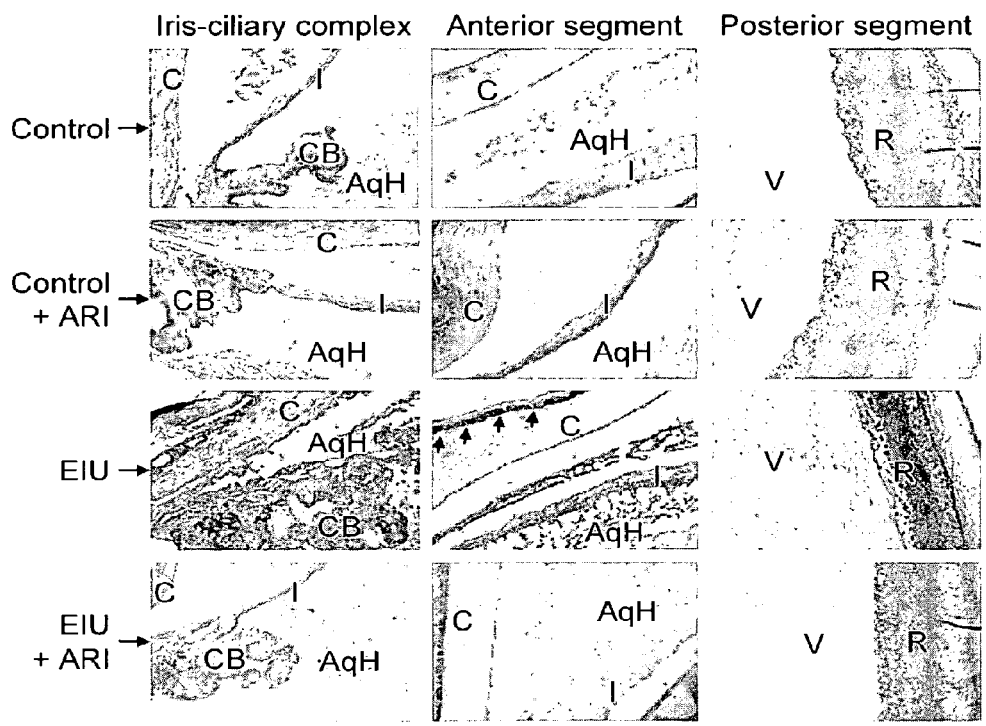
Figure 3A:
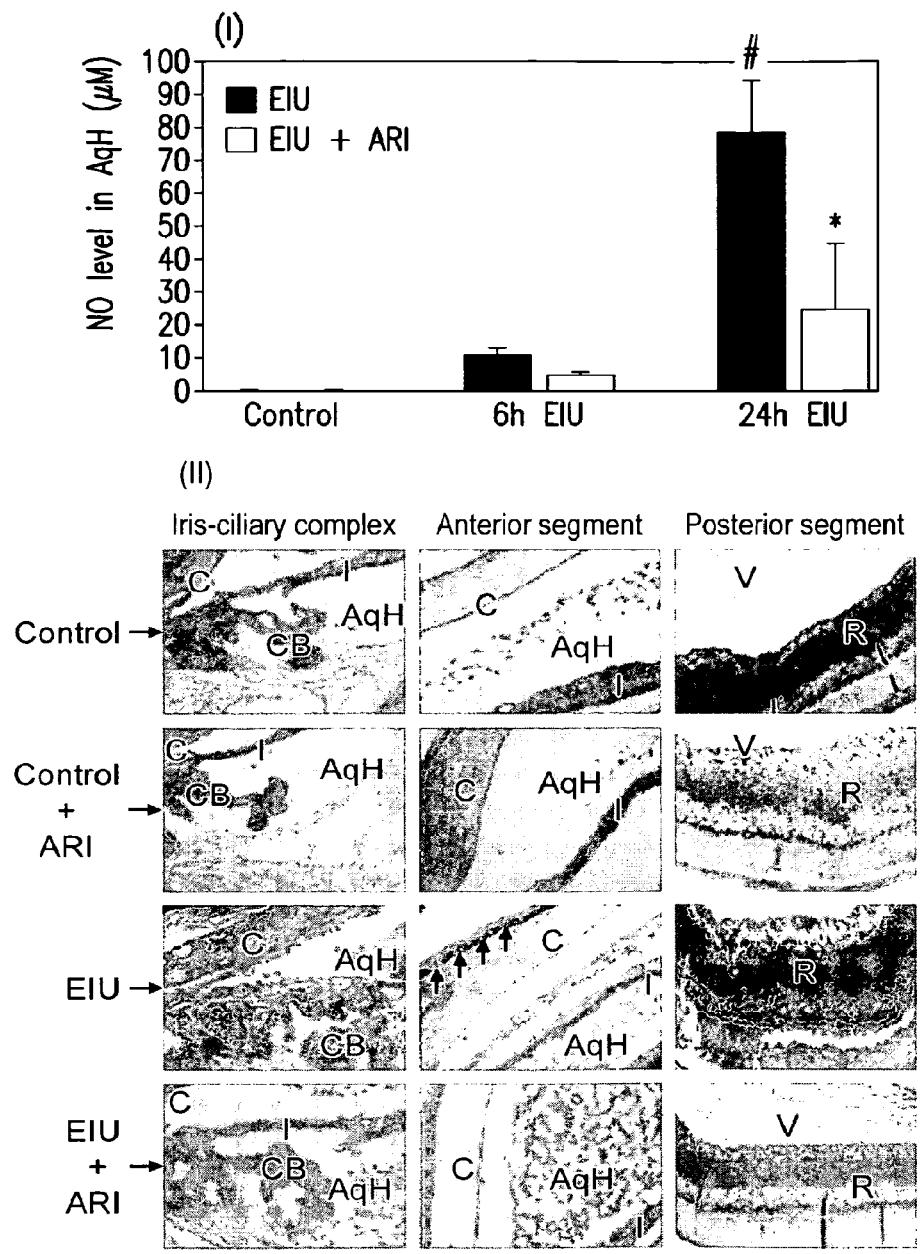
FIGS. 3A-3B Inhibition of AR prevents NO and $PGE_2$ secretion in EIU. (3AI and 3BI) NO and $PGE_2$ levels in the AqH collected 6 and 24 h after LPS injection were measured by using ELISA kits as described in Methods. Each value represents the mean±SD (n=4), #p<0.001 vs control group and *p<0.001. (3AII and 3BII) Serial sections of para-formaldehyde-fixed rat eyes were immuno-stained with antibodies against iNOS (AII) and Cox-2 (BII) and observed under EPI-800 microscope (A representative picture is shown (n=4); Magnification 200×). AqH, aqueous humor; C, Cornea; CB, ciliary body; I, Iris; V, Vitreous; R, Retina.
Figure 3B:
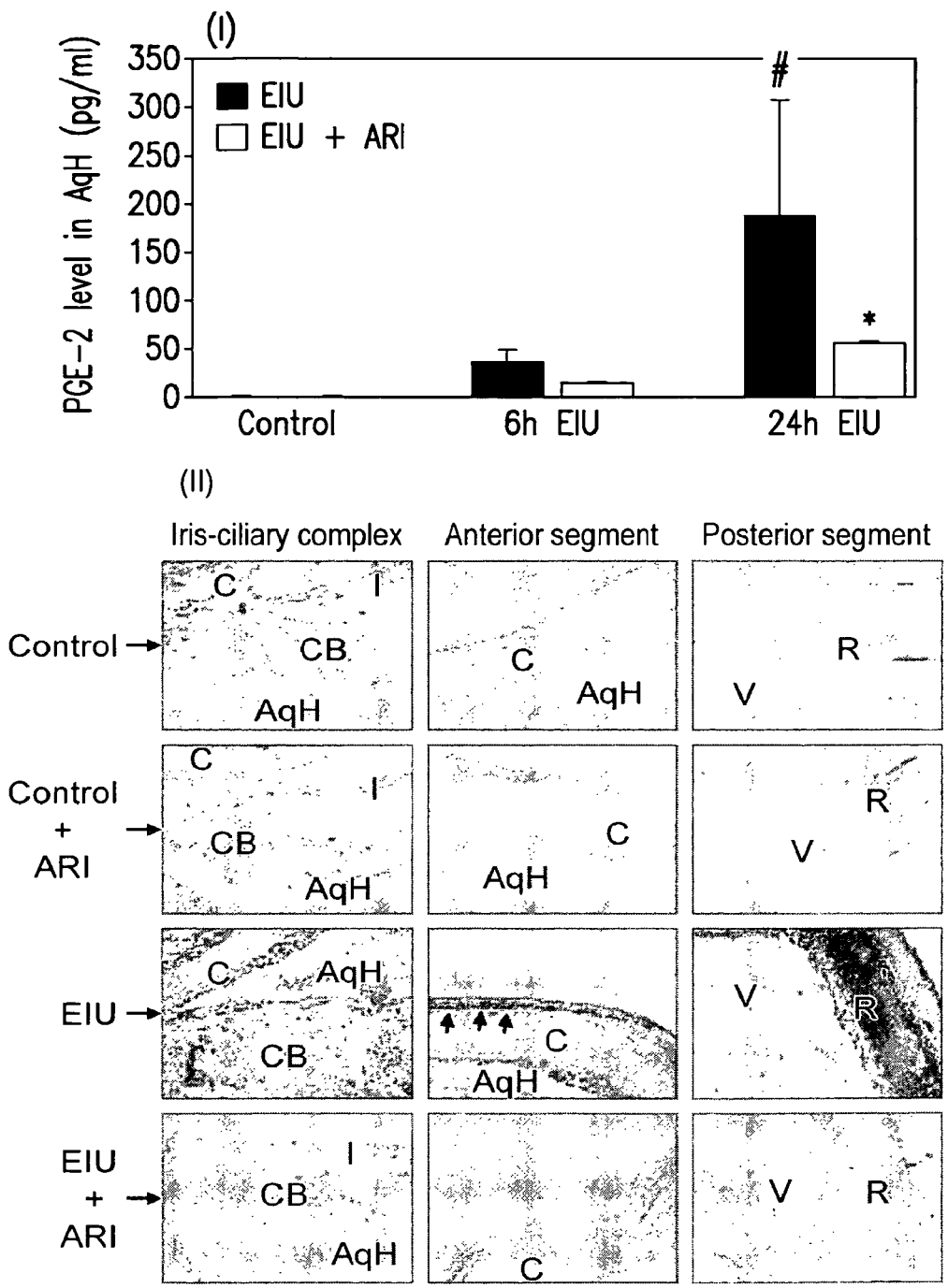

Effect of AR inhibition on EIU-induced inflammatory markers in AqH. Next, the effect of AR inhibition on the levels of inflammatory markers (TNF-α, NO and $PGE_2$) in the AqH of EIU-rat eyes was examined. TNF-α was non-detectable in the AqH of control animals while in EIU-rats the TNF-α levels were approximately 30 and 190 ng/ml after 6 and 24 h of EIU-induction (FIG. 2A). Treatment of rats with zopolrestat followed by EIU significantly (>60%) reduced the TNF-α concentration in AqH during both time points. These results were further confirmed by immunohistochemistry using antibodies against TNF-α. The EIU-rats showed a significant intensity of antibody staining in iris-ciliary complex, and AqH region whereas, AR inhibitor-treated animals showed diminished antibody staining, indicating that AR inhibition prevents accumulation of TNF-α (FIG. 2B, left panel). Since EIU-induced acute inflammation is not restricted to anterior chamber only (Rosenbaum et al., 1980; Altan-Yaycioglu et al., 2006), the inventors immunohistochemically examined the levels of TNF-α in vitreous region as well. The results shown in FIG. 2B (right panel) show increased levels of TNF-α in vitreous, and retina of LPS-treated rats as compared to control groups which was significantly prevented by AR inhibitor. This indicates that inflammatory markers increased in the posterior segment of eye including vitreous and retinal wall of EIU-rat eyes and treatment of rats with AR inhibitor followed by endotoxin injection significantly reduced the levels of TNF-α in vitreous chamber and retinal wall. It indicates that increase in inflammatory markers in EIU is mediated by AR. Similarly, the levels of NO and $PGE_2$ (FIG. 3A (I) and FIG. 3B (I)) significantly increased in the aqueous humor of EIU rat eyes as compared to control and treatment with AR inhibitor significantly (>70%) reduced the levels of NO as well as $PGE_2$. Since NO and $PGE_2$ are produced by inducible nitric oxide synthase (iNOS) and cyclooxygenase-2 (Cox-2) enzymes respectively, the inventors immunohistochemically examined the expression of iNOS and Cox-2 proteins in the various regions of eye. The EIU rat eyes showed increased expression of iNOS and Cox-2 proteins in the iris-ciliary body complex, corneal epithelium in anterior segment and retinal wall in the posterior segment (FIG. 3A (II) and FIG. 3B (II)). AR inhibitor significantly prevented the expression of iNOS as well as Cox-2.

Effect of AR inhibitor on expression of AR in EIU rat eyes: Since AR is oxidative stress response protein and increased AR protein levels have been observed in many of the pathogenesis (Galvez et al., 2003; El-Remessy et al., 2003; Iwata et al., 1999), the inventors next examined the AR expression in EIU-rat ocular tissues. Immuno-histochemical staining of EIU-rat eye sections using antibodies against AR showed a strong staining for AR in cells at iris-ciliary body, corneal epithelium layer, and retina (FIG. 4A) as compared to control eyes. However, the AR inhibitor in endotoxin-injected rat ocular tissues significantly inhibited the expression of AR, suggesting that AR inhibition prevents signaling events responsible for its own gene expression.

Figures 4A, 4B:
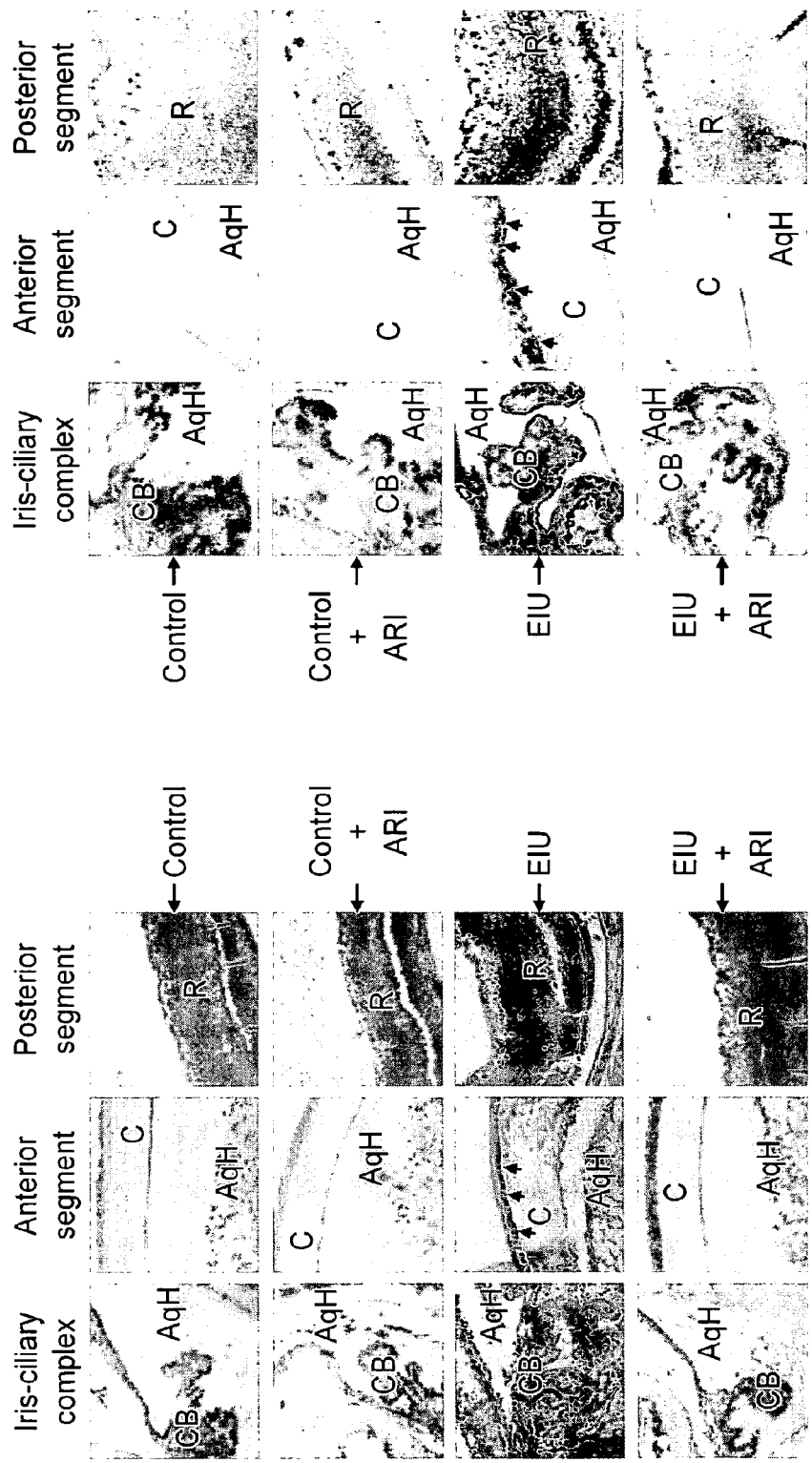
FIGS. 4A-4B Inhibition of AR prevents AR expression and activation of NF-κB in EIU.

Effect of inhibition of AR on NF-κB activity in EIU rat eyes: Since redox-sensitive transcription factor NF-κB transcribes various inflammatory markers genes including that of TNF-α, iNOS and Cox-2, and AR (Iwata et al., 1999; Xiao 2004), the inventors next examined the effect of AR inhibition on endotoxin-induced activation of NF-κB in rat eyes. The eye sections were immuno-stained with antibodies against active subunit of NF-κB (phosphor-p65) which is released after the degradation of the inhibitory protein IκB and does not cross react with the inactive NF-κB complex. After 3 h of EIU, NF-κB positive cells were observed in the iris-ciliary body complex, corneal epithelium in anterior segment, and retina in posterior segment of the eye (FIG. 4B). In contrast the number of NF-κB positive cells in the anterior as well as posterior chambers of AR inhibitor-treated EIU eyes were significantly decreased (FIG. 4B).

Figure 5:
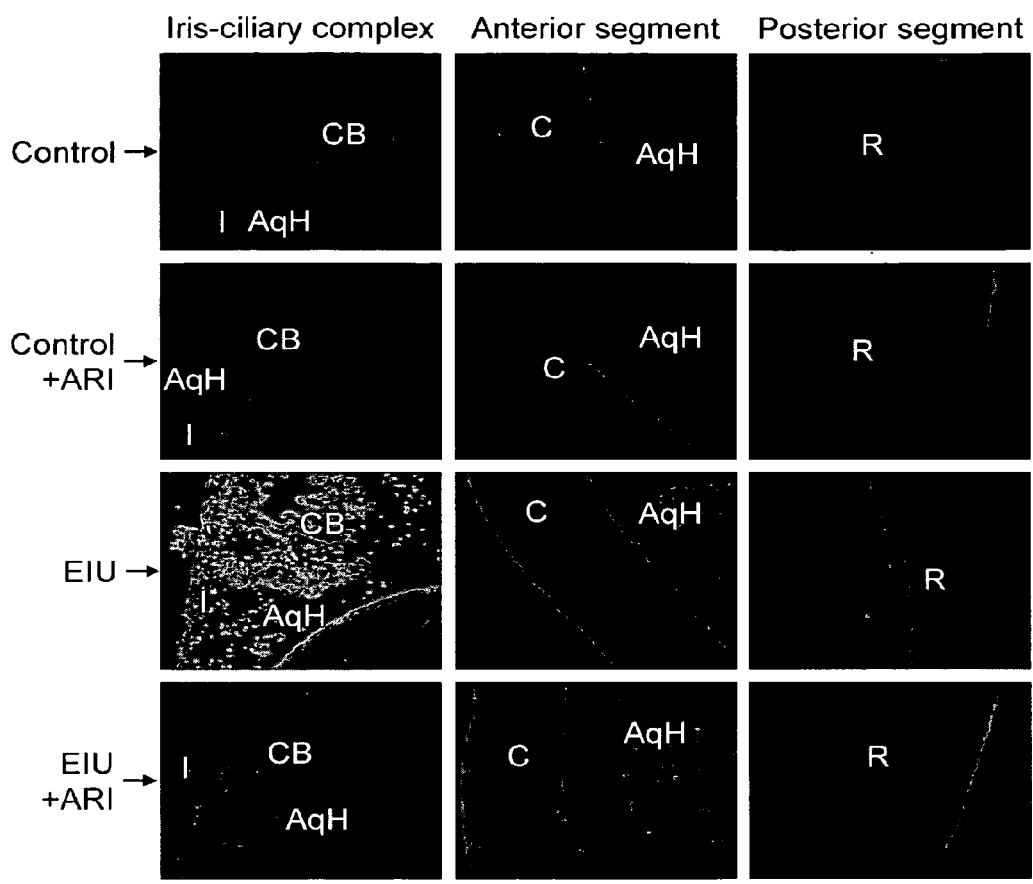
FIG. 5 Inhibition of AR prevents ROS generation in EIU. Serial sections of para-formaldehyde-fixed rat eyes were stained with ROS-sensitive dye dihydroethidium (DHE) for 30 min at 37° C. followed by acquisition of images using a fluorescence microscope (A representative picture is shown (n=4); Magnification 200×). AqH, Aqueous humor; I, Iris; CB, Ciliary body; C, Cornea; R, Retina.

Effect of AR inhibition on endotoxin-induced oxidative stress: Since NF-κB is a ROS sensitive transcription factor and AR inhibition prevents EIU-induced NF-κB activation, the inventors next examined the effect of AR inhibition on ROS generation in EIU rat eyes. As shown in FIG. 5, the increased fluorescence corresponding to the increased level of ROS was observed in the iris-ciliary body complex, corneal epithelium in the anterior segment and inhibition of AR significantly prevents LPS-induced ROS. Further, LPS-also increased the ROS levels in the retinal region of the posterior segment of the rat eyes and the increase was prevented by AR inhibitor.

Figure 6A:
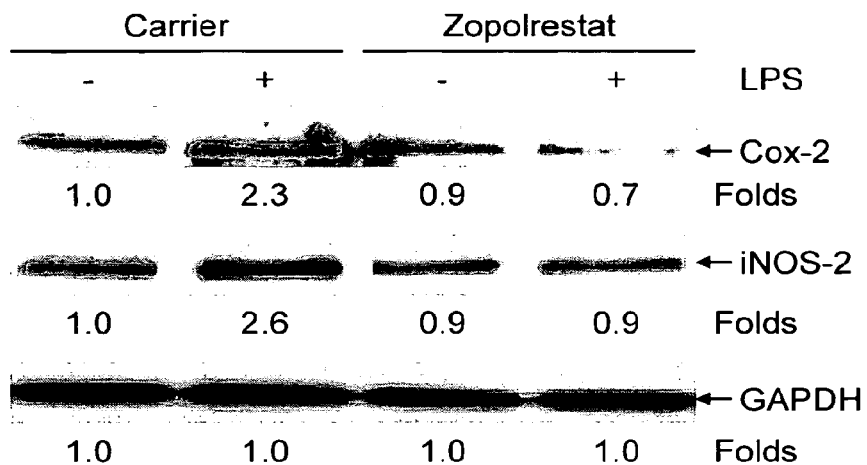
FIGS. 6A-6B Effect of inhibition of AR on the LPS-induced inflammatory response in human monocytic cells.
Figure 6B:
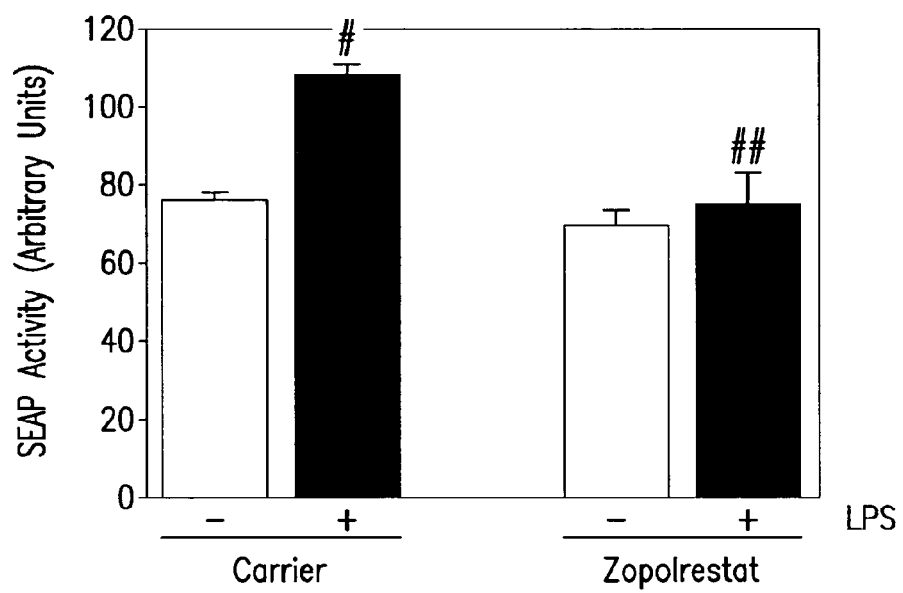
Figure 7:
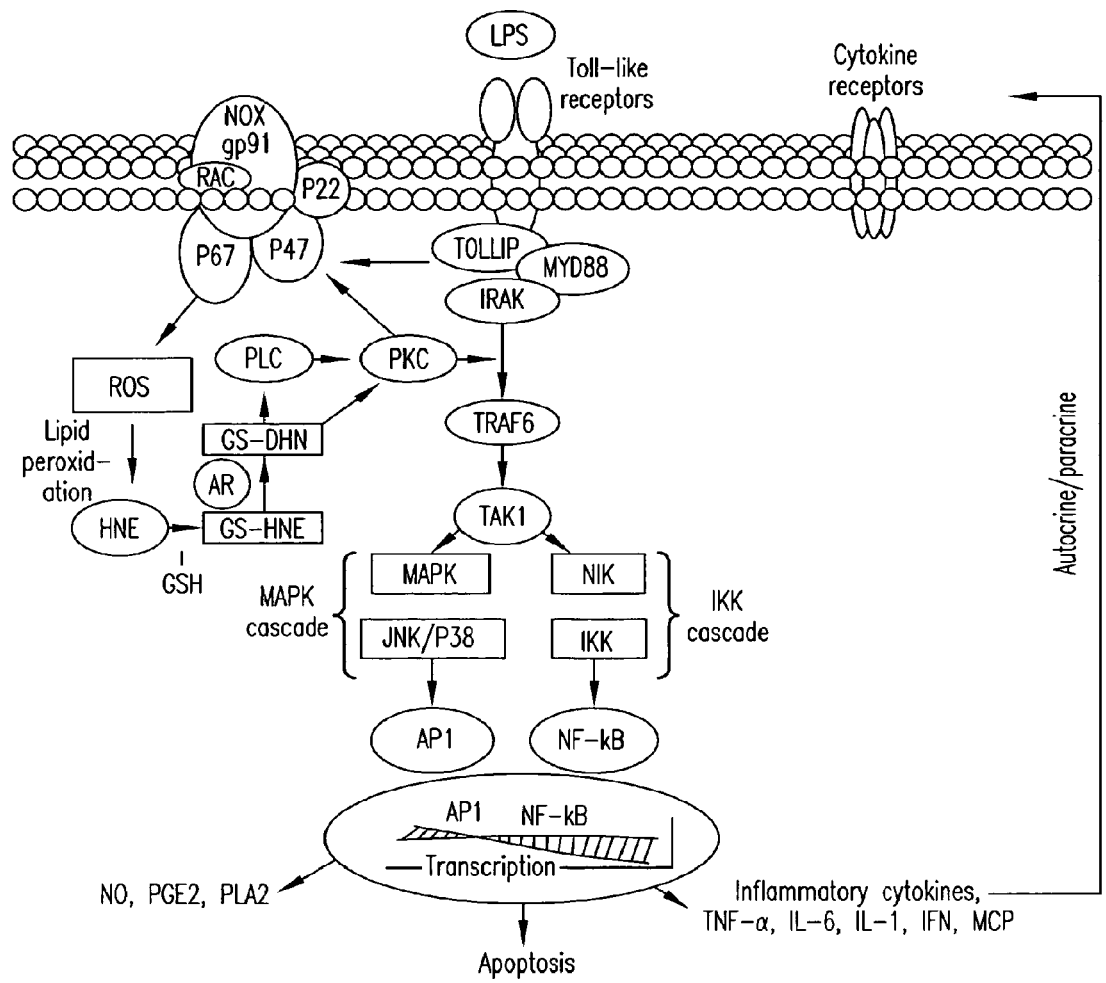
FIG. 7 Role of aldose reductase (AR) in inflammatory signals.

Effect of AR inhibition on LPS-induced NF-κB-dependent inflammatory protein expression in human monocytic cell line: The in-vivo observations made in EIU were confirmed by in-vitro studies using U-937 (human monocytic cells) cell line as these are one of the major infiltrating cells in AqH during EIU. Incubation of U-937 cells with LPS caused 2-, and 3-fold increase in the expression of Cox-2 and iNOS proteins, respectively compared to control cells. However, in the presence of AR inhibitor, LPS-induced increase in Cox-2 and iNOS proteins in monocytic cells was significantly prevented (FIG. 6A). Furthermore, the activation of NF-κB in LPS-treated cells by secretary alkaline phosphatase (SEAP)-reporter assay were assessed and the results showed a ~40% increase in the SEAP activity (corresponding to NF-κB activation) as compared to controls, which was significantly prevented by AR inhibition (FIG. 6B).

Example 2

Aldose Reductase Inhibition and Asthma

Studies show that AR plays a pivotal role in inflammation, irrespective of the cause such as cytokines, chemokines, endotoxins and growth factors. Since anti-inflammatory drugs are being used therapeutically in asthma and AR inhibitors prevent the formation of inflammatory markers as well as their cellular effects (Ramana et al., 2006a; Ramana et al., 2006b), it was reasoned that they should be excellent drugs to treat asthma pathogenesis, irrespective of the source or causative factor.

Role of AR in inflammatory diseases: The inventors investigated the effects of AR inhibition on cytokine-, and high glucose-induced apoptosis of human lens epithelial cells (HLECs) and VECs and proliferation of VSMCs. AR inhibitors significantly attenuated TNF-α-induced proliferation of VSMCs (Ramana et al., 2002) and apoptosis of HLECs (Ramana et al., 2003). Further, AR inhibitors also prevented the activation of caspase-3 and degradation of nucleosomal histones by high glucose or TNF-α in HLECs and by LPS in macrophages (Ramana et al., 2006a; Pladzyk et al., 2006). Also, AR inhibition attenuated cytokine- and high glucose-induced NF-κB and AP1 activation in all the cell lines studied (Srivastava et al., 2005). Furthermore, AR inhibition or ablation by siRNA prevented the TNF-α or LPS-induced activation of DAG/PLC/PKC/NF-κB in VSMCs and macrophages (Ramana et al., 2002; Ramana et al., 2006a). These results raised the interesting and significant question of how AR regulates the signaling events initiated by cytokines and growth factors, and how inhibition of AR prevents cytokine and growth factor signaling? Understanding this role of AR will provide pharmacological tools for eventual therapeutic interventions to control cell proliferation, apoptosis, tissue repair, and to prevent the cytotoxicity of cytokines and chemokines which are increased during oxidative stress. More importantly, these results provide a mechanistic link with inflammation.

Since LPS is known to cause apoptosis through the expression of proinflammatory markers such as PGE2, Cox-2 and iNOS, the effect of AR inhibition was investigated in cellular models. The inventors demonstrate that LPS-induced apoptosis of HLECs and macrophages and inflammatory response, as determined by a significant increase in the TNF, MMP2, MMP9, PGE2 and Cox-2 levels, are prevented (75 to 95%) by inhibiting or ablating AR (Ramana et al., 2006a; Pladzyk et al., 2006). The in vitro studies were extended to mice. Mice were injected intraperitoneally with a single dose of LPS (4 µg/kg body wt)±ARI, sorbinil, 25 mg/Kg body wt/day, and killed them on days 1, 3, and 7 after LPS injection. Cytokine and chemokine levels were determined in the serum, as well as in such tissues as liver, heart and spleen (Ramana et al., 2006a). The results showed that LPS significantly increased various cytokines, chemokines, cAMP, Cox-2 and PGE2 in the serum and various tissues, and that the increases were 75 to 95% decreased by AR inhibition. It was also demonstrated that AR inhibition significantly increased the LD50 of LPS in mice from 14 mg to 20 mg (Ramana et al., 2006b). The investigations have been extended to other inflammatory diseases such as colon cancer and uveitis and have shown that inhibition of AR prevents colon cancer progression in nude mice xenografts and uveitis in rats (Tammali et al., 2006). Thus, the inventors contemplate that AR plays pivotal role in the pathophysiology of inflammation, which is backed by strong evidences obtained using cellular as well as animal models.

Figure 8A:
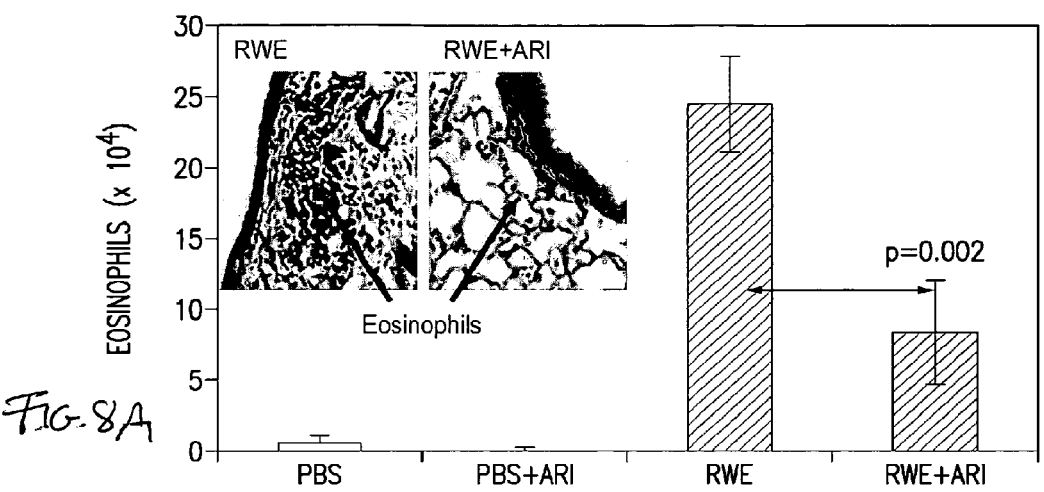
FIGS. 8A-8B AR inhibition prevents accumulation of eosinophils in airways and in sub-epithelial regions (inset) induced by Ragweed Pollen extract in mice model of asthma.
Figure 8B:
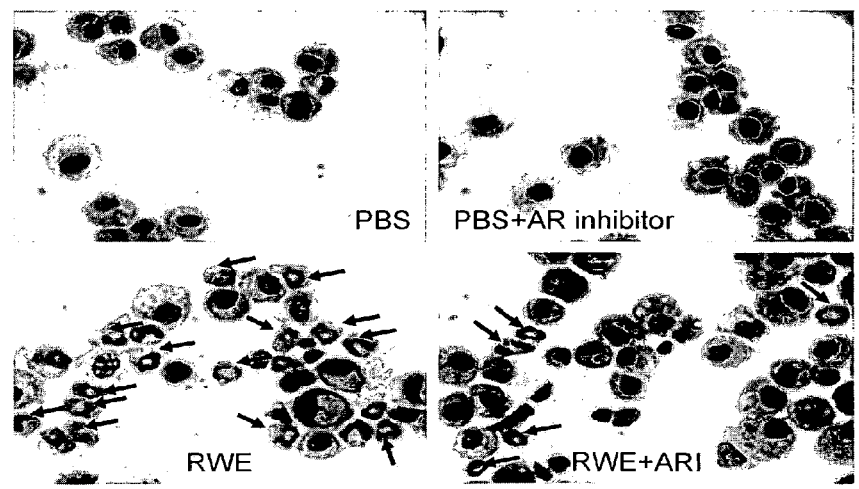
Figure 9A:
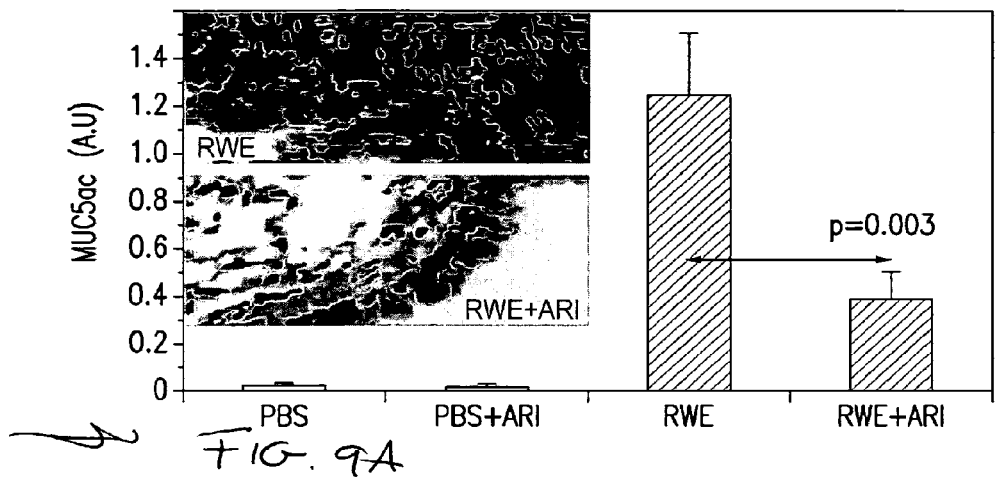
FIGS. 9A-9B AR inhibition prevents Ragweed Pollen extract-induced (FIG. 9A) accumulation of Muc5ac levels in the BAL and (FIG. 9B) hyperresponsiveness in mice model of asthma.
Figure 9B:
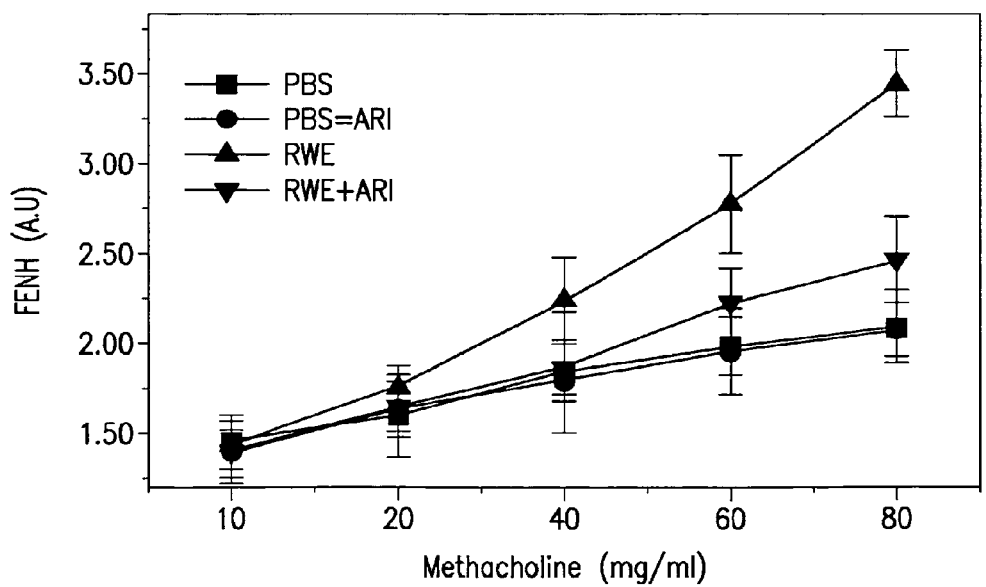
Figure 10A:
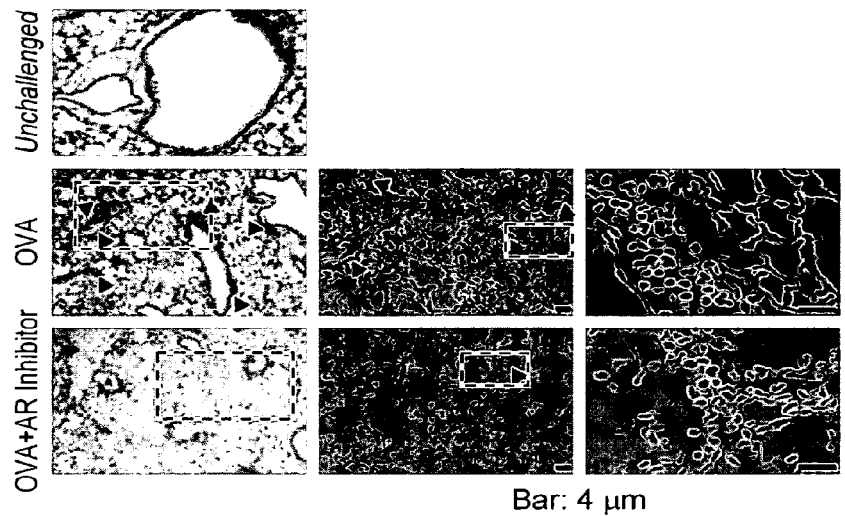
FIGS. 10A-10B Effect of AR inhibition on (FIG. 10A) Th2 cytokine production and (FIG. 10B) inflammatory cell (eosinophils) infiltration in ovalbumin (OVA)-induced murine model of asthma.
Figure 10B:
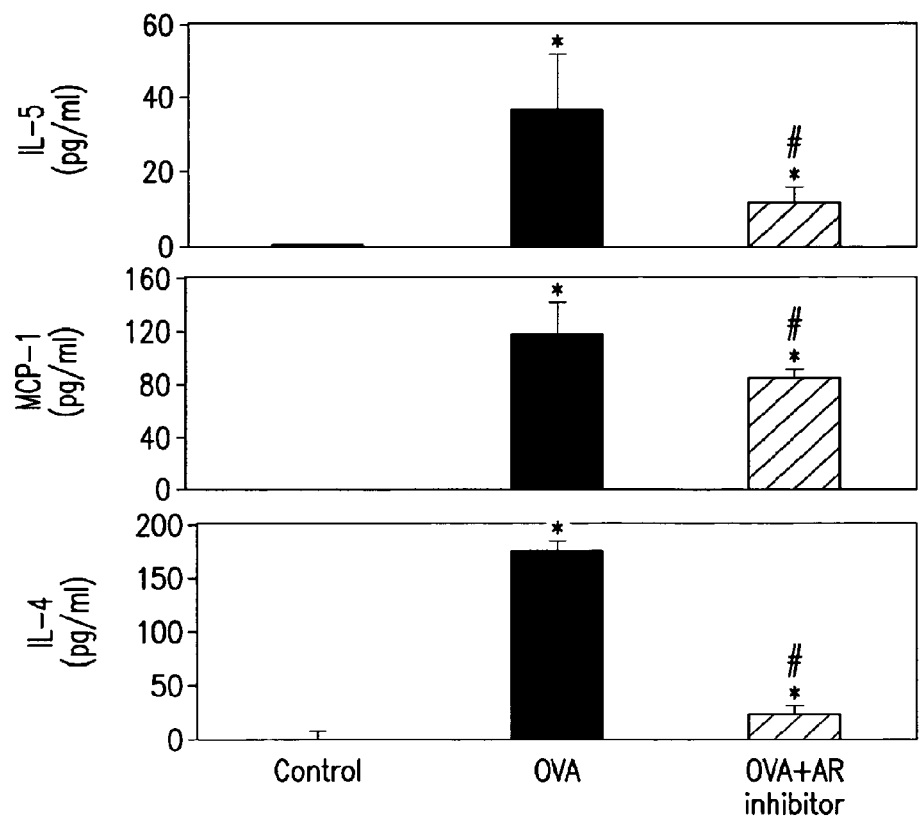

Aldose reductase in Asthma pathogenesis: Human small airway epithelial cells (SAEC) were incubated with AR inhibitors followed by stimulation with RW and TNF-α. Inhibition of AR prevented RW and TNF-α-induced apoptosis and NF-κB activation indicating that AR inhibition could be a novel strategy to control airway inflammation. The inventors therefore, used mice models of allergic airway inflammation using RW and OVA sensitized mice. AR inhibition also prevented RW-induced eosiniphil infiltration, production of mucus in goblet cells, and hyperresponsiveness in mice (FIG. 8 and FIG. 9). Further inhibition of AR significantly prevented OVA-induced eosinophils infiltration and production of IL-5, IL-4 and MCP-1 (FIG. 10). Additional studies were required to examine the inhibition of AR as it relates to the prevention of asthma.

Thus, based upon our results of prevention of formation and effects of inflammatory markers in cellular and animal models especially those with sepsis, atherosclerosis, cardiac preconditioning, restenosis in carotid arteries, cardiomyopathy and colon carcinogenesis by AR inhibition, the inventors contemplate that AR inhibition would prevent asthma. Studies support this contention since AR inhibitors significantly prevented airway inflammation in RW and OVA mice models. AR inhibitors can be used to prevent chronic inflammation mediated by cytokines, chemokines and other proinflammatory markers such as Cox-2, PGE2 and iNOS, irrespective of the initiating cause such as autoimmune or infection. Since such inflammatory markers are major risk factors for airway inflammation leading to respiratory complications, AR inhibition is an excellent therapeutic strategy in such disorders.

A. Effect of AR Inhibitors in OVA-, and RW-induced Airway Inflammation in Mice Asthma Models.

Bronchial asthma is a chronic inflammatory disease of the airways characterized by airway eosinophilia, goblet cell hyperplasia with mucus hypersecretion, and hyperresponsiveness to inhaled allergens. The inventors studied AR inhibition and asthma pathogenesis using mouse models for asthma to determine effects of two structurally distinct AR inhibitors (sorbinil and zopolrestat) on OVA-induced bronchial inflammation and airway hyper-responsiveness.

OVA sensitization: Six to eight-weeks old C57BL/6 wild type mice (n=6 each group) (obtained from Jackson Labs) are sensitized with i.p. injections of 100 µg Grade V chicken ovalbumin (OVA) (Sigma-Aldrich, St. Louis Mo.) mixed with 2 mg aluminum hydroxide in saline once a week for 2 consecutive weeks, followed by a challenge with aerosolized OVA a week after the second sensitization. The mice are challenged by placing them in groups of six in a Plexiglas chamber and are exposed for 30 min to aerosolized OVA (3% OVA in saline). The OVA aerosol is generated by a Bennett nebulizer (DeVilbiss, Pa.). In the experimental groups, mice receive i.p. injections of sorbinil or zopolrestat (25 mg/kg body wt) 24 h prior and 12 h post challenge. Control groups are not sensitized or challenged with OVA instead are given saline (Mustapha et al., 2006).

RW Sensitization: Eight-week-old C57BL/6 wild type mice (n=6 each group) are sensitized with RW as described (Boldogh et al., 2005; Bacsi et al., 2005). Briefly, mice are sensitized with two intraperitoneal administrations of endotoxin-free RW, 150 µg/100 µl/injection, combined in a 3:1 ratio with Alum adjuvant, on days 0 and 4. On days 9 and 10, animals are injected with AR inhibitors (25 mg/kg) every 12 h for 48 hours. On day 11, parallel groups of mice are challenged intranasally with RW (100 µg). Control groups of mice are challenged with equivalent volumes of PBS.

Histological examination: Animals are killed by $CO_2$ asphyxiation and their lungs fixed with formalin for histological analysis, subjected to BAL, or collected for homogenization to prepare cell lysates for cytokines or IgE determination. Formalin-fixed lungs can be sectioned and subjected to hematoxylin and eosin (H&E) or Periodic Acid-Schiff (PAS) staining using standard protocols. Collected BAL fluids can be subjected to cyto-spin and stained with H&E for the assessment of number and percent of eosinophils. Spleens may also be removed to prepare cell suspension for Th1 cytokines assessment. Serum is used to analyze various cytokines and chemokines and IgE levels.

Bronchoalveolar Lavage (BAL): In the mice killed by $CO_2$ asphyxiation, the trachea is cannulated just below the larynx. A flexible polyurethane tube (outer diameter, 0.4 mm) attached to a blunt 23-gauge needle is inserted ~6 mm into the trachea. BAL is performed by injecting 0.3 ml of saline at room temperature; the fluid is withdrawn and stored on ice. This procedure is repeated a total of three times and the collected fluid pooled.

Cytology: BAL fluid is centrifuged at 1000×g for 10 min at 4° C., and the resulting supernatant stored immediately at −80° C. The cell pellets are resuspended in 250 µl of phosphate-buffered saline (PBS) containing 2% bovine serum albumin (BSA), and the total cell count is determined with an automated counter (Coulter Electronics, Hialeah, Fla.) and recorded as the total number of inflammatory cells per milliliter. The cell suspension is adjusted to a density of 200 cells/µl, and 100 µl of the diluted suspension is centrifuged at 800×g for 10 min with a Cytospin onto coated Superfrost Plus microscope slides. The cells on the slides are air-dried, fixed for 30 s with Diff-Quik fixative, and then stained first with Diff-Quik solution I for 60 s and then with Diff-Quik solution II for 60 s. After washing with deionized water for 30 s, the slides are allowed to dry before application of the mounting media and a cover slip. Differential counts are performed for ~200 cells according to standard morphological criteria. A pathologist, assessing the different inflammatory cell types is blinded to the treatment groups.

Immunohistochemistry: Lung sections are immunostained for the expression of protein-HNE adducts, AR, p65 NF-κB, ICAM-1, VCAM-1 and other inflammatory markers such as Cox-2 and iNOS as described in Mustapha et al., 2006. Western blot analysis of the lung homogenates are carried out to confirm immunohistochemical studies using specific antibodies.

Cytokine assessment: The concentrations of total IL-4, IL-5, GM-CSF, IL-10, IFN-γ, IL-12, IL-13 are determined using the Bio-Rad Bioplex System for mouse Th1 and Th2 cytokines as described in Mustapha et al., 2006. The levels of MMP2, MMP9, Cox, PGE-2 and NO are measured in BAL by using specific ELISA kits.

IgE quantification: IgE is quantified by sandwich ELISA technique. The plates are coated overnight with rabbit anti-OVA antibodies (Serotec, Raleigh, N.C.) at 4° C. and then blocked with 1% BSA in PBS for 1 h at 37° C. Samples, along with IgE Standards are prepared and added to appropriate wells and incubated for 3 h at 4° C. Polyclonal goat anti-IgE antibodies, followed by HRP-conjugated rabbit anti-goat antibodies are used to detect bound IgE. 3,3'5,5'-Tetramethylbenzidine is used to develop the plates and values determined by an ELISA plate reader at 490 nm.

Determination of airway responsiveness to methacholine: Airway responsiveness is measured in unrestrained, conscious mice 3 days after the last challenge (Prieto et al., 2006). Mice are placed in a barometric plethysmographic chamber, and baseline readings taken and averaged for 3 min. Aerosolized methacholine in increasing concentrations (from 2.5 to 50 mg/ml) will be nebulized through an inlet of the main chamber for 3 min. Readings are taken and averaged for 3 min after each nebulization and enhanced pause (Penh) is determined. Penh, calculated as (expiratory time/relaxation time−1)×(peak expiratory flow/peak inspiratory flow) according to the manufacturers' protocol, is a dimensionless value that represents a function of the proportion of maximal expiratory to maximal inspiratory box pressure signals and a function of the timing of expiration. Penh is used as a measure of airway responsiveness to methacholine. Results are expressed as the percentage increase of Penh following challenge with each concentration of methacholine, where the baseline Penh (after saline challenge) is expressed as 100%. Penh values averaged for 3 min after each nebulization are evaluated.

Determination of mucin production: Mucin production in the epithelial cells is assessed by periodic acid Schiff (PAS)-staining of formalin-fixed, paraffin-embedded lung sections. The stained sections are analyzed as above and representative fields are photographed with a Photometrix CoolSNAP Fx camera mounted on a NIKON Eclipse TE 200 UV microscope. MUC5AC levels in the BAL is assessed by ELISA using commercially available anti-MUC5AC monoclonal antibody (Lab Vision, CA, USA) as described (Mustapha et al., 2006; Boldogh et al., 2005).

B. Mechanism(s) of AR Mediation in Bacterial Endotoxin (LPS)-, RW-, TNF-α and 4-hydroxynonenal (HNE)-induced Signals in Airway Epithelial Cells.

The inventors contemplate that AR participates in cytotoxic signaling initiated by various oxidants such as LPS, RW, TNF and HNE and by regulating the activation of transcription factors such as NF-κB and AP1 via protein kinase network comprised of PKC, MAPK, JNK, and IKK and expression of inflammatory markers, leading to airway epithelial cell apoptosis. Human small airway epithelial cells (SAEC) are treated with oxidants±AR inhibitors, or AR RNAi and subjected to the protocols described in the following studies to identify the molecular signaling events and target(s) of AR action.

Methods: SAEC (Cambrex BioScience Inc, Walkersville, Md.) grown in small airway growth medium (SAGM; Cambrex BioScience Inc) are divided in groups based on the treatments: The cells are incubated with AR inhibitors (10 μM; sorbinil or zopolrestat) or transfected with AR siRNA or scrambled siRNA followed by stimulation with LPS (1 μg/ml); RW (50 μg/ml); TNF-α (2 ng/ml) or HNE (1 μM). Cell growth and apoptosis are measured by cell counting, MTT assay, thymidine incorporation, caspase-3 activation, cell death ELISA and finally cell cycle analysis. For signaling studies, the cells are pretreated with 10 μM AR inhibitors for 24 h and then stimulated with LPS, RW, TNF and HNE. After different incubation periods (0, 15, 30, 60, 90, 120 min for protein kinases and transcription factors and 24 h for expression of inflammatory markers), the effect of oxidants±AR inhibitors or siRNA on the activation of PKC, MAPK, ERK, P38, JNK, and IKK are determined. The effects of inhibiting AR on the activation of transcription factors such as NF-κB, AP-1, SP1 and OCT1 and expression of inflammatory markers are determined as described herein.

Apoptosis: Cell viability is determined by cell counting, MTT assays and [$^3$H]-thymidine incorporation (Ramana et al., 2002). Cell death is determined by "cell Death ELISA kit", caspase-3 activation, and Hoechst nuclear staining that determines the morphological changes in the nuclei undergoing apoptotic death (Ramana, et al., 2006a; Pladzyk et al., 2006). Activation of caspase-3 is a marker for apoptosis, and is measured by two methods [1] in vitro cleavage of caspase-3 substrate and [2] the in vivo activation of caspase-3 that leads to the cleavage of PARP. The cleavage products are identified by Western blot analysis with anti-PARP antibodies. Apoptosis is also determined by "Annexin V staining and DNA content by FACS" in the absence and presence of AR inhibitors or siRNA.

Oxidative stress: Oxidative stress is the main mediator of antigen-induced airway inflammation. Therefore, the inventors examine the effects of inhibiting or ablating AR on the oxidative stress; lipid peroxidation, generation of toxic LDAs such as HNE, as well as activation of NADPH oxidase and formation of superoxide radicals. As a crude indicator of oxidative stress, the inventors quantify the endogenous GSH levels after treating the SAEC cells with LPS±AR inhibitors or AR SiRNA. Several studies show that a decrease in the levels of GSH may cause cytotoxic effects under various stress conditions; this is an accepted index of increased oxidative stress (Wisnewski et al., 2005; Klock et al., 2003). Total ROS production in the cells is measured fluorimetrically, as well as by flow cytometry, using 2',7'-Dichlorodihydrofluorescein (H2DCF), a fluorescent dye that interacts with oxygen-free radicals, using a fluorometry or FACS scan analysis (Pladzyk et al., 2006). The inventors use the flow cytometry core facility available to all UTMB investigators on a fee-for-service basis. The generation of superoxide is measured by a spectrophotometric assay, as well as by a luminescence assay using NBT and coelenterazine, respectively (Ramana et al., 2006c). The inventors will measure the NADPH oxidase activity in the SAEC.

Lipid peroxidation and HNE levels: Several stress conditions show increased HNE generation and protein-HNE formation, especially in cells and tissues undergoing cell death (Rahman et al., 2002; Hamilton et al., 1996). Since the inventors have previously shown that AR efficiently catalyzes the reduction of these aldehydes and their GS-conjugates with a Km in the low micromolar range (Srivastava et al., 1995;

Ramana et al., 2000; Dixit et al., 2000; Singh et al., 2006), the inventors contemplate that by inhibiting or ablating AR they are able to modulate oxidative injury and alter its cytotoxic consequences. To quantify the lipid peroxidation, HNE formation is used as a marker for lipid peroxidation. HNE-protein adducts are quantified using an ELISA kit per the supplier's instructions. The concentration of GS-HNE and its AR-reduced product GS-DHN is measured by HPLC analysis of culture media. The GS-HNE and GS-DHN peaks are identified by ESI/MS as described by Ramana et al., 2006c.

NF-κB and AP-1: The activation of NF-κB and AP1 is measured by EMSA, and also with a NF-κB reporter gene (Clontech) as described earlier (Ramana et al., 2006a; Ramana et al., 2006b; Ramana et al., 2006c; Pladzyk et al., 2006).

NF-κB upstream signals: The enzymes PKC, IKK, and MAPK are the main kinases for the phosphorylation of IκB-α, whereas p38 MAPK and JNK are the main kinases involved in the activation of AP1. Polyclonal antibodies against phosphorylated and unphosphorylated anti-p44/42 MAPK, ERK1/2 and the IKK isoforms (IKK-α, IKKβ and IKK-γ) are used to determine the effects of AR inhibition on oxidant-induced activation of kinases. The phosphorylation of JNK and p38 is studied by using phospho-specific Abs against JNK and p38. Finally, the inventors determine total PKC activity using Promega SignaTECT PKC assay system, per the manufacturer's instructions (Ramana et al., 2006a).

Inflammatory marker expression: Inflammatory cytokines and chemokines will be measured and confirmed by RT-PCR (Ramana et al., 2006a, Tammali et al., 2006).

AR-catalyzed LDAs in airway inflammation: The inventors contemplate that the reduced form of GS-HNE, GS-DHN (a representative of GS-LDAs) is the main mediator for the activation of PLC pathway that activates PKC, which further activates NF-κB and AP1 and cause inflammation. Therefore, the GS-DHN-induced activation of PLC, PKC and other kinases that activate NF-κB and AP1 are investigated in airway epithelial cells. The SAEC are incubated with GS-DHN (1 µM) for different time intervals (0-180 min). The cells are harvested, cytoplasmic and nuclear extracts prepared as described (Ramana et al., 2006a). The NF-κB and AP1 activities and protein kinases are determined as described above.

Statistical Analysis of the Data: Data collected from in vitro and in vivo experiments is analyzed by ANOVA, followed by Bonferroni post-hoc analyses for least significant difference. Differences are considered significant at $P<0.05$.

Example 3

Aldose Reductase Inhibition and Antigen-induced Allergic Airway Inflammation

I. Materials and Methods

Reagents: Small airway epithelial basal medium (SABM), and small airway epithelial growth media (SAGM™) bullet-kit; and one Reagentpack™ containing Trypsin 0.025%/EDTA 0.01%, Trypsin neutralizing solution and HEPES buffered saline solution were purchaged from Cambrex Bio Sciences Walkersvillle, Inc. (Walkersville, Md.). Sorbinil and Zopolrestat were obtained as gift from Pfizer (New York, N.Y.). Dimethyl sulfoxide (DMSO) was obtained from Fischer scientific (Pittsburgh, Pa.). Ragweed pollens (RW) were purchased from Greer's laboratory (Lenoir, N.C.). Nitrite/Nitrate and $PGE_2$ assay kits were obtained from Cayman Chemical Inc (Ann Arbor, Mich.). Human IL-6 and IL-8 ELISA kits were from Diaclone (Stamford, Conn.) and R&D systems, respectively. Antibodies against COX2, iNOS, Bcl-XL, Bax, GAPDH, cyclin-D1 and E2F2 were from Santa Cruz Biotechnology Inc. (Santa Cruz, Calif.); and antibodies against phospho-IκB were from Cell signaling (Danvers, Mass.). Dihydroethidium (DHE) fluorescent dye was purchased from Molecular Probes, Invitrogen (Carlsbad, Calif.) and polyclonal antibodies against human recombinant AR were made for us by Alpha diagnostic intl. (San Antonio, Tex.). The reagents used in the electrophoretic mobility shift assay (EMSA) and Western blot analysis were obtained from Sigma. All other reagents used were of analytical grade.

Cell Culture: Small Airway Epithelial cells (SAEC) obtained from Cambrex Bio Science Walkersville, Inc. (Walkersville, Md.) contains normal human SAEC from distal airspace of 18 yr old male donor. The cells were cultured according to the supplier's instructions at 37° C. in humidified atmosphere containing 95% air and 5% $CO_2$ in small airway epithelial basal medium (SABM) with supplements containing 52 µg/ml bovine pituitary extract, 0.5 ng/ml human recombinant epidermal growth factor (EGF), 0.5 µg/ml epinephrine, 1 µg/ml hydrocortisone, 10 µg/ml transferrin, 5 µg/ml insulin, 0.1 ng/ml retinoic acid (RA), 6.5 ng/ml triiodothyronine, 50 µg/ml Gentamicin/Amphotericin-B (GA-1000), and 50 µg/ml fatty acid-free bovine serum albumin (BSA).

Annexin V Staining and Flow Cytometry: Approximately $2\times10^5$ SAEC/well were plated in 6-well plates in triplicate for each group. After 24 hours, the medium was replaced with serum-free SABM with or without zopolrestat (20 µM). The cells were induced by RW (150 µg/mL) and incubated for 18 h. Apoptotic cell death was examined using the annexin V-FITC/PI, (molecular probes, Invitrogen) according to the manufacturer's instructions. Twenty thousand events were acquired for each sample and analyzed by flow cytometry using the LYSIS II software (FACScan, BD Pharmingen).

In situ detection of superoxide: Dihydroethidium (DHE, Molecular Probes) staining for superoxide was carried out as described previously. Briefly, Approximately $1\times10^5$ cells were seeded on chambered slides and starved in serum-free SABM with or without AR inhibitor for 24 h. The cells were treated with RW for 16 h. SAEC were rinsed with cold PBS and incubated in PBS containing HEt (2.5 mmol/L) at 37° C. for 15 minutes. Cells were rinsed in PBS and mounted with Vectashield Hard Set™ mounting medium with DAPI (Vector Laboratories Inc., Burlingame, Calif.). The image of ethidium staining was measured with a Nikon epifluorescence microscope with a 585 nm long-pass filter. Generation of superoxide in the cells was demonstrated by strong red fluorescent labeling.

Electrophoretic Mobility Shift Assay (EMSA): The SAEC were pretreated with or without AR inhibitors for 24 h in starving medium, followed by treatment with Ragweed pollens (RW) (50 µg/ml) for 2 h at 37° C. The nuclear extracts were prepared as described. Briefly, SAEC were harvested and washed with cold PBS and suspended in 0.1 ml of hypotonic lysis buffer containing protease inhibitors for 10 min. The cells were then lysed with 5 µl of 10% Nonidet P-40. The homogenate was centrifuged (6000 rpm; 1 min.), and supernatant containing the cytoplasmic extracts was stored frozen at −80° C. The nuclear pellet was resuspended in 50 µl ice-cold nuclear extraction buffer. After 30 min of intermittent mixing, the extract was centrifuged (12000 rpm; 15 min.), and supernatants containing nuclear extracts were secured. The protein content was measured by the Bradford method. If they were not used immediately, they were stored at −80° C. The Consensus oligonucleotides for NF-κB and AP-1 transcription factors were 5'-end labeled using T4 polynucleotide kinase. EMSA was performed as described. The specificity of the assay was examined by competition with an excess of unlabeled oligonucleotide and supershift assays with antibodies to p65.

NF-κB-dependent reporter secretary alkaline phosphatase expression assay: The SAEC ($1\times10^5$ cells/well) were plated in 24-well plates, serum-starved in SABM for 24 hours with or without AR inhibitors, sorbinil and zopolrestat (20 μM), and transiently transfected with pNF-κB-secretory alkaline phosphatase (SEAP) construct or control plasmid pTAL-SEAP DNA (Clontech, Palo Alto, Calif.) using the LipofectAMINE Plus reagent. After 6 hours of transfection, medium was replaced with fresh medium and cells were treated with RW (50 μg/mL) for 48 hours. The cell culture medium was harvested, centrifuged and supernatant was analyzed for SEAP activity, essentially as described by the manufacturer (Clontech, Palo Alto, Calif.), using a 96-well chemiluminescence plate reader.

RNA Interference Ablation of AR in SAECs: The ablation of AR mRNA was essentially carried out as described in the art. Briefly, $2\times10^5$ SAECs were plated in a 6-well plate and grown until ~80% confluency. The cells were incubated with serum-free medium containing the AR-siRNA (AATCGGT-GTCTCCAACTTCAA (SEQ ID NO:1)) or scrambled siRNA (AAAATCTCCCTAAATCA TACA (SEQ ID NO:2); control) to a final concentration of 100 nM and the RNAiFect™ transfection reagent (Qiagen). The cells were cultured for 48 h at 37° C., and AR expression was determined by measuring AR protein by Western blot analysis using anti-AR antibodies.

Prostaglandin E2, IL-6 and IL-8 Assays: The SAEC were plated in 6-well plates at a density of $2\times10^5$ cells/well in triplicate for each group. After 24 hours, the medium was replaced with serum-free SABM with or without zopolrestat (20 μM). The growth-arrested and AR ablated cells were stimulated with RW (50 μg/mL) for another 24 hours. The medium was collected from each well, centrifuged and supernatant was analyzed for PGE2 (Cayman Chemical Co., Ann Arbor, Mich.); IL-6 (Diaclone, Stamford, Conn.) and IL-8 (R&D systems Inc, Minneapolis, Minn.) by using an ELISA kits according to the manufacturer's instructions.

Determination of IL-6, IL-8 and Cox-2 expression by RT-PCR: The SAECs were grown in 6-well plates at a density of approximately $3.0\times10^5$ cells/well. After approximately 80% confluence, cells were serum-starved in the presence or absence of sorbinil or zopolrestat (20 μM) for 24 h and then stimulated with 50 μg/ml RW for 6 h. Total RNA from SAECs was isolated by using RNeasy kit (Qiagen) as per supplier's instructions. Aliquots of RNA (0.5-1.0 μg) isolated from each sample were reverse transcribed with Omniscript and Sensiscript reverse transcriptase one-step RT-PCR system with HotStar Taq DNA polymerase (Qiagen) at 55° C. for 30 min followed by PCR amplification. The oligonucleotide primer sequences were as follows: 5'-ATGAACTCCT TCTCCA-CAAGCGC-3' (SEQ ID NO:3) (sense) and 5'-GAAGAGC-CCTCAGGCTGGACTG-3' (SEQ TD NO:4) (antisense) for IL-6; 5'-ATGACTTCCAAGCTGGCCGTGGCT-3' (SEQ ID NO:5) (sense) and 5'-TCT CAGCCCTCTTCAAAAACT-TCTC-3' (SEQ ID NO:6) (antisense) for IL-8; 5'-TGAAAC-CCACTCCA AACACAG-3' (SEQ ID NO:7) (sense) and 5'-TCATCAGGCACAGGAGGAAG-3' (SEQ ID NO:8) (antisense) for Cox-2; and 5'-ATCTGGCACCACACCTTCTA-CAATGAGCTGCG-3' (SEQ ID NO:9) (sense) and 5'-CGTC ATACTCCTGCTTGCTGATCCACATCTGC-3' (SEQ ID NO:10) (antisense) for β-actin. PCR was carried out in a PCR Sprint thermal cycler (Thermo electron corporation, Milford, Mass.) under the following conditions: initial denaturation at 95° C. for 15 min followed by 35 cycles of 94° C. 1 min, 62° C. 1 min, 72° C. 1 min, and then 72° C. 10 min for final extension. PCR products were electrophoresed with 1.5% agarose-1xTAE gels containing 0.5 μg/ml ethidium bromide. The densitometric analyses of the blots were performed by using Kodak 1D image analysis software.

Western blot analysis: Fourty micrograms of cytoplasmic protein extracts, prepared as described earlier were resolved on 10% SDS-PAGE. After electrophoresis, the proteins were electro transferred to a nitrocellulose membrane, blocked with 5% nonfat milk in TBST, and probed with antibodies against COX-2, NOS2, Bcl-xL, Bax, cyclin D1, E2F2 (1:1, 000 dilution) for 2 hr. The blot was then washed, exposed to HRP-conjugated secondary antibodies (1:5,000 dilution) for 1 hr, and the antigen-antibody complex was detected by enhanced chemiluminescence (Amersham Pharmacia Biotech, Piscataway, N.J., USA).

Animals: BALB/c mice were purchased from Harlan Sprague-Dawley (San Diego, Calif., USA). All animal experiments were performed according to the National Institutes of Health Guide for Care and Use of Experimental Animals and approved by UTMB Animal Care and Use Committee (#9708038-05).

Sensitization and challenge of animals: Eight-weeks-old female animals were sensitized with ragweed pollens (RW) as previously described (Boldogh et al., 2005; Bacsi et al., 2005 and 2006). Briefly, mice were sensitized with two intraperitoneal administrations of endotoxin-free RW 150 μg/100 combined with Alum adjuvant in a 3:1 ratio, on days 0 and 4. On days 9 and 10, animals were treated with AR inhibitor (i.p. 25 mg/kg body weight) every 12 h for total duration of 48 h. On day 11, parallel groups of mice (n=6-8) were challenged intranasally with RW (100 μg), Control groups of mice were challenged with equivalent volumes of PBS.

Evaluation of allergic inflammation: To evaluate inflammation, animals from all experimental groups were euthanized on day 14 with ketamine (135 mg/kg body wt) and xylazine (15 mg/kg body wt), and the lungs were lavaged with two 0.8 ml aliquots of ice-cold PBS. The cells were collected by centrifugation (1000 g, for 10 min at 4° C.) re-suspended in one ml of PBS, and total cell counts were determined.

Differential cell counts were performed on cytocentrifuge preparations stained with hematoxylin and eosin. After bronchoalveolar lavage (BAL), the lungs were fixed with 4% paraformaldehyde, embedded in paraffin, and sectioned to 5 μm. Lung sections were stained with hematoxylin and eosin (Boldogh et al., 2005). Perivascular and peribronchial inflammation and cell composition in the BAL were evaluated by a pathologist, blinded to treatment groups, to obtain data for each lung. The representative fields were photographed with a Photometrix CoolSNAP Fx camera mounted on a NIKON Eclipse TE 200 UV microscope.

Mucin production in the epithelial cells was assessed by periodic acid Schiff (PAS)-staining of formalin-fixed, paraffin-embedded lung sections. The stained sections were analyzed as above and representative fields were photographed with a Photometrix CoolSNAP Fx camera mounted on a NIKON Eclipse TE 200 UV microscope (Boldogh et al., 2005, Bacsi et al., 2006).

To determine mucin levels, BAL was centrifuged at 12,000 rpm for 10 min at 4° C., and the supernatants were kept at −80° C. until assayed. MUC5AC levels in the BAL were assessed by ELISA using commercially available anti-MUC5AC monoclonal antibody (1-13M1) (Lab Vision, Fremont, Calif., USA). Briefly, MUC5AC present in the BAL was captured to a microtiter plate and a second antibody conjugated to biotin was added. After 30 min' incubation with streptavidin-horseradish peroxidase (HRP) plates were washed and peroxidase substrate was added to obtain colorimetric product, which was quantified by spectrometry. Data are expressed as arbitrary units relative to a MUC5AC standard curve that was included on each plate (Boldogh et al., 2005).

Airway responsiveness was measured in unrestrained, conscious mice 3 days after the last challenge. Mice were placed in a barometric plethysmographic chamber, and baseline readings were taken and averaged for 3 min. Aerosolized methacholine in increasing concentrations (from 10 to 80 mg/ml) were nebulized through an inlet of the main chamber for 3 min. Readings were taken and averaged for 3 min after each nebulization and enhanced pause (Penh) was determined. Penh, a dimensionless value, represents a function of the ratio of peak expiratory flow to peak inspiratory flow and a function of the timing of expiration, was calculated as (expiratory time/relaxation time$^{-1}$)×(peak expiratory flow/peak inspiratory flow) according to the manufacturers' protocol. Penh correlates with pulmonary airflow resistance or obstruction and was used as a measure of airway responsiveness to methacholine.

Statistical analysis: For the cell culture experiments data presented are mean±SE and P values were determined by unpaired Student's t test. For animal studies, data collected from in vitro and in vivo experiments were analyzed by ANOVA, followed by Bonferroni post-hoc analyses for least significant difference. P<0.05 was considered as statistically significant.

II. Results

Figures 1, 11A:
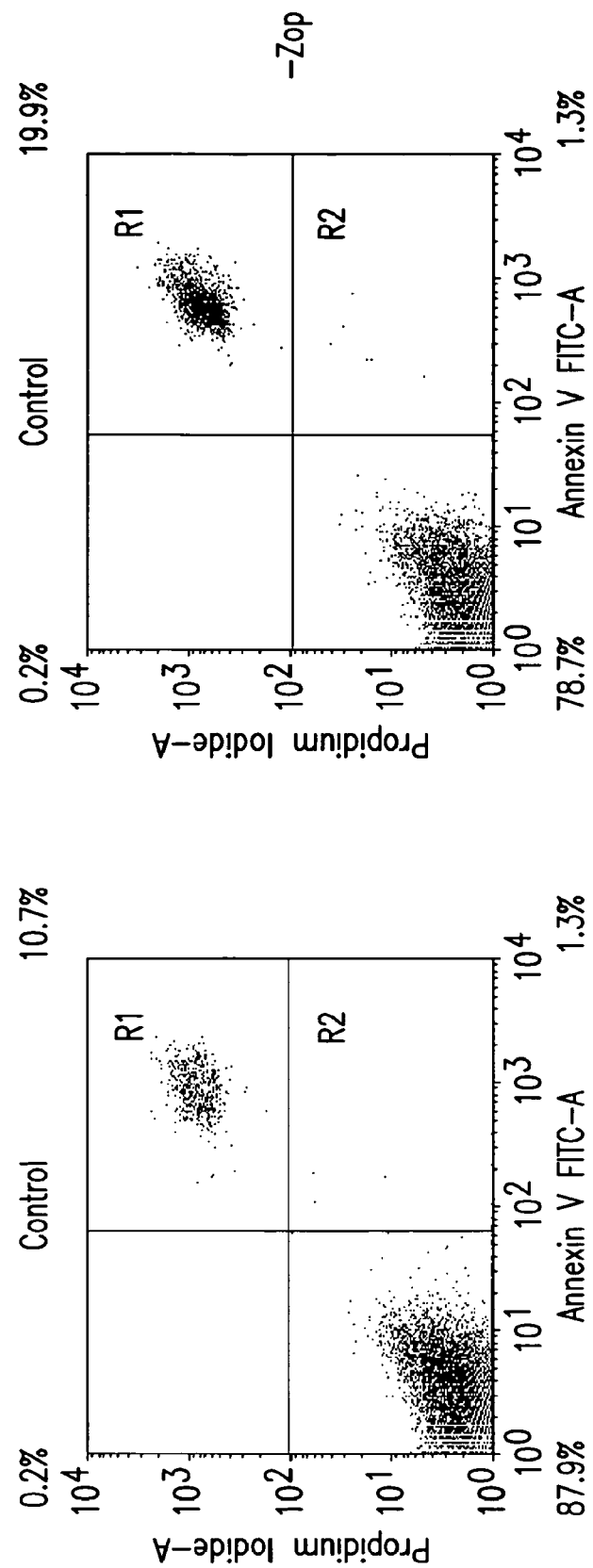
FIGS. 11A-11B Inhibition of AR prevents RW-induced apoptosis and cell death in SAEC.
Figures 2, 11A:
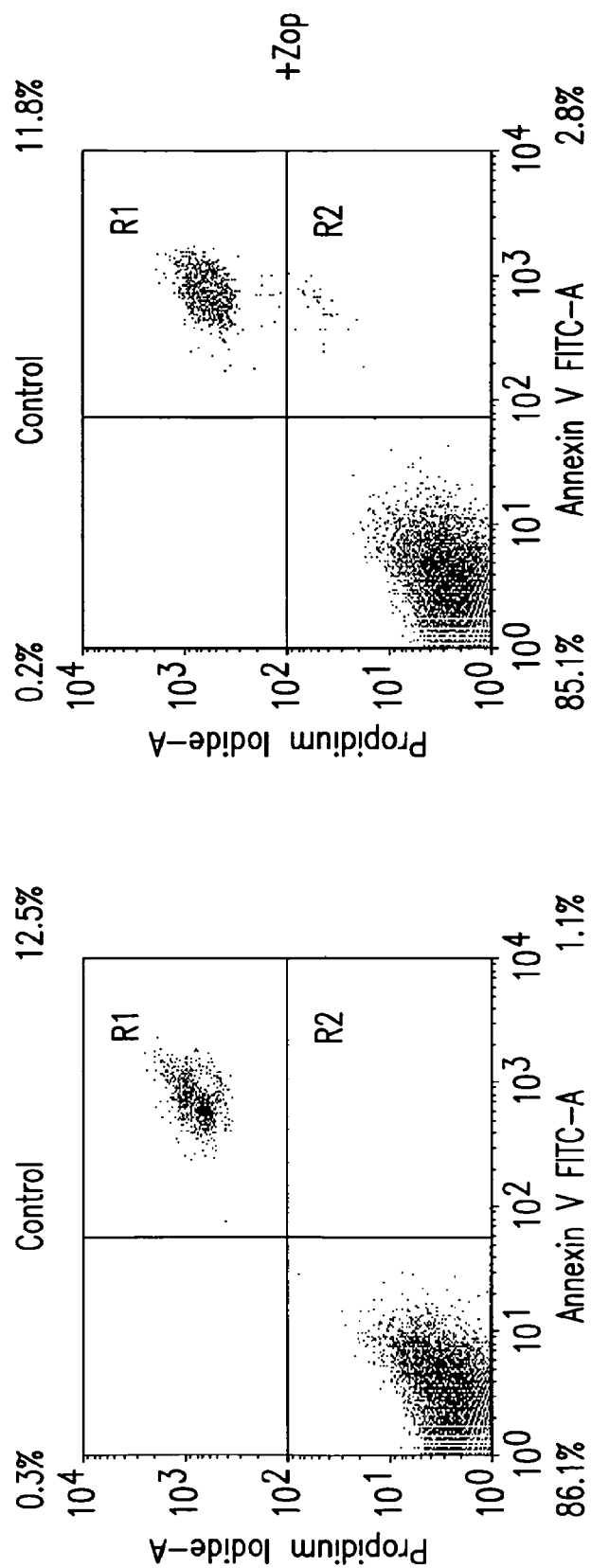
Figure 11B:
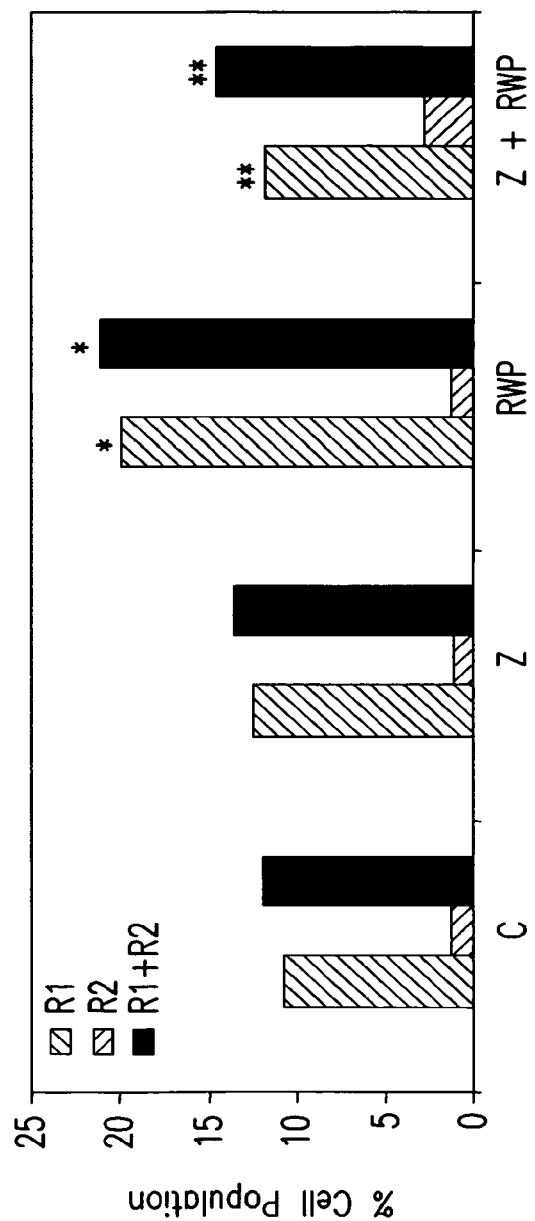

Effect of AR Inhibition on RW-induced apoptosis in SAEC: To determine the effects of AR inhibition on RW-induced apoptosis in the SAEC, annexin-V staining was used. Annexin-V binds to the inverted phosphotedyl serine in the cells undergoing apoptosis. Propidium-iodide (PI) was used as the indicator of the cell mortality. The results in FIG. 11 suggest that RW caused increased cell death (over 50%) in 18 h as compared to the control cells. Preincubation of the cells with AR inhibitor, zopolrestat, significantly (p<0.01) prevented RW-induced cell death by >80% (FIG. 11). Under similar conditions, AR inhibition alone did not cause apoptosis of SAEC.

Figure 12:
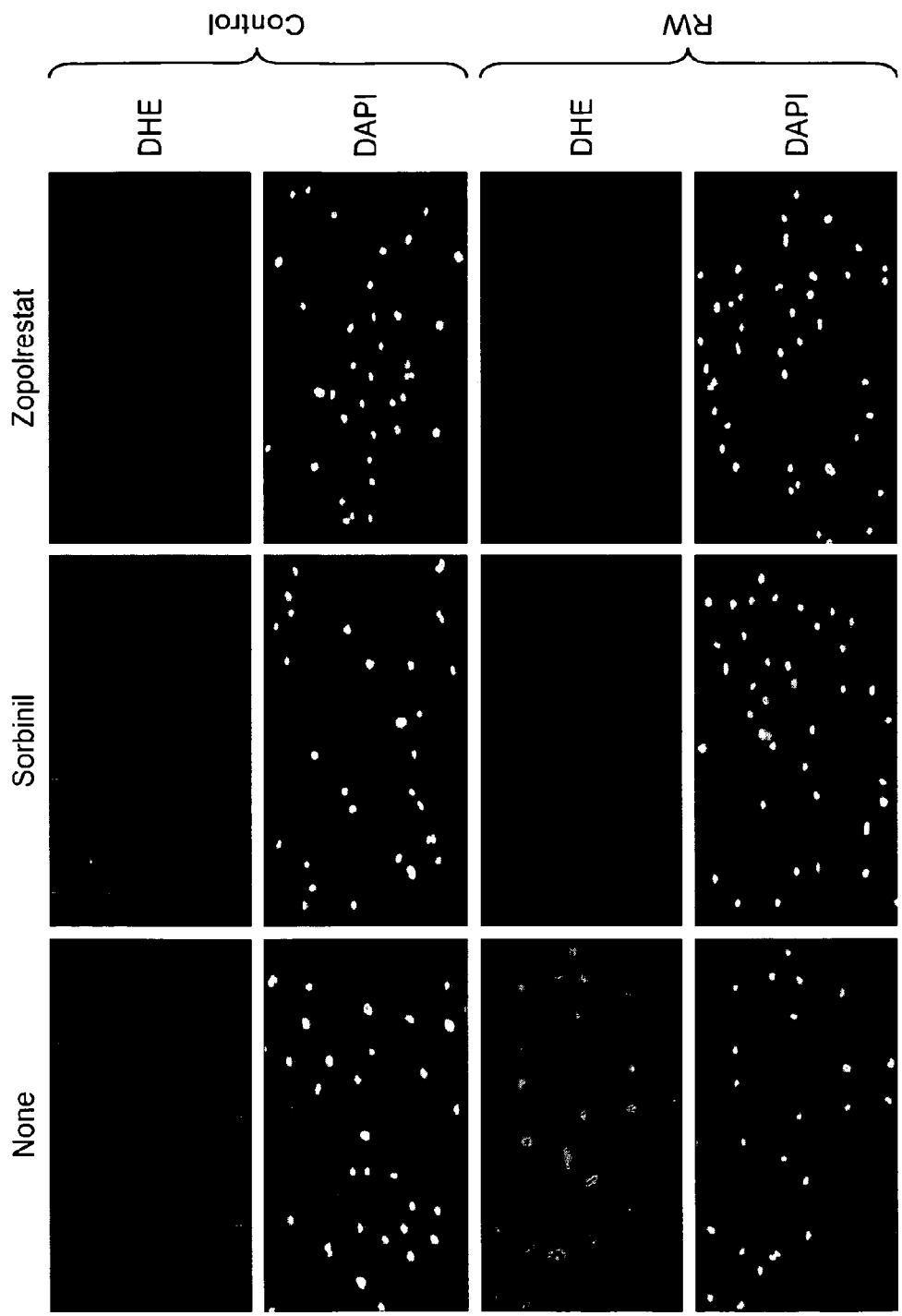
FIG. 12 Inhibition of AR prevents RW-induced ROS generation in SAEC. Approximately $1\times10^5$ cells were seeded on chambered slides and starved in serum-free basal medium with or without AR inhibitor for 24 h. The cells were treated with RW for 16 h. The SAEC were washed with cold PBS (pH 7.2) and stained with ROS-sensitive dye, dihydrocthidium (DHE) for 15 min at 37° C. The cells were washed again and mounted with floursave (with DAPI) mounting medium. Photomicrographs were acquired by a fluorescence microscope (Nikon). A representative picture is given (n=4); Magnification 200×.

AR inhibition prevents RW-induced ROS generation in SAEC: To examine the nature of the RW-induced decrease in SAEC viability, the level of RW-induced ROS in SAEC was measured. RW (150 µg/mL) caused increase in cellular ROS levels as evident by increased fluorescence by ROS sensitive DHE causing oxidative stress, which could be responsible for the loss in cell viability. Preincubation of SAEC with two different AR inhibitors, sorbinil or zopolrestat, prevented these changes (FIG. 12). Under the similar conditions, AR inhibition alone caused no significant changes in the ROS levels of SAEC. These results suggest that AR mediates RW-induced ROS formation and resultant cell death.

Figure 13A:
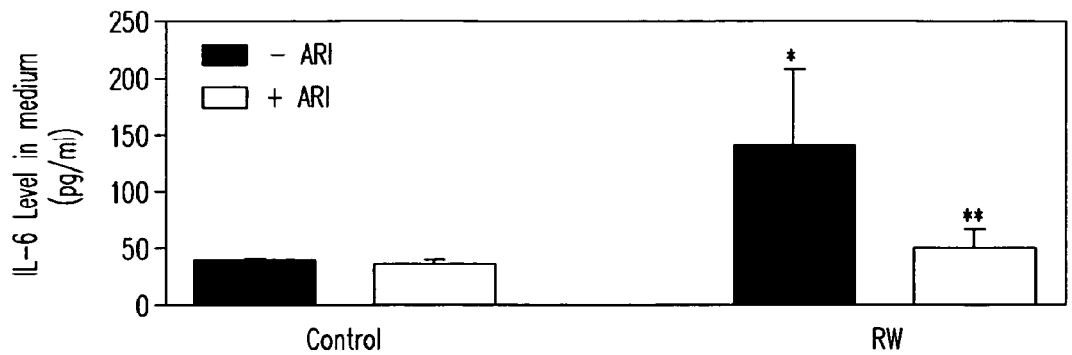
FIGS. 13A-13C Inhibition of AR prevents RW-induced secretion of inflammatory markers IL-6, IL-8 and PGE2 in SAEC. Approximately $2\times10^5$ SAECs were seeded in 6-well plates and incubated until 80% confluency. The cells were starved in serum-free basal medium with or without zopolrestat for 24 h. The cells were incubated with Ragweed (50 μg/ml) for additional 24 h. The medium was harvested, centrifuged and supernatant was used for the determination of IL-6, IL-8 and PGE2 with respective ELISA kits following supplier's manuals. Bars represent Mean±SD (n=4); $*p<0.05$ Vs Control; $\#\#p<0.001$ Vs control; $\#\#\#p<0.01$ Vs RW alone $**p<0.05$ Vs RW alone.
Figure 13B:
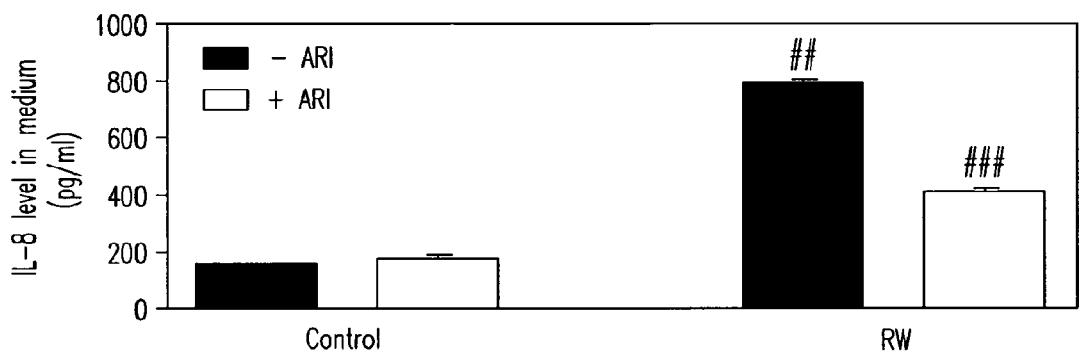
Figure 13C:
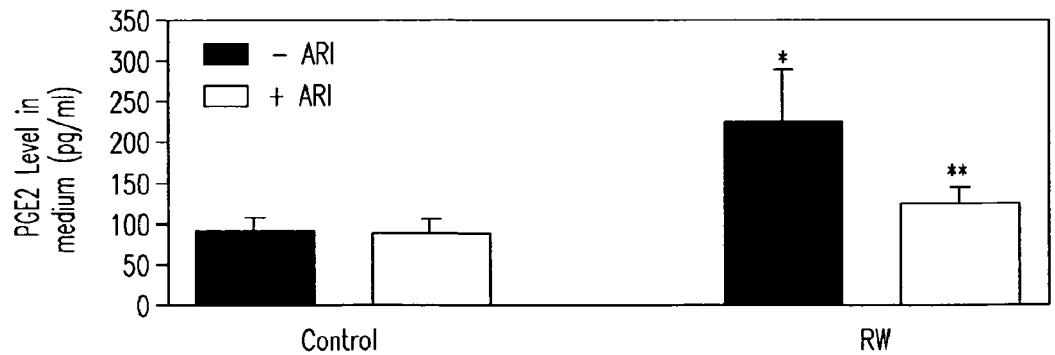

AR inhibition prevents RW-induced production of inflammatory markers (chemokines and cytokines) by SAEC: Since RW is known to elevate the levels of inflammatory markers in the airway epithelial cells that cause inflammation and aggravate the allergic condition, the effect of AR inhibition on the RW-induced increase in the levels of various inflammatory markers was examined in SAEC culture medium. As shown in FIG. 13, treatment of SAEC with 50 µg/mL RW for 24 hours caused 3 and 4-fold increases in the synthesis of IL-6, and IL-8, respectively, and inhibition of AR significantly prevented these changes. A more than 2-fold increase in the RW-induced PGE2 levels in SAEC was also significantly (>75%) prevented by AR inhibition (FIG. 13).

Figure 14A:
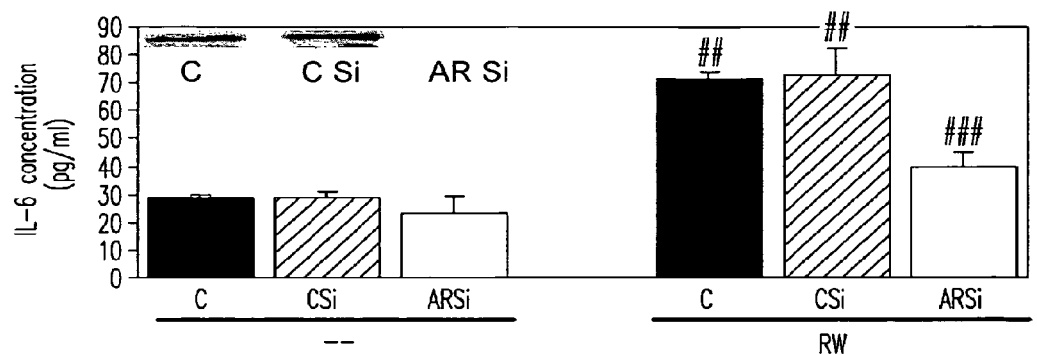
FIGS. 14A-14C Genetic ablation of AR prevents RW-induced secretion of inflammatory markers IL-6, IL-8 and PGE2. Approximately $2\times10^5$ cells were seeded in 6-well plates and incubated until 80% confluency. The cells were transfected with AR-SiRNA or scrambled-SiRNA in basal medium. After 48 h cells were treated with RW (50 Ag/ml) and incubated for an additional 24 h. The medium was harvested, centrifuged and supernatant was used for the determination of IL-6, IL-8 and PGE2 with respective ELISA kits following supplier's manuals. Bars represent Mean±SD (n=4); #$p<0.01$ Vs Control; ##$p<0.001$ Vs control; ###$p<0.01$ Vs RW.
Figure 14B:
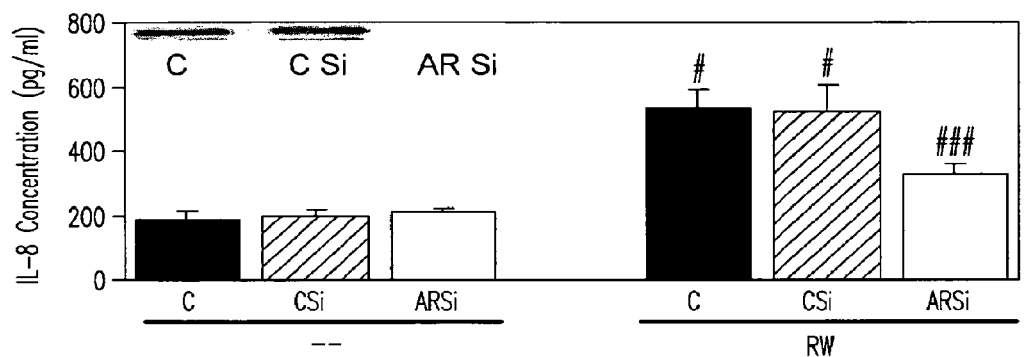
Figure 14C:
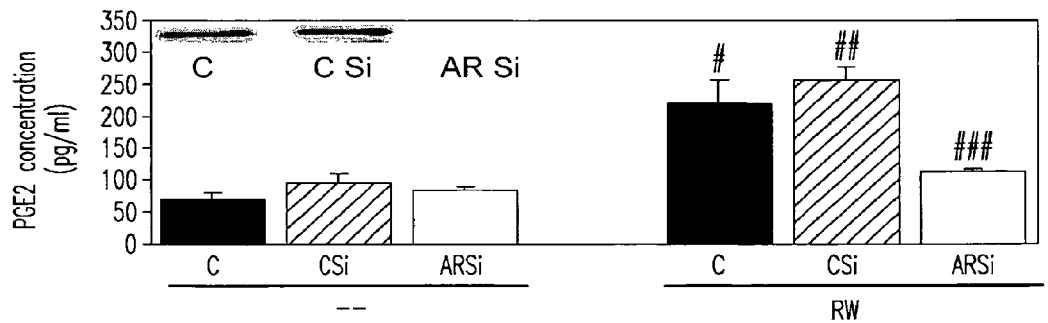

Although zopolrestat is a specific inhibitor of AR, to rule out its non-specific response in the biological system, AR message in SAEC was ablated by antisense oligonucleotides (AR siRNA) and studied whether phenotypic absence of AR will have similar effects in SAEC as did AR inhibitor in protection against RW-induced inflammation. Transient transfection of SACE with AR siRNA abolished AR protein by >95% (FIG. 14 inset) while with scrambled siRNA oligonucleotides did not change AR expression. siRNA ablation of AR also significantly prevented RW-induced synthesis of cytokines such as IL-6, and chemokines IL-8 and PGE2 in SAEC (FIG. 14). These results suggest that AR is an obligatory mediator in the RW-induced synthesis of inflammatory markers.

Figure 15:
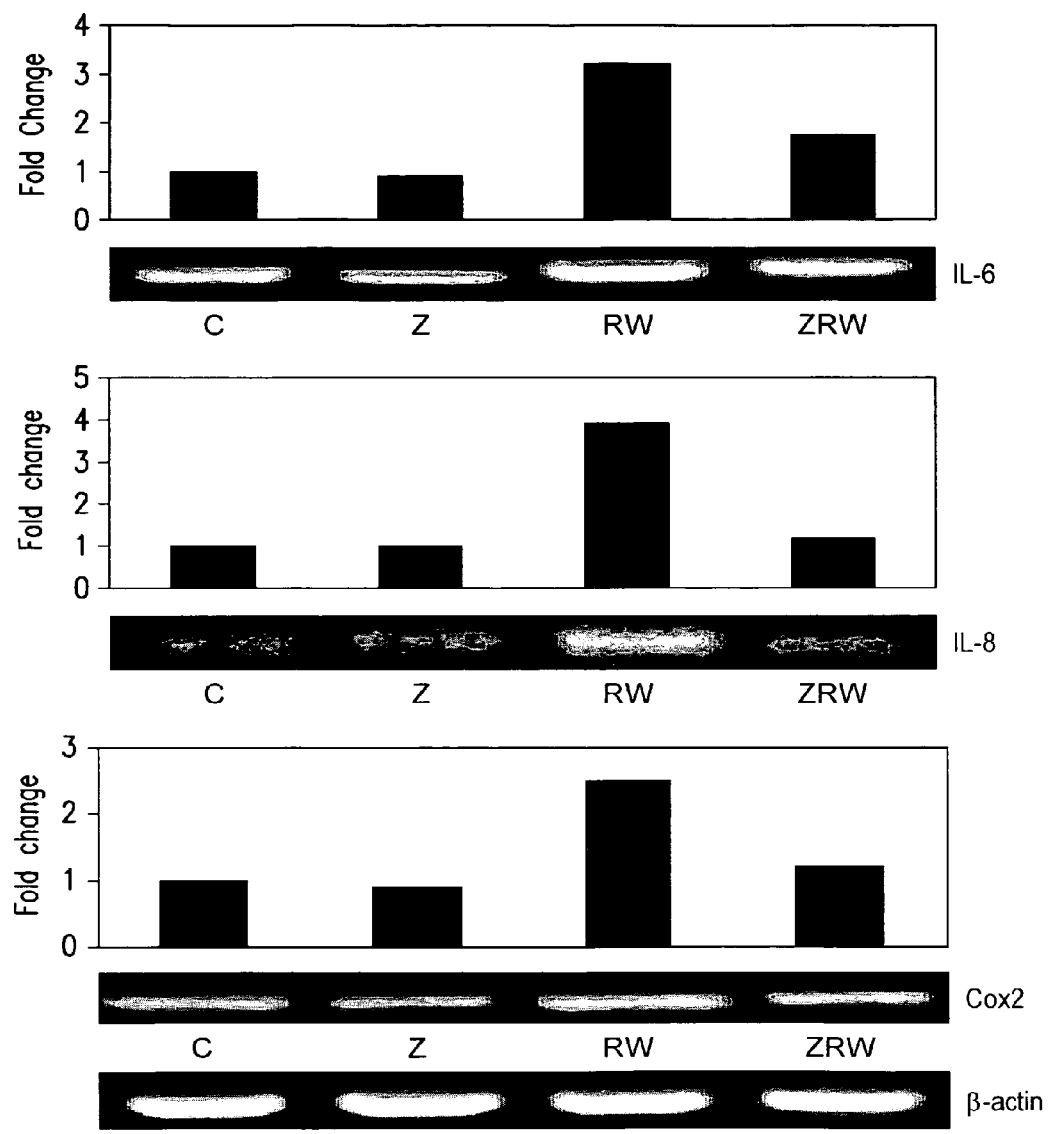
FIG. 15 Inhibition of AR prevents RW-induced expression of IL-6 and IL-8 and COX-2 mRNA in SAEC. Approximately $2\times10^5$ SAEC were seeded in 6-well plates and incubated until 80% confluency. The cells were starved in serum-free basal medium with or without zopolrestat for 24 h. The cells were treated with RW (50 μg/ml) for 6 h. Total RNA was extracted as described in the methods and IL-6, IL-8 and Cox-2 mRNA expression was determined using Qiagen RT-PCR kit. β-Actin was used as loading control. A representative gel showing amplified PCR products is shown (n=3).

AR inhibition prevents expression of RW-induced inflammatory markers in SAEC: The effects of AR inhibition on the expression of these inflammatory markers at RNA levels was further examined using RT-PCR. As shown in FIG. 15, treatment of SAEC with RW caused a 3-4 fold increase in the expression of IL-6 and IL-8 mRNA levels and zopolrestat prevented it by >70% suggesting that AR could regulate the transcriptional activation of inflammatory marker genes. Also, since PGE2 is synthesized by COX2, the effect of AR inhibition on the transcriptional activation of COX2 was determined by quantification of its mRNA in response to RW in SAEC by RT-PCR. As shown in FIG. 15, RW significantly increased the mRNA levels of COX-2 in SAEC and zopolrestat prevented it by >60% suggesting that AR could regulate the transcriptional activation of COX-2 gene. These results suggest that AR regulates the synthesis of inflammatory markers at the transcription levels.

Figure 16A:
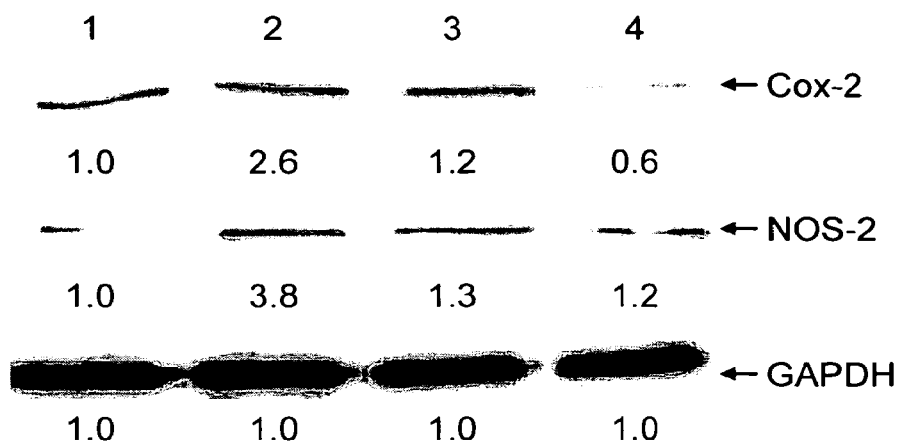
FIGS. 16A-16C Inhibition of AR prevents RW-induced expression and activation of inflammatory, apoptosis and cell cycle proteins in SAEC. Approximately $2\times10^5$ SAEC were seeded in 6-well plates and incubated until 80% confluency. The cells were starved in serum-free basal medium with or without zopolrestat for 24 h. The cells were treated with RW (50 μg/ml) for 24 h. Cell lysate was prepared and immunoblotting was performed using antibodies against Cox2, iNOS, Bcl-XL, Bax, Cyclin D1, and E2F2 to determine the expression of various proteins. GAPDH was used as loading control. Representative blots are shown (n=3), numbers below the blots represent fold changes. Lanes: 1, control; 2, Ragweed; 3, Control+Zop; 4, RW+Zop.

AR inhibition prevents RW-induced synthesis of inflammatory markers proteins in SAEC: Since biosynthesis of PGE2 and NO from their precursors is catalyzed by COX-2 and iNOS enzymes, respectively, the effect of AR inhibition on RW-induced COX-2 and iNOS expression in SAEC was next examined by immunoblotting. As shown in FIG. 16A, treatment of SAEC with RW significantly (~3-folds) increased COX-2 and iNOS protein expression and pre-treatment of SAEC with AR inhibitor, zopolrestat, significantly prevented the increase. This indicated that RW-induced COX-2 and iNOS overexpression is mediated by AR which is obligatory for RW-induced PGE2 and NO production that leads to Cytotoxicity and tissue damage during pollen allergy.

Figure 16B:
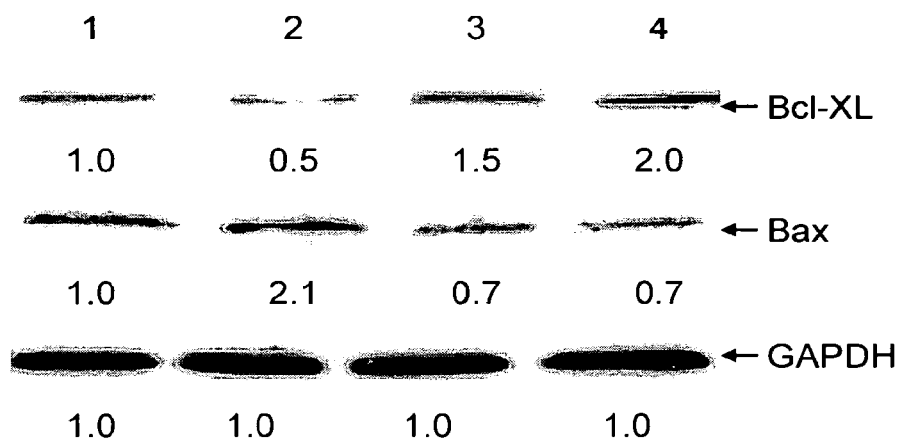

AR inhibition maintains the ratio of pro- and anti-apoptotic proteins in SAEC: Since apoptosis is regulated by the fine balance between the pro-apoptotic (Bax) and anti-apoptotic (Bcl-XL) proteins, the effect of AR inhibition on the expression of these proteins was next examined. As shown in FIG. 16B RW caused more than 2-fold increased expression of pro-apoptotic protein Bax while the expression of anti-apoptotic protein Bcl-XL decreased by 50%. The over-all ratio of these two proteins in control cells was 1 which increased significantly (to 4.2) in RW-treated cells Inhibition of AR not only controlled the expression of these proteins but it also maintained the ratio to less than 1. These results suggest that AR inhibition prevents the RW-induced alteration in the ratio of pro- and anti-apoptotic proteins and thereby inhibits apoptosis in these cells.

Figure 16C:
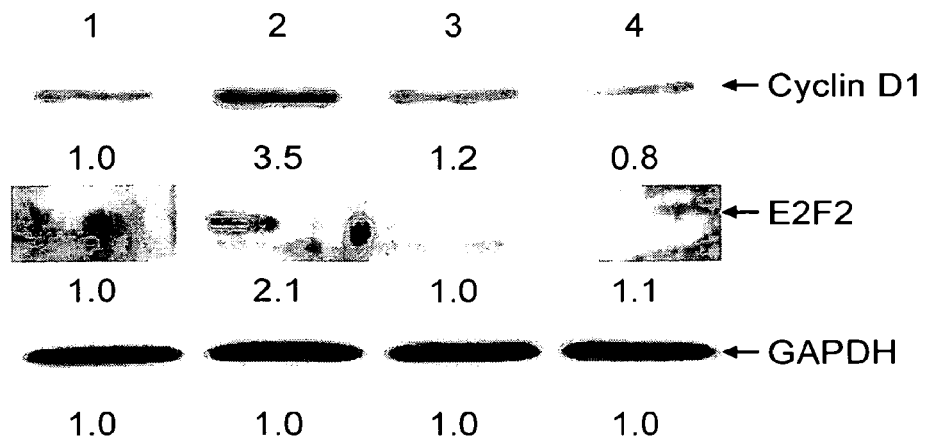

AR inhibition prevents RW-induced over-expression of cell cycle proteins in SAEC: Under oxidative stress number of cells entering the cell division cycle is altered which is regulated by a fine balance of cell cycle proteins. Whether AR inhibition will affect the level of cell cycle proteins in RW treated SAEC was next examined. As shown in FIG. 16C, RW caused >3.5 fold increased expression of cyclin D1 and >2.5 fold increased expression in E2F2 proteins. Inhibition of AR by zopolrestat prevented the increase in expression of these cell cycle protein significantly (>90%). These results suggest that inhibition of AR is critical to maintaining the cell cycle in the event of oxidative stress and prevent cell from undergoing apoptosis.

Figure 17A:
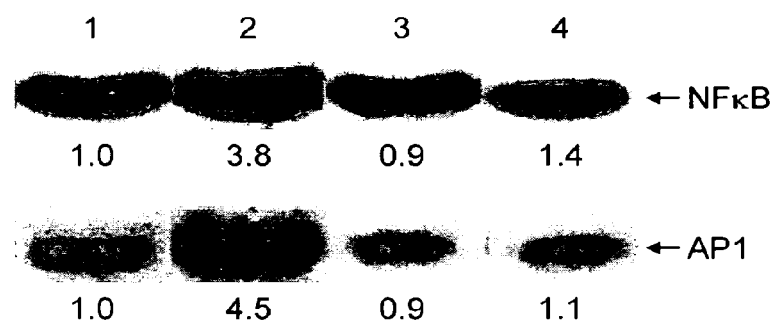
FIGS. 17A-17B AR inhibition attenuates the activation of redox-sensitive transcription factors NF-kB and AP-1 SAEC.

AR inhibition prevents RW-induced activation of NF-κB and AP1 in SAEC: The effect of AR inhibition on RW-induced activation of NF-κB and AP1 was next examined because these transcription factors are responsible for the transcription of various inflammatory markers. As shown in FIG. 17A, RW caused approximately 4-fold activation of NF-κB and AP-1 and zopolrestat significantly (>80%) prevented the RW-induced NF-κB activation and nuclear translocation. Zopolrestat alone did not affect the basal NF-κB activity in the SAEC.

Figure 17B:
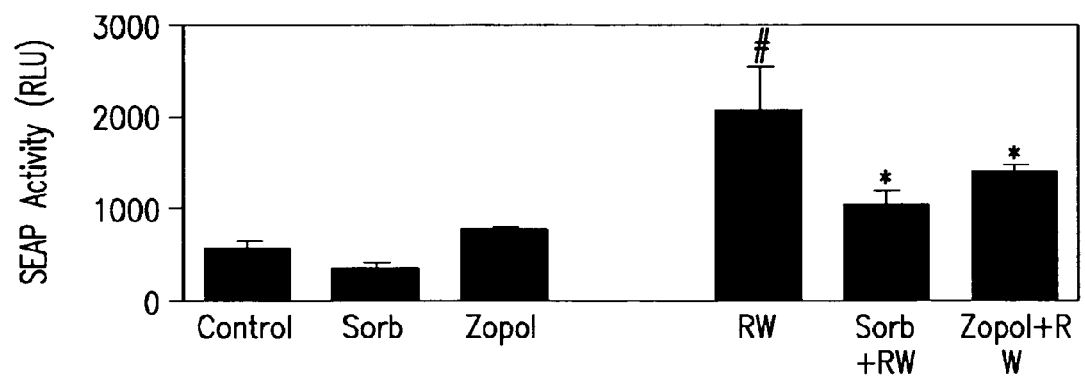

For additional confirmation of NF-κB activation by RW, NF-κB-dependent secretory alkaline phosphatase (SEAP) reporter assay were employed. It was found that RW significantly (>3-fold) induced NF-κB-dependent SEAP activation in SAEC and sorbinil as well as zopolrestat caused >60% inhibition (FIG. 17B). However, sorbinil and zopolrestat alone did not affect the NF-κB-SEAP activity. These results validated our measurement of DNA binding activity of NF-κB by gel shift assay. Based on these observations, the inventors concluded that inhibition of AR prevents RW-induced activation of NF-κB, which could activate the expression and synthesis of inflammatory markers in SAEC.

Figure 18A:
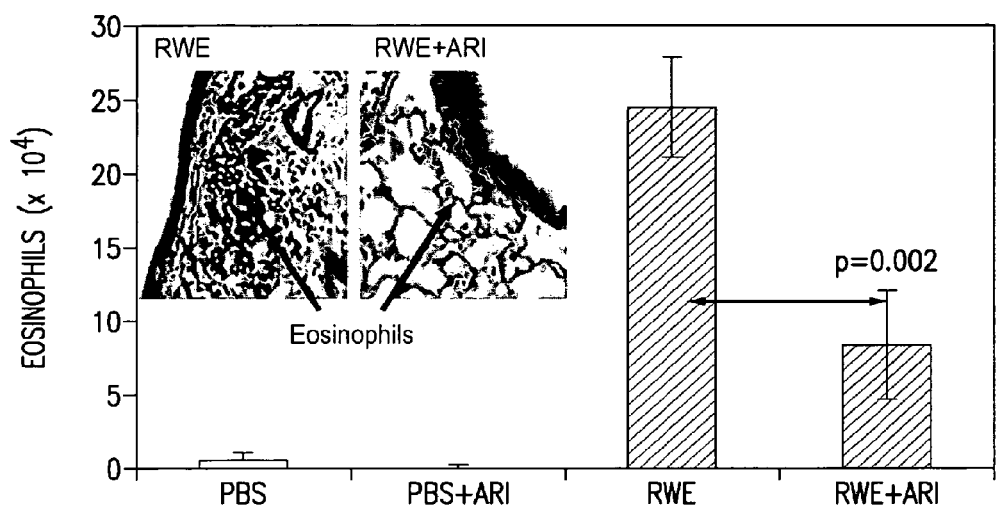
FIGS. 18A-18B AR inhibition prevents RW-induced accumulation of eosinophils in airways in mice model of asthma.
Figure 18B:
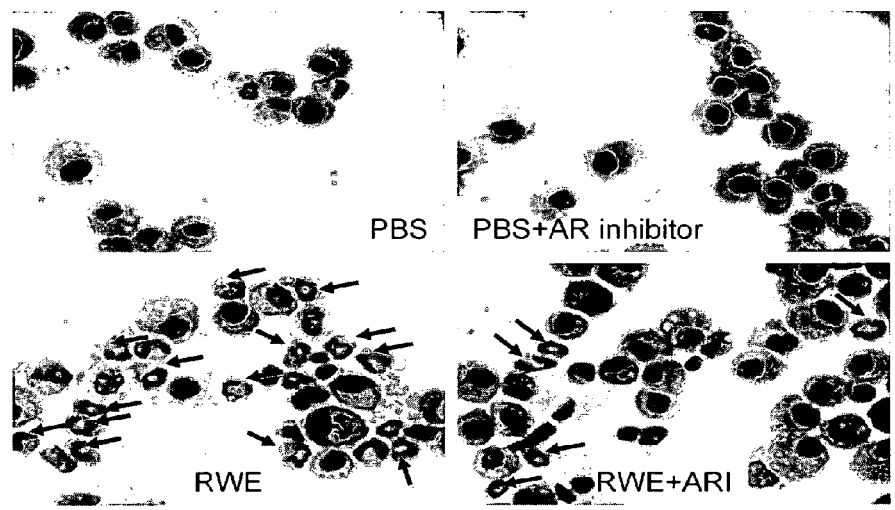

AR inhibition prevents RW-induced accumulation of eosinophils in airways in mice model of asthma: Since inflammatory response of RW challenge to SAEC was blocked significantly by AR inhibition, the inventors tested whether this approach would work in the animal models as well. We, therefore sensitized and challenged the BALB/c mice with RW- or carrier-treated without or with AR inhibitor. As shown in FIG. 18A, there was a robust airway inflammation as measured by accumulation of inflammatory cells in BAL fluid and subepithelial spaces in RW-sensitized and challenged mice. In the mice treated with AR inhibitor there was significantly less inflammation as determined by the number of eosinophils which decreased significantly ($p<0.002$). Similarly, Perivascular and peribronchial inflammation and cell composition in the BAL fluid induced by RW challenge was significantly prevented by AR inhibitor treatment (FIG. 18B).

Figure 19A:
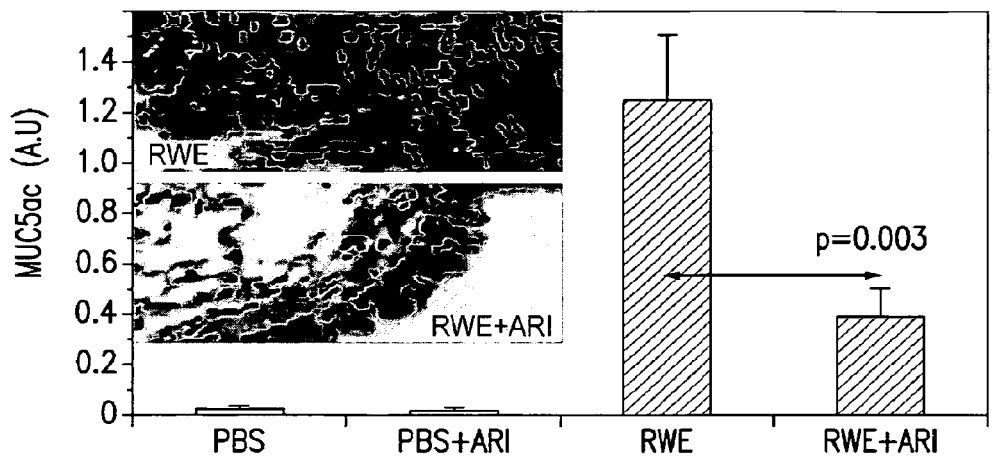
FIGS. 19A-19B AR inhibition prevents RW-induced (FIG. 19A) accumulation of MUC5AC in the BAL fluid and (FIG. 19B) hyper-responsiveness in mice model of asthma.
Figure 19B:
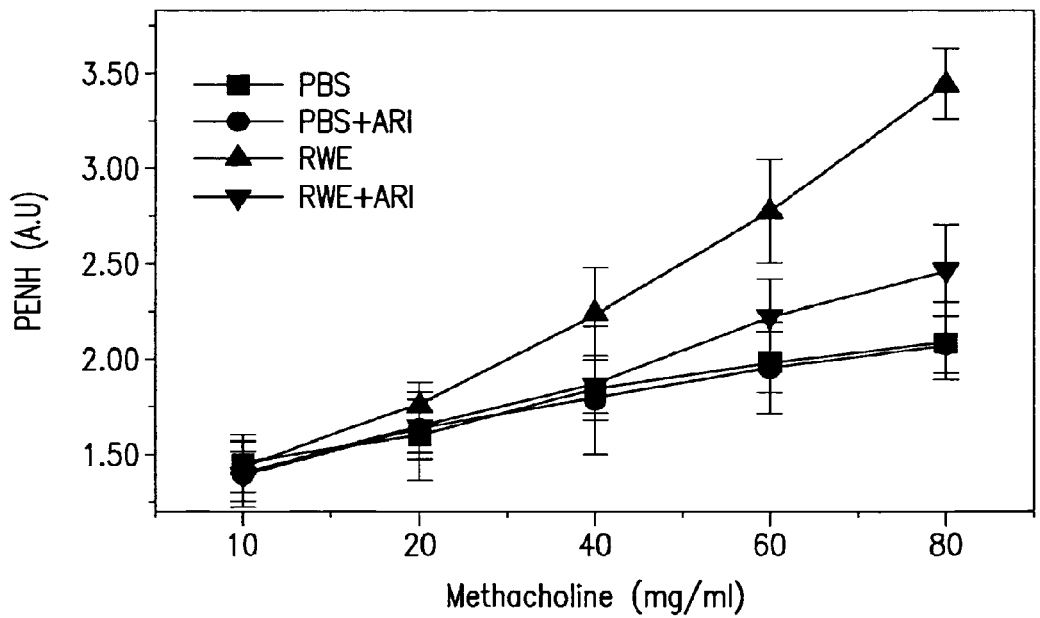

AR inhibition prevents RW-induced accumulation of Muc5Ac in the BAL fluid: Excessive mucin production by airway epithelium is characteristic of allergic asthma and its prevention is the main goal to treat allergic episodes in susceptible individuals. Therefore, the MUC5AC levels in the BAL fluid by ELISA were next examined using anti-MUC5AC monoclonal antibodies and found that MUC5AC increased ~25-folds in RW-challenged mice as compared to control and AR inhibition prevented it significantly ($p<0.003$). Similarly, mucin production in the epithelial cells as assessed by periodic acid Schiff (PAS)-staining of lung sections (FIG. 19A, inset) was also prevented by AR inhibition. In addition, whole body unrestrained plethysmography was used to quantitatively measure airway responsiveness in mice after methacholine challenge. As shown in FIG. 19B, Penh elevated dose-dependently in response to methacholine challenge as compared to control mice treated with PBS alone. Pretreatment of mice with AR inhibitor decreased the Penh values significantly from methacholine alone-challenged mice and were similar to those of control mice at all the doses. These results indicate that AR inhibition significantly prevented the patho-physiological effects of allergic asthma in murine model.

Example 4

Aldose Reductase Inhibition Suppresses Airway Hyperresponsiveness

I. Methods

Reagents: Small airway epithelial basal medium (SABM), and small airway epithelial growth media (SAGM™) bulletkit; and one Reagentpack™ containing Trypsin 0.025%/EDTA 0.01%, Trypsin neutralizing solution and HEPES buffered saline solution were purchaged from Cambrex Bio Sciences Walkersvillle, Inc. (Walkersville, Md.). Aldose reductase inhibitors Sorbinil and Zopolrestat were obtained as gift from Pfizer (New York, N.Y.). Dimethyl sulfoxide (DMSO) was obtained from Fischer scientific (Pittsburgh, Pa.). TNF-α was purchased from Research diagnostics Inc (Concord, Mass.), LPS from *Escherichia coli* was obtained from Sigma (Sigma-Aldrich, Saint Louise, Mo.). Nitrite/Nitrate and $PGE_2$ assay kits were obtained from Cayman Chemical Inc (Ann Arbor, Mich.). Human IL-6 and IL-8 ELISA kits were from Diaclone (Stamford, Conn.) and R&D systems, respectively. Antibodies against Cox2, iNOS, Bcl-XL, Bax, GAPDH, cyclin-D1 and E2F2 were from Santa Cruz Biotechnology Inc. (Santa Cruz, Calif.); and antibodies against phospho-IκB were from Cell signaling (Danvers, Mass.). Dihydroethidium (Drip fluorescent dye was purchased from Molecular Probes, Invitrogen (Carlsbad, Calif.) and polyclonal antibodies against human recombinant AR were made for us by Alpha diagnostic intl. San Antonio, Tex. The reagents used in the electrophoretic mobility shift assay (EMSA) and Western blot analysis were obtained from Sigma. All other reagents used were of analytical grade.

Cell Culture: Small Airway Epithelial cells (SAEC) obtained from Cambrex Bio Science Walkersville, Inc. (Walkersville, Md.) from distal airspace of an 18 yr old male donor. The cells were cultured according to the supplier's instructions at 37° C. in humidified incubator with 95% $O_2$ and 5% $CO_2$ in small airway epithelial basal medium (SABM) supplemented with 52 µg/ml bovine pituitary extract, 0.5 ng/ml human recombinant epidermal growth factor (EGF), 0.5 µg/ml epinephrine, 1 µg/ml hydrocortisone, 10 µg/ml transferrin, 5 µg/ml insulin, 0.1 ng/ml retinoic acid (RA), 6.5 ng/ml triiodothyronine, 50 µg/ml Gentamicin/Amphotericin-B (GA-1000), and 50 µg/ml fatty acid-free bovine serum albumin (BSA).

Cell Viability Assays: The SAEC were plated at 5000 cells/well in a 96-well plate. After they attached, cells were growth-arrested for 24 h by replacing complete medium with fresh basal medium with AR inhibitor sorbinil (20 µM) or carrier. The cells were incubated with TNF-α (2 nM) or LPS (1 µg/mL) or carrier for an additional 24 hours. Cell viability was detected by the MTT assay as described earlier. After the incubation, 10 µL of MTT (5 mg/ml) was added to each well and incubated at 37° C. for 2 h. The medium was removed and the formazan granules obtained were dissolved in 100% dimethyl sulfoxide (DMSO). Absorbance was detected at 570 nm with a 96-well ELISA reader.

In situ detection of superoxide: Dihydroethidium (DHE, Molecular Probes) staining for superoxide was carried out as described previously. Briefly, approximately $1\times10^5$ cells were seeded on chambered slides and starved in serum-free basal medium with AR inhibitor or carrier for 24 h. The cells were treated with TNF-α (2 nM) or LPS (1 µg/mL) or carrier for an additional 16 h. SAEC were rinsed with cold PBS and incubated in PBS containing HEt (2.5 µmol/L) at 37° C. for 15 min. Cells were rinsed in PBS and mounted with fluorsave mounting medium containing DAPI (Vector Laboratories Inc., Burlingame, Calif.). The image of ethidium staining was measured with a Nikon epifluorescence microscope with a 585 nm long-pass filter. Generation of superoxide in the cells was demonstrated by strong red fluorescent labeling.

Prostaglandin E2, IL-6 and IL-8 Assays: Approximately $2 \times 10^5$ SAEC/well were seeded in 6-well plates in triplicate for each group. The medium was replaced with serum-free basal medium with AR inhibitor, sorbinil (20 µM) or carrier. The growth-arrested cells were treated with either TNF-α (2 nM) or LPS (1 µg/mL) or carrier for another 24 h. The medium was collected from each well, centrifuged and the supernatant was analyzed for PGE2 (Cayman Chemical Co., Ann Arbor, Mich.); IL-6 (Diaclone, Stamford, Conn.) and IL-8 (R&D systems Inc, Minneapolis, Minn.) by using respective ELISA kits according to the manufacturer's instructions.

Determination of IL-6, IL-8 and Cox-2 expression by RT-PCR: The SAEC were grown in 6-well plates at a density of approximately $3.0 \times 10^5$ cells/well. After approximately 80% confluence cells were serum-starved in the presence or absence of sorbinil (20 µM) or carrier for 24 h and then stimulated with either TNF-α (2 nM) or LPS (1 µg/mL). Total RNA from SAEC was isolated by using RNeasy kit (Qiagen) as per supplier's instructions. Aliquots of RNA (0.5-1.0 µg) isolated from each sample were reverse transcribed with Omniscript and Sensiscript reverse transcriptase one-step RT-PCR system with HotStar Taq DNApolymerase (Qiagen) at 55° C. for 30 min followed by PCR amplification. The oligonucleotide primer sequences were as follows: 5'-ATGAACTCCTTCTCCACAAGCGC-3' (SEQ ID NO:3) (sense) and 5'-GAAGAGCCCTCAGGCTGGACTG-3' (SEQ ID NO:4) (antisense) for IL-6; 5'-ATGACTTCCAAGCTGGCCGTGGCT-3' (SEQ ID NO:5) (sense) and 5'-TCT CAGCCCTCTTCAAAAACTTCTC-3' (SEQ ID NO:6) (antisense) for IL-8; 5'-TGAAACCCACTCCA AACACAG-3' (SEQ ID NO:7) (sense) and 5'-TCATCAGGCACAGGAGGAAG-3' (SEQ ID NO:8) (antisense) for Cox-2; and 5'-ATCTGGCACCACACCTTCTACAAT-GAGCTGCG-3' (SEQ ID NO:9) (sense) and 5'-CGTC ATACTCCTGCTTGCTGATCCACATCTGC-3' (SEQ ID NO:10) (antisense) for β-actin. PCR was carried out in a PCR Sprint thermal cycler (Thermo electron corporation, Milford, Mass.) under the following conditions: initial denaturation at 95° C. for 15 min followed by 35 cycles of 94° C. 1 min, 62° C. 1 min, 72° C. 1 min, and then 72° C. 10 min for final extension. PCR products were electrophoresed with 1.5% agarose-1×TAE gels containing 0.5 µg/ml ethidium bromide. The densitometry analyses of the blots were performed by using Kodak 1D image analysis software.

Electrophoresis mobility gel shift assay: The SAEC were plated in T-150 cm² culture flasks and incubated until 80% confluence and pretreated with AR inhibitor sorbinil or carrier for 24 h in starving medium, followed by treatment with TNF-α (2 nM) for 1 h and LPS (1 µg/ml) for 2 h at 37° C. The nuclear extracts were prepared as described. Briefly, SAEC cells were harvested and washed with cold PBS and suspended in 0.1 ml of hypotonic lysis buffer containing protease inhibitors for 10 min. The cells were then lysed with 5 µl of 10% Nonidet P-40. The homogenate was centrifuged (6000 rpm; 1 min), and supernatant containing the cytoplasmic extracts was stored frozen at −80° C. The nuclear pellet was resuspended in 50 µl ice-cold nuclear extraction buffer. After 30 min of intermittent mixing, the extract was centrifuged (12000 rpm; 15 min), and supernatants containing nuclear extracts were secured. The protein concentration was measured by the Bradford method. If they were not used immediately, nuclear extracts were stored at −80° C. The Consensus oligonucleotides for NF-κB and AP-1 transcription factors were 5'-end labeled using T4 polynucleotide kinase. EMSA was performed as described in the art. The specificity of the assay was examined by competition with an excess of unlabeled oligonucleotide and supershift assays with antibodies to p65.

NF-κB-Dependent reporter secretory alkaline phosphatase expression Assay: SAEC cells ($1 \times 10^5$ cells/well) were plated in 24-well plates, serum starved in basal medium with AR inhibitor, sorbinil and zopolrestate (20 µM) or carrier for 24 h, and transiently transfected with pNF-κB-secretory alkaline phosphatase (SEAP) construct or control plasmid pTALSEAP DNA (Clontech, Palo Alto, Calif.) using the LipofectAMINE Plus reagent. After 6 hours of transfection medium was replaced with fresh medium and cells were incubated with either TNF-α (2 nM) or LPS (1 µg/mL) or carrier for 48 h. The cell culture medium was then harvested and analyzed for SEAP activity, essentially as described by the manufacturer (Clontech, Palo Alto, Calif.), using a 96-well chemiluminescence plate reader.

RNA Interference Ablation of AR in SAECs: The ablation of AR mRNA was essentially carried out as described in the art. Briefly, $2 \times 10^5$ SAECs were plated in a 6-well plate and grown till >80% confluency. The cells were incubated with serum-free medium containing the AR-siRNA (AATCGGT-GTCTCCAACTTCAA) (SEQ ID NO:1) or scrambled siRNA (AAAATCTCCCTAAATCA TACA (SEQ ID NO:2); control) to a final concentration of 100 nM and the RNAiFect™ transfection reagent (Qiagen). The cells were cultured for 48 h at 37° C., and AR expression was determined by measuring AR protein by Western blot analysis using anti-AR antibodies.

Western blotting: The cells after incubations were lysed in RIPA lysis buffer, and forty micrograms of cytoplasmic proteins were resolved on 10% SDS-PAGE gel. After electrophoresis, the proteins were electro-transferred to a nitrocellulose membrane, blocked with 5% nonfat milk in TBST, and probed with antibodies against COX-2, NOS2, Bcl-XL Bax, cyclin D1, E2F2 (1:1,000 dilution) for 2 hr. The blot was then washed, exposed to HRP-conjugated secondary antibodies (1:5,000 dilution) for 1 hr, and the antigen-antibody complex was detected by enhanced chemiluminescence (Amersham Pharmacia Biotech, Piscataway, N.J., USA).

Animals: Mice (C57BL/6; wild type) were bred in a specific-pathogen free facility at LSUHSC, New Orleans, La., and allowed unlimited access to sterilized chow and water. Maintenance, experimental protocols, and procedures were all approved by the LSUHSC Animal Care & Use Committee.

Protocols for sensitization, challenge and administration of drugs: Six to eight-weeks old C57BL/6 wild type mice were sensitized with injections (i.p.) of 100 µg Grade V chicken ovalbumin (OVA) (Sigma-Aldrich, St. Louis Mo.), mixed with 2 mg aluminum hydroxide in saline, once a week for 2 consecutive weeks followed by a challenge with aerosolized OVA a week after the second sensitization. The mice were challenged by placing them in groups of six in a Plexiglas chamber and were exposed for 30 min to aerosolized OVA (3% OVA in saline). The OVA aerosol was generated by a Bennett nebulizer (DeVilbiss, Pa.). A group of mice received an injection of 25 mg/kg AR inhibitor (i.p.) prior to challenge. Control groups were not sensitized or challenged. The mice that were used in each experiment were of the same litter.

Organ recovery and staining: Animals were killed by $CO_2$ asphyxiation and lungs were dissected out, fixed with formalin for histological analysis, subjected to branchioalveolar lavage (BAL) or collected for homogenization to prepare cell suspension for cytokine or IgE assessment. Formalin-fixed lungs were sectioned and subjected to hematoxylin and eosin (H&E) or Periodic Acid-Schiff (PAS) staining using standard protocols. Collected BAL fluids were subjected to cyto-spin and stained with H&E for the assessment of number and percent of eosinophils.

Cytology: BAL fluids were centrifuged at 1000×g for 10 min at 4° C., and the supernatant was stored immediately at −80° C. The cell pellets were resuspended in 250 µl of phosphate-buffered saline (PBS) containing 2% bovine serum albumin (BSA), and the total cell count was determined with an automated counter (Coulter Electronics, Hialeah, Fla.) and recorded as the total number of inflammatory cells per milliliter. The cell suspension was adjusted to a density of 200 cells/µl, and 100 µl of the diluted suspension was centrifuged at 800×g for 10 min with a Cytospin (International Equipment, Needham Heights, Mass.) onto coated Superfrost Plus microscope slides (Baxter Diagnostics, Deerfield, Ill.). The cells on the slides were air-dried, fixed for 30 s with Diff-Quik fixative (American Scientific Products, McGaw, Ill.), and stained first with Diff-Quik solution I for 60 s and then with Diff-Quik solution II for 60 s. After washing with deionized water for 30 s, the slides were allowed to dry before the application of mounting medium and a cover slip. Differential counts were performed for ~200 cells according to standard morphological criteria by a pathologist blinded to the treatment groups.

Cytokine assessment: The concentration of total IL-4, IL-5, and MCP1 was determined using the Bio-Rad Bioplex System for mouse according to the manufacturer instructions.

Statistical analysis: Data presented as mean ± SE and P values were determined by unpaired Student's t test. P<0.05 was considered as statistically significant.

II. Results

AR Inhibition prevents TNF-α- and LPS-induced SAEC Apoptosis: To determine the effects of AR inhibition on TNF-α and LPS-induced cell viability in the SAEC, cell viability was measured by MTT assay. Both TNF-α and LPS respectively caused loss of viability in SAEC by approximately 42 and 26%, and inhibition of AR prevented it (FIG. 20). AnnexinV staining procedure was also used in which annexinV binds to the inverted phosphotedyl serine in the cells undergoing apoptosis, propidium-iodide was used as the indicator of the cell mortality. As shown in FIG. 21 both TNF-α and LPS caused approximately 75 and 56% more cell death as compared to control cells in 18 h of treatment. Pre-incubation of the cells with AR inhibitors significantly prevented cell death (FIG. 21). Under similar conditions, AR inhibition alone did not cause apoptosis of SAECs.

AR inhibition prevents TNF-α- and LPS-induced ROS generation in SAEC: Since it is known that both TNF-α and LPS cause oxidative stress which could cause decrease in SAEC viability, the levels of reactive oxygen species in SAEC were measured. As shown in FIG. 22, both TNF-α and LPS caused a significant increase in the ROS levels as indicated by increased ethidium staining in TNF-α and LPS treated cells, suggesting increased oxidative stress which would explain increased death of SAEC. Pre-incubation of the cells with two different AR inhibitors sorbinil or zopolrestat prevented these changes (FIG. 22). AR inhibition alone caused no significant changes in the ROS levels of SAEC.

AR inhibition prevents TNF-α- and LPS-induced production of inflammatory markers and cytokines by SAEC: TNF-α and LPS are known to elevate the levels of inflammatory markers in the airway epithelial cells that cause inflammation aggravating the allergic condition. Therefore, the effect of AR inhibition on the TNF-α and LPS-induced increase in the levels of various inflammatory markers in the SAEC culture medium were examined. As shown in FIG. 23, treatment of SAEC with TNF-α (2 nM) for 24 hours caused approximately 4-fold increase in the synthesis of IL-6, and >19 fold increase in IL-8, respectively, and inhibition of AR significantly (>80%) prevented these changes. Approximately 2.5-fold increase in the PGE2 secretion was found in TNF-α-treated cells, which was significantly prevented by AR inhibition. Similarly, LPS treatment also increased (1.5-3 folds) the levels of various cytokines and chemokines, which were also significantly prevented by AR inhibition (FIG. 23).

In order to rule out non-specific effects of zopolrestat in the biological system AR in SAEC was ablated by antisense oligonucleotides (AR siRNA) to study whether phenotypic absence of AR will have similar effects in SAEC as does AR inhibitor. Transient transfection of SACE with AR antisense abolished AR protein by >95% (FIG. 23) while with scrambled antisense oligonucleotides AR activity as well as protein expression were not affected. Anti-sense ablation of AR also significantly prevented the TNF-α and LPS-induced IL-6, IL-8 and PGE2 production in SAEC similar to the pharmacological inhibitor of AR (FIG. 24). The inhibitory effect of AR inhibition or ablation on the expression of inflammatory proteins was further confirmed by their expression at RNA level using RT-PCR. As shown in FIG. 25, treatment of SAECs with TNF-α and LPS caused >3-fold increase in the expression of IL-6 mRNA level and AR inhibition prevented it by >60%. Similarly, TNF-α and LPS respectively caused ~8- and 4 fold increase in the expression of IL-8 mRNA and inhibition of AR prevented these changes by >70%. These results suggest that AR could regulate the transcriptional activation of inflammatory marker genes as well. Also, since PGE2 is synthesized by an inducible enzyme COX2, the effect of AR inhibition on its transcriptional activation was determined by quantification of its mRNA by RT-PCR in response to TNF-α and LPS. As shown in FIG. 25, TNF-α and LPS significantly increased the mRNA levels of Cox-2 by 3.5 and 2.5 folds, respectively in SAEC and zopolrestat prevented the increase by >60% suggesting that AR could regulate the transcriptional activation of Cox-2 gene.

AR inhibition prevents TNF-α- and LPS-induced synthesis of inflammatory marker proteins in SAEC: Since biosynthesis of PGE2 and NO from their precursors is catalyzed by Cox-2 and iNOS enzymes, respectively the effect of AR inhibition on TNF-α- and LPS-induced Cox-2 and iNOS expression in SAEC was next examined by immunoblotting. Treatment of SAEC with TNF-α and LPS significantly increased Cox-2 and iNOS protein expression by ~3.5 and ~2-folds and pre-treatment of cells with AR inhibitor zopolrestat significantly prevented this increase (FIG. 26). These results indicate that AR-dependent Cox-2 and iNOS overexpression is required for PGE2 and iNOS production that leads to Cytotoxicity and tissue damage during airway inflammation.

AR inhibition prevents TNF-α- and LPS-induced imbalance in the ratio of pro- and anti-apoptotic proteins in SAEC: Since apoptosis is regulated by the fine balance between the pro-apoptotic (Bax) and anti-apoptotic (Bcl-x1) proteins, the effect of AR inhibition on the expression of these proteins was next examined. As shown in FIG. 26, TNF-α and LPS caused more than ~2-fold increased expression of pro-apoptotic protein, Bax while the expression of anti-apoptotic protein, Bcl-x1 decreased by 50%. The over-all ratio of pro- and anti-apoptotic proteins in control cells was 1 which increased significantly to approximately 3 in TNF-α- and LPS-treated cells Inhibition of AR not only controlled the expression of these proteins but it also maintained the ratio to less than one. These results suggest that AR inhibition could prevent the TNF-α- and LPS-induced apoptosis in these cells by maintaining the ratio of pro- and anti-apoptotic protein to ~1.

AR inhibition prevents TNF-α- and LPS-induced overexpression of cell cycle proteins in SAEC: Since under oxidative stress, the number of cells entering cell cycle is altered, the inventors examined whether AR inhibition will affect the level of cell cycle proteins in SAECs. As shown in FIG. 26, TNF-α and LPS caused ~2.5-fold increase in the expression of cyclin D1 and E2F2 proteins and inhibition of AR significantly (>90%) prevented the increase indicating that inhibition of AR is critical to maintaining the cell cycle in the event of oxidative stress and prevention of apoptosis.

AR Inhibition prevents TNF-α- and LPS-induced Activation of NF-κB and AP1 in SAEC: The redox-sensitive transcription factors such as NF-κB and AP1 are responsible for the transcription of various inflammatory markers. Therefore, the effect of AR inhibition on TNF-α- and LPS-induced activation of NF-κB and AP1 was examined. As shown in FIG. 27A, TNF-α and LPS respectively caused ~3 and 2-fold activation of NF-κB as well as AP-1 and AR inhibition significantly prevented it. AR inhibitor alone did not affect the basal NF-κB activity in the SAECs.

For additional confirmation of NF-κB activation by TNF-α and LPS, a NF-κB-dependent secretory alkaline Phosphatase (SEAP) reporter assay was used. As shown in FIG. 28, TNF-α and LPS, respectively caused more than 7 and 2.5 fold increased NF-κB-dependent reporter (SEAP) activation in SAECs. Two structurally different inhibitors of AR, sorbinil and zopolrestat, caused >60% inhibition (FIG. 27B) of NF-κB-dependent SEAP activation. However, sorbinil and zopolrestat alone did not affect the basal NF-κB-SEAP activity. These results validate our measurement of DNA binding activity of NF-κB by gel shift assay. Based on these observations, the inventors conclude that inhibition of AR prevents TNF-α and LPS-induced activation of NF-κB, which would activate the expression and synthesis of inflammatory markers in SAEC.

These results suggest that by modulating the TNF-α- and LPS-induced activation of redox-sensitive transcription factors, AR inhibitors could prevent the production of inflammatory markers and therefore Cytotoxicity in airway inflammation.

AR inhibition prevents cytokine production and inflammatory cells (eosinophils) infiltration in ovalbumin-induced murine model of asthma: The levels of Cytokines such as IL-4, IL-5 and chemokine such as MCP-1 in BAL fluids were significantly elevated in OVA-challenged mice as compared to control mice. Treatment with AR inhibitor significantly (p<0.05) prevented the increase in cytokines and chemokines significantly (p<0.05) (FIG. 28A). Similarly, FIG. 28B shows that OVA-sensitization and challenge induced a clear and marked perivascular and peribronchial infiltration of eosinophils, a trait of allergic airway inflammation, into the lungs of C57BL/6 mice. Such infiltration of inflammatory cells into the airways of OVA-challenged mice was greatly reduced in wild type animals that received a single i.p. injection of the AR inhibitor prior to challenge. Control (unsensitized and unchallenged) mice exhibited no eosinophil recruitment.

References

The following references, to the extent that they provide exemplary procedural or other details supplementary to those set forth herein, are specifically incorporated herein by reference.

U.S. Pat. No. 4,130,714
U.S. Pat. No. 4,251,528
U.S. Pat. No. 4,436,745
U.S. Pat. No. 4,438,272
U.S. Pat. No. 4,464,382
U.S. Pat. No. 4,540,704
U.S. Pat. No. 4,600,724
U.S. Pat. No. 4,734,419
U.S. Pat. No. 4,771,050
U.S. Pat. No. 4,791,126
U.S. Pat. No. 4,831,045
U.S. Pat. No. 4,883,410
U.S. Pat. No. 4,883,800
U.S. Pat. No. 4,980,357
U.S. Pat. No. 5,037,831
U.S. Pat. No. 5,066,659
U.S. Pat. No. 5,252,572
U.S. Pat. No. 5,270,342
U.S. Pat. No. 5,354,855
U.S. Pat. No. 5,430,060
U.S. Pat. No. 5,447,946
U.S. Pat. No. 5,582,981
U.S. Pat. No. 5,756,291
U.S. Pat. No. 5,780,610
U.S. Pat. No. 5,792,613
U.S. Pat. No. 5,840,867
U.S. Pat. No. 5,990,111
U.S. Pat. No. 6,127,367
U.S. Pat. No. 6,380,200
U.S. Pat. No. 6,696,407
U.S. Pat. No. 6,720,348
U.S. patent application Ser. No. 10/462,223
U.S. patent application Ser. No. 11/210,283
U.S. Patent Publication 20030105051
U.S. Patent Publication 20030059944
U.S. Provisional Application 60/388,213
U.S. Provisional Application 60/603,725
Alexander et al., *Invest Ophthalmol Vis Sci.* 44:2683-2688, 2003.
Altan-Yaycioglu et al., *Ocul Immunol Inflamm.* 14:171-179, 2006.
Bacsi et al., *J Allergy Clin Immunol,* 116: 836-843, 2005.
Barany and Merrifield, *Anal Biochem.* 95(1):160-70, 1979.
Barisani et al., *FEBS Lett.* 469(2-3):208-12, 2000.
Berzal-Herranz et al., *Genes Dev.* 6(1):129-34, 1992.
Bhatnager and Srivastava, *Biochem Med Metab Biol.* 48(2): 91-121, 1992.
Boldogh et al., *J Clin Invest.* 115:2169-2179, 2005.
Bowie and O'Neill, *Biochem. Pharmacol.* 59:13-23, 2000.
Brito et al., *Invest Ophthalmol Vis Sci.* 40:2583-2589, 1999.
Brummelkamp et al., *Science,* 296(5567):550-3, 2002.
Burgstaller et al., *Curr Opin Drug Discov Devel.* 5(5):690-700, 2002.
Cech et al., *Cell.* 27(3 Pt 2):487-96, 1981.
Chang and Crapo, *Free Radic Biol Med.* 33(3):379-86, 2002.
Chang et al., *Br J Ophthalmol.* 90:103-108, 2006.
Chang and Crapo, *Free Radic Biol Med.* 33:379-386, 2002.
Chattedee and Fisher, *Am J Physiol Lung Cell Mol Physiol.* 287:L704-L705, 2004.
Chowrira et al., *J Biol Chem.* 268(26):19458-62, 1993.
Chowrira, et al., *J Biol Chem.* 269(41):25856-64, 1994.
Corradi et al., *Eur Respir J.* 24:1011-1017, 2004.
Curi et al., *Acute anterior uveitis. Clin Evid* 2005; 14:739-743, 2005.
Curnow and Murray, *Curr Opin Ophthalmol.* 17:532-537, 2006.
Dick et al., *Prog Reti Eye Res.* 23:617-637, 2004.
Dixit et al., *J Biol Chem.* 275:21587-21595, 2000.
Dudek et al., *Free Radic Biol Med.* 31:651-658, 2001.

Dukes, ed, Meyler's Side Effects of Drugs, Amsterdam: Elsevier; 1996:1189-1209, 1996.
Duygulu et al., *Clin Rheumatol.* 24:324-330, 2005.
Elbashir et al., *Genes Dev.* 15(2):188-200, 2001.
El-Remessy et al., *Invest Ophthalmol Vis Sci.* 44:3135-3143, 2003.
El-Shabrawi and Hermann, *Ophthalmology.* 109:2342-2346, 2002.
Fang et al., *J Ocul Pharmacol Ther.* 21:95-106, 2005.
Forster and Symons, *Cell.* 50(1):9-16, 1987.
Franks et al., *Curr Eye Res.* 11:187-191, 1992.
Fraser, *Cell Cycle.* 5:1160-1163, 2006.
Frode-Saleh and Calixto, *Inflamm Res.* 49:330-337, 2000.
Gagliardo et al., *Am J Respir Crit Care Med.* 168:1190-1198, 2003.
Galvcz et al., *J Biol Chem.* 278:38484-38494, 2003.
Griendling et al., *Circ. Res.* 74:1141-1148, 1994.
Gupta and Murray, *Drugs Aging.* 23:535-558, 2006.
Hale and Lightman, *Cytokine.* 33:231-237, 2006.
Hamilton et al., *Am J Respir Cell Mol Biol.* 15:275-282, 1996.
Haseloff and Gerlach, *Nature.* 334(6183):585-91, 1988.
Humber, "Aldose Reductase Inhibition: An Approach to the Prevention of Diabetes Complications", Porte, ed., Ch. 5, pp. 325-353.
Hwang et al., *FASEB J.* 19:795-797, 2005.
Iwata et al., *J Biol Chem.* 274:7993-8001, 1999.
Joseph et al., *Ophthalmology.* 110:1449-1453, 2003.
Joyce, *Gene.* 82(1):83-7, 1989.
Kim and Cech, *Proc Natl Acad Sci USA.* 84(24):8788-92, 1987.
Kitamci et al., *J Leukoc Biol.* 79:1193-1201, 2006.
Kloek et al., *Inflamm Res.* 52:126-131, 2003.
Koga et al., *Exp Eye Res.* 75:659-667, 2002.
Kukner et al., *Acta Ophthalmol Scand.* 84:54-61, 2006.
Lieber and Strauss, *Mol Cell Biol.* 15(1):540-51, 1995.
Lin et al., *Am J. Ophthalmol.* 141:1097-104, 2006.
Lo and Cruz, *J Biol Chem.* 270:11727-11730, 1995.
Malone, *Diabetes.* (11):861-4, 1980.
Mandai et al., *Invest Ophthalmol Vis Sci.* 35:3673-3680, 1994.
Merrifield, *Science.* 232(4748):341-7, 1986.
Michel and Westhof, *J Mol. Biol.* 216(3):585-610, 1990.
Miwa et al., *Diabetes Res. Clin. Pract.* 60:1-9, 2003.
Murata et al., *Chem. Biol. Interact.* 130-132:617-625, 2001.
Mustapha et al., *J Immunol.* 177:6489-6496, 2006.
Nagata, *Curr Drug Targets Inflamm Allergy.* 4:503-504, 2005.
Nakajima and Takatsu, *Int Arch Allergy Immunol.* 142:265-273, 2006.
Nakamura et al., *Free Radic Biol Med.* 29(1):17-25, 2000.
Nussenblatt et al., *Am J Ophthalmol.* 141:193-194, 2006.
Nussenblatt, *Int Ophthalmol.* 14:303-308, 1990.
O'Connor et al., *Biochem J.* 343 Pt 2:487-504, 1999.
Ohia et al., *Mutat Res.* 579:22-36, 2005.
Ohta et al., *Invest Ophthalmol Vis Sci.* 43:744-750, 2002.
Orchard et al., *Gastroenterology.* 123:714-718, 2002.
Perriman et al., *Gene.* 113(2):157-63, 1992.
Perrotta and Been, *Biochemistry.* 31(1):16-21, 1992.
Pladzyk et al., *Invest Opthamol Vis Sci.* 47:5395-403, 2006.
Prieto et al., *Ann Allergy Asthma Immunol.* 97:175-181, 2006.
Prody et al., *Science.* 231(4745):1577-1580, 1986.
Raetz and Whitfield, *Annu Rev Biochem.* 71:635-700, 2002.
Rahman et al., *Am J Respir Crit. Care Med.* 166:490-495, 2002.
Ramana et al., *J Biol Chem.* 281:17652-17660, 2006.
Ramana et al., *FEBS Lett.* 570:189-194, 2004.
Ramana et al., *FASEB J.* 18:1209-1218, 2004.
Ramana et al., *J Biol Chem.* 275:32063-32070, 2002.
Ramana et al., *Biochemistry.* 39:12172-12180, 2000.
Ramana et al., *J Biol Chem.* 28:33019-33029, 2006.
Ramana et al., *FASEB J.* 17:315-317, 2003.
Ramana et al., *FASEB J.* 17:315-317, 2003.
Ramana et al., *Diabetes.* 54:818-829, 2005.
Ramana et al., *Circulation.* 114:1838-1846, 2006.
Ramana et al., *J. Biol. Chem.* 277:32063-32070, 2002.
Ramana et al., *Diabetes.* 53:2910-2920, 2004.
Rathinam and Cunningham, *Int Ophthalmol Clin.* 40:137-152, 2000.
Read, *Curr Rheumatol Rep.* 8:260-266, 2006.
Reinhold-Hurek and Shub, *Nature.* 357(6374):173-76, 1992
Remington's Pharmaceutical Sciences, 18th Ed. Mack Printing Company, 1990
Riffo-Vasquez and Spina, *Pharmacol Ther.* 2002; 94:185-211, 2002.
Rittner et al., *J Clin Invest.* 103(7):1007-13, 1999.
Rosenbaum, *Nature.* 286:611-613, 1980.
Rosi et al., *Lung.* 2006; 184:251-8, 2006.
Ruef et al., *Arterioscler Thromb Vasc Biol.* 20(7):1745-52, 2000.
Salvemini et al., *Proc Natl Acad Sci USA.* 90:7240-7244, 1993.
Samudre et al., *J Ocul Pharmacol Ther.* 20(6):533-47, 2004.
Santos Lacomba et al., *Ophthalmic Res.* 33:251-255, 2001.
Sarver et al., *Science.* 247(4947):1222-5, 1990.
Scanlon et al., *Proc Natl Acad Sci USA.* 88(23):10591-5, 1991.
Seo et al., *J Biol Chem.* 275(39):30355-62, 2000.
Shaw et al., *J Biol Chem.* 278:30634-30641, 2003.
Shinmura et al., *Proc Natl Acad Sci USA.* 97(18):10197-202, 2000.
Shiratori et al., *Invest Ophthalmol Vis Sci.* 45:159-164, 2004.
Singh et al., *Proteins.* 64:101-110, 2006.
Sioud et al., *J Mol Biol.* 223(4):831-5, 1992.
Spycher et al., *FASEB J.* 11(2):181-8, 1997.
Srivastava et al., *Biochem Biophys Res Commun.* 217:741-746, 1995.
Srivastava et al., *Biochemistry.* 37(37):12909-17, 1998.
Srivastava et al., *Adv Exp Med Biol.* 463:501-7, 1999.
Srivastava et al., *Endocr Rev.* 26:380-392, 2005.
Srivastava et al., *Diabetes* 2006; 55:901-910, 2006.
Streilein et al., *DNA Cell Biol.* 21:453-459, 2002.
Sui et al., *Proc Natl Acad Sci USA.* 99(8):5515-20, 2002.
Surh et al., *Mutat Res.* 480-481:243-68, 2001.
Suzuki et al., *Exp Eye Res.* 2006; 82:275-281, 2006.
Symons, *Nucleic Acids Res.* 9(23):6527-37, 1981.
Symons, *Annu Rev Biochem.* 61:641-71, 1992.
Tam et al., *Int J Pept Protein Res.* 21(1):57-65, 1983.
Tammali et al., *Cancer Res.* 66:9705-9713, 2006.
Tesfamariam et al., *J. Cardiovasc. Pharmacol.* 21:205-211, 1993.
Thompson, et al., *Nat Med.* 1(3):277-8, 1995.
Tomlinson et al. *Pharmac. Ther.* 54:151-194, 1992.
Tugal-Tutkun et al., *Arthritis Rheum.* 52:2478-2484, 2005.
Vander Jagt et al., *Biochim Biophys Acta.* 1249(2):117-26, 1995.
Wang et al., *Int Immunopharmacol.* 2:1509-1520, 2002.
Williams and Paterson, *Invest Ophthalmol Vis Sci.* 25:105-108, 1984.
Wisnewski et al., *Clin Exp Allergy.* 35:352-357, 2005.
WO 03/012052
Wood et al., *Eur Respir J.* 21:177-186, 2003.
Xiao, *Cell Mol. Immunol.* 1:425-435, 2004.
Yabe-Nishimura, *Pharmacol Rev.* 50(1):21-33, 1998.
Yang et al., *Circulation.* 102(25):3046-52, 2000.
Yuan and Altman, *Science.* 263(5151):1269-73, 1994.
Yuan et al., *Proc Natl Acad Sci USA.* 89(17):8006-10, 1992.

The invention claimed is:

1. A method of treating uveitis in a non-diabetic subject comprising: administering to a non-diabetic subject an amount of a pharmaceutically acceptable composition comprising an aldose reductase inhibitor selected from epalrestat, ponalrestat, risarestat, imirestat, zoplrestat, minalrestat AS-3201 (ranirestat) tolrestat, or fidarestat to treat uveitis.

2. The method of claim 1, wherein the composition is administered one or more times.

3. The method of claim 1, wherein the patient is administered the composition directly, locally, topically, orally, endoscopically, intratracheally, intratumorally, intravenously, intralesionally, intramuscularly, intraperitoneally, regionally, percutaneously, or subcutaneously.

4. The method of claim 3, wherein the aldose reductase inhibitor is administered orally.

5. The method of claim 1, wherein the aldose reductase inhibitor is fidarestat.

6. The method of claim 1, wherein the aldose reductase inhibitor is administered at a dose of 1 to 1500 mg/day.

7. The method of claim 6, wherein the aldose reductase inhibitor is administered at a dose of 100 to 800 mg/day.

* * * * *

SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
aatcggtgtc tccaacttca a                                              21

<210> SEQ ID NO 2
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 2
aaaatctccc taaatcatac a                                              21

<210> SEQ ID NO 3
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 3
atgaactcct tctccacaag cgc                                            23

<210> SEQ ID NO 4
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 4
gaagagccct caggctggac tg                                             22

<210> SEQ ID NO 5
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 5
atgacttcca agctggccgt ggct                                           24

<210> SEQ ID NO 6
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 6
tctcagccct cttcaaaaac ttctc                                          25

<210> SEQ ID NO 7
<211> LENGTH: 21
<212> TYPE: DNA
<213> ORGANISM: Artificial Sequence

```
<220> FEATURE:
<223> OTHER INFORMATION: synthetic oligonucleotide

<400> SEQUENCE: 7
tgaaacccac tccaaacaca g                                              21

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 8
tcatcaggca caggaggaag                                                20

<210> SEQ ID NO 9
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 9
atctggcacc acaccttcta caatgagctg cg                                  32

<210> SEQ ID NO 10
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 10
cgtcatactc ctgcttgctg atccacatct gc                                  32
```